US007332472B2

(12) United States Patent
Naicker et al.

(10) Patent No.: US 7,332,472 B2
(45) Date of Patent: *Feb. 19, 2008

(54) CYCLOSPORINE ANALOGUE MIXTURES AND THEIR USE AS IMMUNOMODULATING AGENTS

(75) Inventors: Selvaraj Naicker, Edmonton (CA); Randall W. Yatscoff, Edmonton (CA); Robert T. Foster, Edmonton (CA)

(73) Assignee: Isotechnika Inc., Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/118,830

(22) Filed: Apr. 28, 2005

(65) Prior Publication Data
US 2005/0192214 A1 Sep. 1, 2005

Related U.S. Application Data

(63) Continuation of application No. 10/274,255, filed on Oct. 17, 2002, now Pat. No. 6,998,385.

(60) Provisional application No. 60/370,596, filed on Apr. 5, 2002, provisional application No. 60/346,201, filed on Oct. 19, 2001.

(51) Int. Cl.
A61K 38/13 (2006.01)

(52) U.S. Cl. .................. 514/11; 530/321; 530/350; 530/806

(58) Field of Classification Search ............... None
See application file for complete search history.

(56) References Cited

U.S. PATENT DOCUMENTS

| | | | |
|---|---|---|---|
| 4,108,985 A | 8/1978 | Rüegger et al. |
| 4,117,118 A | 9/1978 | Harri et al. |
| 4,160,452 A | 7/1979 | Theeuwes |
| 4,177,188 A | 12/1979 | Hansen |
| 4,201,771 A | 5/1980 | Onishi et al. |
| 4,210,581 A | 7/1980 | Rüegger et al. |
| 4,220,641 A | 9/1980 | Traber et al. |
| 4,256,108 A | 3/1981 | Theeuwes |
| 4,265,874 A | 5/1981 | Bonsen et al. |
| 4,288,431 A | 9/1981 | Traber et al. |
| 4,289,851 A | 9/1981 | Harri et al. |
| 4,384,996 A | 5/1983 | Bollinger et al. |
| 4,396,542 A | 8/1983 | Wenger |
| 4,404,194 A | 9/1983 | Arala-Chaves |
| 4,554,351 A | 11/1985 | Wenger |
| 4,639,434 A | 1/1987 | Wenger et al. |
| 4,681,754 A | 7/1987 | Siegl |
| 4,703,033 A | 10/1987 | Seebach |
| 4,727,018 A | 2/1988 | Eichner et al. |
| 4,764,503 A | 8/1988 | Wenger |
| 4,765,980 A | 8/1988 | DePrince et al. |
| 4,771,122 A | 9/1988 | Seebach |
| 4,798,823 A | 1/1989 | Witzel |
| 4,839,342 A | 6/1989 | Kaswan |
| 4,866,036 A | 9/1989 | Durette |
| 4,868,155 A | 9/1989 | Durette |
| 4,868,157 A | 9/1989 | Durette |
| 4,885,276 A | 12/1989 | Witzel |
| 4,914,188 A | 4/1990 | Dumont et al. |
| 4,963,362 A | 10/1990 | Rahman et al. |
| 4,963,683 A | 10/1990 | Avery et al. |
| 4,970,076 A | 11/1990 | Horrobin |
| 4,996,193 A | 2/1991 | Hewitt et al. |
| 4,997,648 A | 3/1991 | Galpin et al. |
| 5,013,719 A | 5/1991 | Bowlin |
| 5,047,512 A | 9/1991 | Handschumacher et al. |
| 5,051,402 A | 9/1991 | Kurihara et al. |
| 5,068,247 A | 11/1991 | Fujita et al. |
| 5,079,341 A | 1/1992 | Galpin et al. |
| 5,084,441 A | 1/1992 | Regelson et al. |
| 5,100,889 A | 3/1992 | Misra et al. |
| 5,116,816 A | 5/1992 | Dreyfuss et al. |
| 5,122,511 A | 6/1992 | Patchett et al. |
| 5,153,327 A | 10/1992 | Misra et al. |
| 5,169,773 A | 12/1992 | Ball et al. |
| 5,171,812 A | 12/1992 | Domb |
| 5,190,935 A | 3/1993 | Binderup et al. |
| 5,190,972 A | 3/1993 | Dumble |
| 5,206,229 A | 4/1993 | Calverley et al. |
| 5,214,130 A | 5/1993 | Patchett et al. |

(Continued)

FOREIGN PATENT DOCUMENTS

BE 866810 11/1978

(Continued)

OTHER PUBLICATIONS

Abel, MD, et al., "ISATX247: A Novel Calcineurin Inhibitor", *J. Heart Lung Transpl.*, vol. 20, No. 2, p. 161 (2001) Abstract.

(Continued)

Primary Examiner—Anish Gupta
(74) Attorney, Agent, or Firm—Fish & Richardson P.C.

(57) ABSTRACT

The invention is directed to isomeric mixtures of cyclosporine analogues that are structurally similar to cyclosporine A. The mixtures possess enhanced efficacy and reduced toxicity over the individual isomers and over naturally occurring and other presently known cyclosporines and cyclosporine derivatives. Embodiments of the present invention are directed toward cis and trans-isomers of cyclosporin A analogs referred to as $ISA_{TX}247$, and derivatives thereof. Mixtures of $ISA_{TX}247$ isomers exhibit a combination of enhanced potency and reduced toxicity over the naturally occurring and presently known cyclosporins. $ISA_{TX}247$ isomers and alkylated, arylated, and deuterated derivatives are synthesized by stereoselective pathways where the particular conditions of a reaction determine the degree of stereoselectivity. The ratio of isomers in a mixture may range from about 10 to 90 percent by weight of the (E)-isomer to about 90 to 10 percent by weight of the (Z)-isomer, based on the total weight of the mixture.

43 Claims, 14 Drawing Sheets

U.S. PATENT DOCUMENTS

| | | |
|---|---|---|
| 5,219,884 A | 6/1993 | Fujita et al. |
| 5,227,467 A | 7/1993 | Durette et al. |
| 5,236,899 A | 8/1993 | Durette |
| 5,239,057 A | 8/1993 | Wang et al. |
| 5,256,547 A | 10/1993 | Rudat et al. |
| 5,270,419 A | 12/1993 | Domb |
| 5,284,826 A | 2/1994 | Eberle |
| 5,298,523 A | 3/1994 | Longley et al. |
| 5,318,901 A | 6/1994 | Patchett et al. |
| 5,321,043 A | 6/1994 | Dumble |
| 5,342,625 A | 8/1994 | Hauer et al. |
| 5,350,574 A | 9/1994 | Erlanger et al. |
| 5,356,633 A | 10/1994 | Woodle et al. |
| 5,371,081 A | 12/1994 | Houghton et al. |
| 5,382,655 A | 1/1995 | Szanya et al. |
| 5,385,915 A | 1/1995 | Buxbaum et al. |
| 5,389,382 A | 2/1995 | List et al. |
| 5,393,669 A | 2/1995 | Brown |
| 5,401,649 A | 3/1995 | Davalian et al. |
| 5,401,731 A | 3/1995 | Calverley et al. |
| 5,405,785 A | 4/1995 | Erlanger et al. |
| 5,409,816 A | 4/1995 | Lundell et al. |
| 5,411,952 A | 5/1995 | Kaswan |
| 5,427,960 A | 6/1995 | Wang et al. |
| 5,446,034 A | 8/1995 | Bretting et al. |
| 5,447,924 A | 9/1995 | Bretting et al. |
| 5,468,772 A | 11/1995 | Xu et al. |
| 5,489,668 A | 2/1996 | Morrison et al. |
| 5,498,421 A | 3/1996 | Grinstaff et al. |
| 5,510,239 A | 4/1996 | Baracchini et al. |
| 5,514,788 A | 5/1996 | Bennett et al. |
| 5,525,590 A | 6/1996 | Bollinger et al. |
| 5,527,820 A | 6/1996 | Ishizuka et al. |
| 5,540,931 A | 7/1996 | Hewitt et al. |
| 5,545,633 A | 8/1996 | Bretting |
| 5,554,599 A | 9/1996 | Grue-Sørensen et al. |
| 5,554,725 A | 9/1996 | Pettit |
| 5,571,799 A | 11/1996 | Tkachuk et al. |
| 5,578,444 A | 11/1996 | Edwards et al. |
| 5,589,458 A | 12/1996 | Jameson et al. |
| 5,589,471 A | 12/1996 | Hansen et al. |
| 5,591,623 A | 1/1997 | Bennett et al. |
| 5,616,595 A | 4/1997 | Chu et al. |
| 5,627,044 A | 5/1997 | Brown |
| 5,632,991 A | 5/1997 | Gimbrone |
| 5,635,207 A | 6/1997 | Grinstaff et al. |
| 5,637,317 A | 6/1997 | Dietl |
| 5,639,473 A | 6/1997 | Grinstaff et al. |
| 5,639,724 A | 6/1997 | Cavanak |
| 5,639,852 A | 6/1997 | Rich et al. |
| 5,643,870 A | 7/1997 | Boelsterli et al. |
| 5,648,376 A | 7/1997 | Strobel et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,665,543 A | 9/1997 | Foulkes et al. |
| 5,667,764 A | 9/1997 | Kopia et al. |
| 5,668,734 A | 9/1997 | Krishna et al. |
| 5,670,478 A | 9/1997 | Stuchlik et al. |
| 5,693,760 A | 12/1997 | Bringman et al. |
| 5,698,448 A | 12/1997 | Soldin |
| 5,709,797 A | 1/1998 | Bocchiola et al. |
| 5,741,512 A | 4/1998 | Hauer et al. |
| 5,741,775 A | 4/1998 | Balkovec et al. |
| 5,747,330 A | 5/1998 | Casareto et al. |
| 5,750,413 A | 5/1998 | Lunetta et al. |
| 5,750,678 A | 5/1998 | Bauer |
| 5,756,706 A | 5/1998 | Mansour et al. |
| 5,767,069 A | 6/1998 | Ko et al. |
| 5,834,266 A | 11/1998 | Crabtree et al. |
| 5,840,305 A | 11/1998 | Bukrinsky et al. |
| 5,871,753 A | 2/1999 | Belshaw et al. |
| 6,605,593 B1 | 8/2003 | Naicker et al. |
| 6,613,739 B1 | 9/2003 | Naicker et al. |
| 6,613,793 B2 | 9/2003 | Naicker et al. |
| 6,998,385 B2 * | 2/2006 | Naicker et al. ............... 514/11 |
| 2003/0212249 A1 | 11/2003 | Naicker et al. |
| 2005/0176628 A1 | 8/2005 | Naicker et al. |
| 2006/0052290 A1 | 3/2006 | Naicker et al. |
| 2006/0135414 A1 | 6/2006 | Naicker et al. |

FOREIGN PATENT DOCUMENTS

| | | |
|---|---|---|
| CA | 2086267 | 6/1994 |
| CH | 630061 | 5/1982 |
| CH | 630062 | 5/1982 |
| CS | 8906499 | 8/1992 |
| CS | 8906498 | 9/1992 |
| DE | 3531597 | 3/1987 |
| DE | 3927804 | 3/1990 |
| DE | 4013910 | 10/1991 |
| DE | 4433101 | 3/1996 |
| DE | 19521974 | 12/1996 |
| DE | 19611094 | 9/1997 |
| EP | 0 056 782 | 8/1984 |
| EP | 0 034 567 | 11/1984 |
| EP | 0194972 | 9/1986 |
| EP | 0283801 | 9/1988 |
| EP | 0 296 122 A2 | 12/1988 |
| EP | 0294239 | 12/1988 |
| EP | 0296122 | 12/1988 |
| EP | 0300785 | 1/1989 |
| EP | 0321128 | 6/1989 |
| EP | 0372541 | 6/1990 |
| EP | 0372862 | 6/1990 |
| EP | 0373260 | 6/1990 |
| EP | 0414632 | 2/1991 |
| EP | 0444897 | 9/1991 |
| EP | 0473961 | 3/1992 |
| EP | 0526200 | 2/1993 |
| EP | 0 532 187 A1 | 3/1993 |
| EP | 0570829 | 11/1993 |
| EP | 0577544 | 1/1994 |
| EP | 0578616 | 1/1994 |
| EP | 0651995 | 5/1995 |
| EP | 0674178 | 9/1995 |
| EP | 0712631 | 5/1996 |
| FR | 2757520 | 6/1998 |
| FR | 2757521 | 6/1998 |
| FR | 2757522 | 6/1998 |
| GB | 2205317 | 12/1988 |
| GB | 2206119 | 12/1988 |
| GB | 2207678 | 2/1989 |
| GB | 2212499 | 7/1989 |
| GB | 2222770 | 3/1990 |
| GB | 2227244 | 7/1990 |
| GB | 2257359 | 1/1993 |
| GB | 2271121 | 4/1994 |
| JP | 63-258491 | 10/1988 |
| JP | 1277755 | 11/1989 |
| JP | 2124100 | 5/1990 |
| JP | 7278187 | 10/1995 |
| JP | 9048737 | 2/1997 |
| JP | 10029979 | 2/1998 |
| JP | 10251137 | 9/1998 |
| JP | 2001-519355 | 10/2001 |
| WO | WO 86/02080 | 4/1986 |
| WO | WO 90/00389 | 1/1990 |
| WO | WO 90/06763 | 6/1990 |
| WO | WO 92/04055 | 3/1992 |
| WO | WO 93/25533 | 12/1993 |
| WO | WO 94/23733 | 10/1994 |
| WO | WO 94/25606 | 11/1994 |
| WO | WO 95/05372 | 2/1995 |

| | | |
|---|---|---|
| WO | WO 95/05374 | 2/1995 |
| WO | WO 95/11039 | 4/1995 |
| WO | WO 95/26325 | 10/1995 |
| WO | WO 96/06857 | 3/1996 |
| WO | WO 96/22104 | 7/1996 |
| WO | WO 96/31202 | 10/1996 |
| WO | WO 96/33697 | 10/1996 |
| WO | WO 97/04005 | 2/1997 |
| WO | WO 97/25977 | 7/1997 |
| WO | WO 97/32541 | 9/1997 |
| WO | WO 97/33604 | 9/1997 |
| WO | WO 97/34639 | 9/1997 |
| WO | WO 98/08490 | 3/1998 |
| WO | WO 98/13066 | 4/1998 |
| WO | WO 98/14174 | 4/1998 |
| WO | WO 98/25590 | 6/1998 |
| WO | WO 98/46247 | 10/1998 |
| WO | WO 98/49193 | 11/1998 |
| WO | WO 99/10373 | 3/1999 |
| WO | WO 99/18120 | 4/1999 |
| WO | WO 01/21154 | 3/2001 |
| WO | WO 01/28518 | 4/2001 |
| WO | WO 03/033526 | 4/2003 |
| WO | WO 03/033527 | 4/2003 |
| WO | WO 2004/072108 | 8/2004 |
| WO | WO 2004/082629 | 9/2004 |

OTHER PUBLICATIONS

Abel, MD, et al., "ISA$_{TX}$247: A Novel Calcineurin Inhibitor with Minimal Renal Toxicity", *Am. J. of Transpl.*, vol. 1 (Supp. 1), Abstract No. 1192 (2001).

Abel, MD, et al., "Phase 1 Evaluation of a Novel Calcineurin Inhibitor ISA$_{TX}$247", *Am. J. of Transpl.*, vol. 1 (Supp. 1), Abstract No. 1319 (2001).

Abel, MD, et al., "Preclinical Efficacy of a Novel Calcineurin Inhibitor: ISA$_{TX}$247", *Am. J. of Transpl.*, vol. 1 (Supp. 1), Abstract No. 1191, (2001).

Adams, M.W., "d-Alpha Tocopheryl Polyethylene Glycol 1000 Succinate (Eastman Vitamin E TPGS) as an Emulsifier and Bioenhancer for Drugs and Lipophilic Compounds" Pamphlet by Eastman Chemical Co., (Oct. 1996).

Aspeslet, L., et al., "ISA$_{TX}$247: A Novel Calcineurin Inhibitor", *Transpl. Proc.*, vol. 33, pp., 1048-1051.

Bennet, W.M., "The Nephrotoxicity of New and Old Immunosuppressive Drugs", *Renal Failure*, vol. 20, pp. 687-690 (1998).

Bestmann, H.J., et al., "(Z)-5-Decenyl Acetate, A Sex Attractant for the Male Turnip Moth", *Agnew. Chem. Int. Ed. Engl.*, vol. 17, No. 10, pp. 768-769 (1978).

Biellmann, J.F., et al., "Allylic and Benzylic Carbanions Substituted by Heteroatoms", *Organic Reactions*, vol. 27, p. 9 (1982).

Birsan, T., et al., "Ex Vivo Evaluation of the Immunosuppressive Effect of the Novel Caldineurin Inhibitor ISATX247 on Whole Blood Lymphocytes of Non-Human Primates", *Am. J. of Transpl.*, 1(Supp. 1), Abstract No. 1199 (2001).

Borok, Z., et al., "Effect of Glutathione Aerosol on Oxidant-Antioxidant Imbalance in Idiopathic Pulmonary Fibrosis", *The Lancet*, vol. 338, pp. 215 and 697.

Carlsen, H.J., et al., "A Greatly Improved Procedure for Ruthenium Tetraoxide Catalyzed Oxidations of Organic Compounds", *J. Org. Chem.*, vol. 46, No. 19, pp. 3936-3938 (1981).

Chang, T., et al., "The Effect of Water-Soluble Vitamin E On Cyclosporine Pharmacokinetics in Healthy Volunteers", *Clin. Pharmacol. Ther.*, vol. 59, pp. 297-303 (1996).

Corey, E.J., et al., "Highly Reactive Equivalents of Allylidenetriphenylphosporanes For the Stereospecific Synthesis of 1,3-dienes by Cis-Olefination of Hindered Aldehydes", *Tetrahedron Letters*, vol. 26, No. 47, pp. 5747-5748 (1985).

Eberle, M.K., et al., "Synthesis of the Main Metabolite (OL-17) of Cyclosporin A", *J. Org. Chem.*, vol. 57, pp. 2689-2691 (1992).

Ehlinger, E., et al., "Silicon in Synthesis. 10. The (trimethylsily)allyl amion: A β-acyl anion Equivalent for the conversion of Aldehydes and Ketones into γ-Lactones", *J. Am. Chem. Soc.*, vol. 102, No. 15, pp. 5004-5011 (1980).

Fruman, D.S., et al., "Calcineurin Phosphatase Activity in T Lymphocytes Is Inhibited by FK 506 and Cyclosporin A", *Proc. Natl. Acad. Sci. USA*, vol. 89, pp. 3686-3690 (1992).

Granelli-Piperno, A., et al., "Lymphokine and Nonlymphokine mRNA Levels in Stimulated Human T Cells: Kinetics, Mitogen Requirements, and Effects of Cyclosporin A" *J. Exp. Med.*, vol. 163, p. 922-937 (1986).

Hanson, J.R., "Esters as Protecting Groups for Alcohols", *Protecting Groups in Organic Synthesis* Ch. 2, pp. 24-25 (1999).

Herbert, M.F., et al., "Bioavailability of cyclosporine with Concomitant Rifampin Administration is Markedly Less than Predicted by Hepatic Enzyme Induction", *Clin. Pharmacol. Ther.*, vol. 52, pp. 453-457 (1992).

Hoffman, R.W., et al., "Diastereoselective Addition of γ-Alkylthio-Allylboronates to to Aldehydes", *Tetrahedron Letters*, vol. 21, pp. 4883-4886 (1980).

Hoffmann, R.W., et al., "Stereoselective Synthesis of Alcohols. 8. Diastereoselective Synthesis of β-methylhomoallyl Alcohols via Crotylboronates", *J. Org. Chem.*, vol. 46, pp. 1309-1314 (1981).

Hofle, G., et al., "4-Dialkylaminopyridines as Highly Active Acylation Catalysts", *Agnew. Chem. Int. Ed. Engl.*, vol. 17, pp. 569-583 (1978).

Hurdrlik, P.F., et al., "Stereospecific Olefin-Forming Elimination Reactions of β-Hydroxyalkylsilanes", *J. Am. Chem., Soc.*, vol. 97, No. 6, pp. 1464-1468 (1975).

Ikeda, Y., et al., "Stereoselective Synthesis of (Z)- and (E)-1,3-alkadienes from Aldehydes Using Organotitanium and Lithium Reagents", *Tetrahedron*, vol. 43, No. 4, pp. 723-730 (1987).

Kobel, et al., "Directed Biosynthesis of Cyclosporins", *EP. J. Applied Microbiology and Biotechnology*, vol. 14, pp. 237-240 (1982).

Maksymowych, WP, et al., "Amelioration of Established Collagen-Induced Arthritis by ISA$_{TX}$247: a Novel Calcineurin Inhibitor", *J. of Rheum.*, 28(supp 63) Abstract.

Maksymowych, WP, et al., "Prevention and Treatment of Antigen-Induced Arthritis by ISA$_{TX}$247, A Novel Calcineurin Inhibitor", *J. of Rheum.*, vol. 28 (Supp. 63) (2001).

McMurry, J., "19.12 Nucleophilic Addition of Phosphorus Ylides: The Wittig Reaction", in *Organic Chemistry*, 5$^{th}$ Ed., pp. 780-783 (2000).

Peterson, D., "A Carbonyl Olefination Reaction Using Silyl-Substituted Organometallic Compounds", *J. Org. Chem.*, pp. 780-784 (1967).

Ramachandran, P.V., et al., eds., "Intramolecular Allylboration Reactions", in *Organoboranes for Syntheses*, pp. 162-164 and 174.

Reetz, M.T., *Organotitanium Reagents in Organic Synthesis*, pp. VII, 148-149, 162-168 (1986—Springer-Verlag, Berlin).

Rich, D., et al., "Synthesis and Antimitogenic Activities of Four Analogues of Cyclosporin A Modified in the 1-Position", *J. Med. Chem.*, vol. 29, p. 978-984 (1986).

Roush, W.R., "Allyorganometallics", *Comp. Org. Synth.*, vol. 2, pp. 1-53.

Schreiber, S.F., et al., "The Mechanism of Action of Cyclosporin A and FK506", *Immunol. Today*, vol. 13, pp. 136-142 (1992).

Shapiro, A.M.J., et al., "Prolonged Islet Allograft Survival Without Toxicity Using ISATX247: a Novel Calcineurin Inhibitor", *Am. J. of Transpl.*, vol. 1 (Supp. 1), Abstract No. 828 (2001).

Sketris, I., et al., "Optimizing the Use of Cyclosporine in Renal Transplantation", *Clin. Biochem.*, vol. 28, pp. 195-211 (1995).

Smith, M.B., et al., "Stereochemistry: Molecules with More than One Chiral (Stereogenic) Center", *March's Advanced Org. Chem.*, pp. 144-147 (2001).

Smith, M.B., et al., "The Peterson Alkenylation Reaction", *March's Advanced Org. Chem.*, pp. 1228-1229 (2001).

Sokol, R., et al., "Improvement of Cyclosporin absorption in Children After Liver Transplantation by Means of Water-Soluble Vitamin E", *The Lancet*, vol. 338, pp. 212-214 (1991).

Sokol, R., et al., "Cyclosporin and vitamin E", *The Lancet*, vol. 338, pp. 697 (1991).

Streitwieser, Jr., A., et al., "16.4 Protecting Groups" and "27.3 Preparation of Diols", Intro. to Org. Chem.,, 2nd Ed., pp. 475-476 and 844-846, respectively, (1981).
Thliveris, J.A., et al., "Chronic Ciclosporin Nephrotoxicity: A Rabbit Model", Nephron, vol. 57, pp. 470-476 (1991).
Thliveris, J.A., et al., "Chronic Cyclosporine-Induced Nephrotoxicity: A Rabbit Model", Transplantation, vol. 57, pp. 774-776 (1994).
Thomas, S.E., Organic Synthesis: the Roles of Boron and Silicon, pp. 34-35, 67-69 and 85-87 (1991).
von Rene Traber, et al., "Die Struktur von Cyclosporin C", Helv. Chim. Acta, vol. 60, pp. 1247-1255 (1977).
Traber, et al. "162. Isolierung und Strukturermittlung der neuen Cyclosporine E, F, G, H and I", Helv. Chim. Acta, vol. 65, pp. 1655-1677 (1982).
Tsai, D.J.S., et al., "A Stereocontrolled Synthesis of (Z) and (E) Terminal Dienes from Pinacol (E)-1-Trimethylsilyl-1-Propene-3-Boronate", Tetrahedron Letters, vol. 22, No. 29, pp. 2751-2752 (1981).
Ukai, J., et al., "Direct, Stereoselective Synthesis of Ether E—or—Z-1,3-Dienes", Tetrahedron Letters, vol. 24, No. 37, pp. 4029-4032 (1983).
Valantine, H.A., et al., "Recent Advances in Cardiac Transplantation", N. Eng. J. Med., [editorial comment], vol. 333, No. 10, pp. 660-661 (1995).
von Wartburg, et al., "Chemistry of the Natural Cyclosporin Metabolites", Progress in Allergy, vol. 38, pp. 28-45 (1986).
Wang, et al., "Cyclosporine Nephrotoxicity: Attenuation By an Antioxidant-Inhibitor of Lipid Peroxidation in Vitro and In Vivo", Transplantation, vol. 58, pp. 940-946 (1994).
Weidmann, B., et al., "Organometallic Compounds of Titanium and Zirconium as Selective Neucleophilic Reagents in Organic Synthesis", Agnew. Chem. Int. Ed. Engl., vol. 22, pp. 31-45 (1983).
Wenger, R., "Synthesis of Cyclosporine and Analogues: Structure, Activity, Relationaships of New Cyclosporine Derivatives", Transpl. Proc., vol. 15, Suppl. 1, pp. 2230-2241 (1983).
Wenger, R., "Synthesis of Cyclosporine and Analogues: Structural Requirements for Immunosuppressive Activity", Angew. Chem. Int. Ed., vol. 24, pp. 77-85 (1985).
Wenger, R.M., "Cyclosporine and Analogues—Isolation and Synthesis—Mechanism of Action and Structural Requirements for Pharmacological Activity", Progress in the Chemistry of Organic Natural Products, vol. 50, pp. 123-168 (1986).
Yamamoto, Y., et al., "Selective Reactions Using Allylic Metals", Chemical Reviews, pp. 2207-2293 (1993).
Yang, D., et al., "A $C_2$ Symmetric Chiral Ketone for Catalytic Asymmetric Epoxidation of Unfunctionalized Olefins", J. Am. Chem. Soc., vol. 118, pp. 491-492 (1996).
Yang, D., et al., "Novel Cyclic Ketones for Catalytic Oxidation Reactions", J. Org. Chem., vol. 63, pp. 9888-9894 (1998).
Yatscoff, RW, et al., "$ISA_{TX}247$: Phase 1 Clinical Trial Results of the Novel Calcineurin Inhibitor", J. of Rheum., vol. 28 (Supp. 63), Abstract W133 (2001).
Yatscoff, RW, et al., "Pharmacokinetics of a Novel Calcineurin Inhibitor: $ISA_{TX}247$." Therap. Drug. Monitor., vol. 23, No. 4, (2001).
Yatscoff, RW, et al., "Phase 1 Evaluation of a Novel Calcineurin Inhibitor $ISA_{TX}247$", Therp. Drug. Mon., vol. 23, No. 4, (2001).
Johannes D. Aebi et al., "Synthesis, Conformation, and Immunosuppressive Activities of Three Analogues of Cyclosporin A Modified in the 1-Position", J. Med. Chem. 1990, 33, 999-1009.
Marcel K. Eberle et al., "Modifications of the MeBmt Side Chain of Cyclosporin A", Bioorganic & Medicinal Chemistry Letters, vol. 5, No. 15, pp. 1725-1728, 1995.
Aspeslet, L,J. et al., "Requirements for Therapeutic Drug Monitoring of Sirolimus, an Immunosuppressive Agent Used in Renal Transplantation", Clinical Therapeutics, vol. 22, Supp. B (2000), pp. B86-B92.
Barrett, A.G.M. et al., "B-[3-((Diisopropylamino)dimethylsilyl)allyl]diisopinocampheylborane: An Excellent Reagent for the Stereoselective Synthesis of Anti Vicinal Diols", J. Org Chem, vol. 56 (1991), pp. 5243-5245.
Belshaw, P.J. et al., "Controlling protein association and subcellular localization with a synthetic ligand that induces heterodimerization of proteins", Proceedings of the National Academy of Sciences of the USA, vol. 93 (May 1996), pp. 4604-4607.
Brown, H.C. et al., "Chrial Synthesis via Organoboranes. 13, A Highly Diastereoselective and Enantioselective Addition of [(Z)-γ-Alkoxyallyl]diisopinocampheylboranes to Aldehydes" J Am Chem Soc, vol. 110 (1988), pp. 1535-1538.
Carruthers, S.G. et al., "Simplified Liquid-Chromotographic Analysis for Cyclosporin A, and Comparison with Radioimmunoassay", Clinical Chemistry, vol. 29, No. 1 (1983), pp. 180-183.
Chen, P. et al., "A sensitive enzyme immunoassay for cyclosporin A using antibodies generated against a novel Hapten", Research Communications in Molecular Pathology and Pharmacology, vol. 88, No. 3 (Jun. 1995), pp. 317-326.
Christians, U. et al., "Cyclosporin Metabolism in Transplant Patients", Pharmacology & Therapeutics, vol. 57, No. 2/3 (1993), pp. 291-345.
Copeland, K.R. et al., "Toxicity of Cyclosporine Metabolites", Therapeutic Drug Monitoring, vol. 12, No. 6 (Nov. 1990), pp. 525-532.
Curran, D. et al., "Intramolecular Hydrogen Transfer Reactions of o-(Bromophenyl)dialkylsilyl Ethers. Preparation of Rapamycin-$d_1$." Tetrahedron Letters, vol. 33, No. 17 (1992), pp. 2295-2298.
Harlow, E. et al., "Antibodies. A Laboratory Manual", Cold String Harbor Laboratory, New York (1988).
Hartman, N.R. et al., "Mass Spectrometric Analysis of Cyclosproine Metabolites", Biomedical & Environmental Mass Spectrometry, vol. 13, No. 7 (1986), pp. 361-372.
Hensens, O.D. et al., "The Preparation of [2-Deutero-3-Fluoro-D-ALA$^8$]Cyclosporin A By Directed Biosynthesis", Journal of Antibiotics, vol. 45, No. 1(1992), pp. 133-135.
Hon, Y.-S et al., "A convenient and efficient workup of ozonolysis reactions using triethylamine", Synthetic Communications, vol. 23, No. 11 (1993), pp. 1543-1553.
House, H.O., Modern Synthetic Reactions, W.A. Benjamin, Menlo Park, California, 2nd ed.,. (1972), pp. 302-319.
Hu, S. et al., "Diastereoselective Chloroallylboration of α-Chiral Aldehydes", J Org Chem, vol. 63 (1998), pp. 8843-8849.
Hughes, P. et al., "The Isolation, Synthesis and Characterization of An Isomeric Form of Rapamycin", Tetrahedron Letters, vol. 33, No. 33 (1992), pp. 4739-4742.
Johnson, A.W. et al., "The Chemistry of Ylids—V Trialkylphosphoniumfluorenylides Mechanism of the Wittig Reaction", Tetrahedron, vol. 9, pp. 130-138 (1960).
Johnson, R.A. et al., "4.1 Catalytic Asymmetric Epoxidation of Allylic Alcohols", Catalytic Asymmetric Synthesis, Edited by I. Ojima, VCH Publishers, New York, NY, (1993), pp. 103-158.
Keown, P.A., "Chapter 1: Molecular and Clinical Therapeutics of Cyclosporine in Transplantation", Immunosuppression in Transplantation, Edited by L. Ginns, A. Cosimi, P. Morris, Blackwell Science, Malden, MA (1999), pp. 1-12.
Marshall, J.A., "Chiral Allylic and Allenic Stannanes as Reagents for Asymmetric Synthesis", Chemical Reviews, vol. 96 (1996), pp. 31-47.
Metelitsa, D.I., "Reaction Mechanisms of the Direct Epoxidation of Aldenes in the Liquid Phase", Russian Chemical Reviews, vol. 41, No. 10 (Oct. 1972), pp. 807-821.
Patchett, A. A. et al., "Analogs of Cyclosporin A Modified at the D-ALA$^8$ Position", The Journal of Antibiotics, vol. 45, No. 1 (1992), pp. 94-102.
Sharpless, K.B. et al., "The Osmium-Catalyzed Asymmetric Dihydroxylation: A New Ligand Class and a Process Improvement", J Org Chem, vol. 57, No. 10 (1992), pp. 2768-2771.
Smulik, J.A. et al., "Synthesis of Cyclosporin A-Derived Affinity Reagents by Olefin Metathesis", Organic Letters, vol. 4, No. 12 (2002), pp. 2051-2054.
Swern, D., "Chapter 7: Epoxidation and Hydroxylation of Ethylenic Compounds with Organic Peracids", Organic Reactions, vol. 7 (1953), pp. 378-433.
Swern, D., "Organic Peracids", Chemical Review, vol. 45 (1949), p. 16.
Tamura, R. et al., "Stereoselective E and Z Olefin Formation by Wittig Olefination of Aldehydes with Allylic Phosphorus Ylides. Stereochemistry", J Org Chem, vol. 53 (1988), pp. 2723-2728.

Yohannes, D. et al., "Degradation of Rapamycin: Retrieval of Major Intact Subunits", *Tetrahedron Letters*, vol. 33, No. 49 (1992), pp. 7469-7472.

Carey, F. et al., "Scheme 2.6—Examples of Kinetic Resolutions", *Advanced Organic Chemistry: Part A: Structure and Mechanisms* (4th ed.), Kluwer Academic/Plenum Publishers, pp. 93-94.

Isotechnika, Inc., Partial European search report dated Jul. 10, 2007 of the European patent application No. 07106871, 10 pages.

Kobel, H. et al., "Contribution to knowledge of the biosynthesis of cyclosporin A", Birkhauser Verlag Basel, *Experientia*, vol. 39 (1983), pp. 873-876.

Park, S.B. et al., "A semi-synthetic approach to olefinic analogs of amino acid one (MeBMT) in cyclosporin A", *Tetrahedron Letters*, vol. 30, No. 32 (1989), pp. 4215-4218.

Prileschajew, N. "Oxydation ungesättigter Verbindungen mittels organischer Superoxyde", *Berichte der Deutschen Chemischen Gesellschaft*, (1909), pp. 4811-4815, in German and its English translation.

Rüegger, A. et al., "Cyclosporin A, ein immunsuppressiv wirksamer Peptidmetabolit aus *Trichoderma polysporum* (Link ex Pers.) Rifai", *Helvetica Chimica Acta*, vol. 59, Fasc 4, (1976), pp. 1075-1092, in German and its English translation.

Schnurpfeil, D., *Zur Katalyse der Prilesaev-Reaktion*, vol. 20 (1980), p. 445, in German and its English translation.

Seebach, D. et al., "Modification of Cyclosporin A (CS)¹): Generation of an Enolate at the Sarcosine Residue and Reactions with Electrophiles", *Helvitica Chimica Acta*, vol. 76 (1993), pp. 1564-1590.

Traber, R. et al., "Neue Cyclosporine aus *Tolypocladium inflatum* Die Cyclosporine K-Z", *Helvetica Chimica Acta*, vol. 70 (1987), pp. 13-36, in German and its English translation.

Biellmann, J.F., et al., "Allylic and Benzylic Carbanions Substituted by Heteroatoms", *Organic Reactions*, vol. 27 (1982), p. 9.

Blake, M. et al., "Studies with Deuterated Drugs", *Journal of Pharmaceutical Sciences*, vol. 64, No. 3 (Mar. 1975), pp. 367-391.

Borel, J.F. et al., "Biological Effects of Cyclosporin A: A New Antilymphocytic Agent", *Agents and Actions*, vol. 6 (1976), pp. 468-475.

Borel, J.F. et al., "Effects of the new anti-lymphocytic peptide cyclosporine A in animals", *Immunology*, vol. 32, No. 6 (Jun. 1977), pp. 1017-1025.

Calne, R.Y. et al., "Pharmacological immunosuppression in clinical organ grafting. Observations on four agents: cyclosporine A. Asta 5122 (cytimun), lambda carrageenan and promethazine hydrochloride"; *Clinical and Experimental Immunology*, vol. 35, No. 1 (Jan. 1979), pp. 1-9.

Calne, R.Y. et al., "Cyclosporin A in a patients receiving renal allografts from cadaver donors", *The Lancet*, (Dec. 23 & 30, 1978), pp. 1323-1327.

Dreyfuss, M. et al., "Cyclosporin A and C", *European Journal of Applied Microbiology*, vol. 3 (1976), pp. 125-133.

Etzkorn, F. et al., "Cyclophilin Residues That Affect noncompetitive Inhibition of the Protein Serine Phosphatase Activity of Calcineurin by the Cyclophilin-Cyclosporin A Complex", *Biochemistry*, vol. 33 (1994), pp. 2380-2388.

Foster, A.B. et al., "Deuterium Isotope Effects in the Metabolism of Drugs and Xenobiotics: Implications for Drug Design", *Advances in Drug Research*, Academic Press, London, vol. 14 (1985), pp. 2-40.

Gordon, M.Y. et al., "Selective effects of cyclosporine A on colony-forming lymphoid and myeloid cells in man", *Nature*, vol. 279 (May 31, 1979), pp. 433-434.

Lawen, A. et al., "Cell-free biosynthesis of new cyclosporins", *The Journal of Antibiotics*, vol. 42, No. 8 (Aug. 1989), pp. 1283-1289.

Liu, J. et al., "Calcineurin Is a Common Target of Cyclophilin-Cyclosporin A and FKBP-FK506 Complexes", *Cell*, vol. 66 (Aug. 23, 1991), pp. 807-815.

Petcher, T.J. et al., "Crystal and Molecular Structure of an Iodo-derivative of the Cyclic Undecapeptide Cyclosporin A", *Helvetica Chimica Acta*, vol. 50, Fasc. 5 (1976), pp. 1480-1488.

Pflügl, G. et al., "X-ray structure of a decameric cyclophilin-cyclosporin crystal complex" *Nature*, vol. 361 (Jan. 7, 1993), pp. 91-94.

Sokol, R. et al, "Improvement of Cyclosporin absorption in children after liver transplantation by means of water-soluble vitamin E", *The Lancet*, vol. 338 (1991), pp. 212-214.

Traber, R. et al., "Cyclosporins—New Analogues by Precursor Directed Biosynthesis", *The Journal of Antibiotics*, vol. 42, No. 4 (Apr. 1989), pp. 591-597.

Tutschka, P.J. et al., "Cyclosporin-A to Prevent Graft-Versus-Host Disease: A Pilot Study in 22 Patients Receiving Allogeneic Marrow Transplants", *Blood*, vol. 61, No. 2 (Feb. 1983), pp. 318-325.

Von Wartburg, A. et al., "Cyclosporins, Fungal Metabolites with Immunosuppressive Activities", *Progress in Medicinal Chemistry 25*, (1998), pp. 1-33.

White, D.J.G. et al., "Cyclosporin A: An Immunosuppressive Agent Preferentially Active Against Proliferating T Cells", *Transplantation*, vol. 27, No. 1 (1979), pp. 55-58.

* cited by examiner

CYCLOSPORINE ANALOGUE MIXTURES AND THEIR USE AS IMMUNOMODULATING AGENTS

CROSS-REFERENCE TO RELATED APPLICATIONS

This application is a continuation of U.S. application Ser. No. 10/274,255, filed Oct. 17, 2002, now U.S. Pat. No. 6,998,385 which claims the benefit of U.S. application Ser. No. 60/346,201, filed Oct. 19, 2001 and U.S. application Ser. No. 60/370,596, filed April 5, 2002. The disclosure of each of these applications is incorporated herein by reference in its entirety.

FIELD OF THE INVENTION

The invention is directed to isomeric mixtures of cyclosporin analogues that are related to cyclosporine A. It is contemplated that the mixtures possess enhanced efficacy and/or reduced toxicity over the individual isomers and over naturally occurring and other presently known cyclosporines and cyclosporine derivatives. In addition, the present invention relates to synthetic pathways for producing isomers of cyclosporin A analogs, where such pathways vary in the degree of stereoselectivity depending on the specific reaction conditions.

REFERENCES

The following references are related hereto or referred to herein by patent or application number or in parenthesis by author and year at the relevant portions of this specification:

Bennett, W. M., "The nephrotoxicity of new and old immunosuppressive drugs," *Renal Failure*, Vol. 20, pp. 687-90 (1998).

J.-F. Biellmann, J.-B. Ducep in "Allylic and benzylic carbanions substituted by heteroatoms," *Organic Reactions*, Vol. 27 (Wiley, New York, 1982), p. 9.

H. J. Carlseh et al. in "A Greatly Improved Procedure for Ruthenium Tetroxide Catalyzed Oxidations of Organic Compounds," *J. Org. Chem.*, Vol. 46, No. 19, pp 3736-3738 (1981).

T. Chang, L. Z. Benet, M. F. Hebert, "The effect of water-soluble vitamin E on cyclosporine pharmacokinetics in healthy volunteers," *Clin. Pharmacol. Ther.*, Vol. 59, pp. 297-303 (1996).

M. K. Eberle, F. Nuninger, "Synthesis of the main metabolite (OL-17) of cyclosporin A," *J. Org. Chem.*, Vol. 57, pp. 2689-2691 (1992).

E. Ehlinger, P. Magnus in "Silicon in synthesis. 10. The (trimethylsilyl)allyl anion: A β-acyl anion equivalent for the conversion of aldehydes and ketones into γ-lactones," *J. Am. Chem. Soc.*, Vol. 102, No. 15, pp. 5004-5011 (1980).

D. S. Fruman, C. B. Klee, B. E. Bierer, S. J. Burakoff, "Calcineurin phosphatase activity in T lymphocytes is inhibited by FK506 and cyclosporin A," *Proc. Natl. Acad. Sci. USA*, Vol. 89, pp. 3686-90 (1992).

A. Granelli-Piperno, L. Andrus, R. M. Steinman, "Lymphokine and nonlymphokine mRNA levels in stimulated human cells: kinetics, mitogen requirements, and effects of cyclosporin A," *J. Exp. Med.*, Vol. 163, p. 922 (1986).

J. R. Hanson, "The Protection of Alcohols," *Protecting Groups in Organic Synthesis*, Ch. 2, pp. 24-25 (Sheffield Academic Press, Sheffield, England, 1999).

M. F. Hebert, J. P. Roberts, T. Prueksaritanont, L. Z. Benet, "Bioavailability of cyclosporin with concomitant rifampin administration is markedly less than predicted by hepatic enzyme induction," *Clin. Pharmacol. Ther.*, Vol. 52, pp. 453-7 (1992).

R. W. Hoffmann, H.-J Zei, "Stereoselective synthesis of alcohols. 8. Diastereoselective synthesis of β-methylhomoallyl alcohols via crotylboronates," *J. Org. Chem.*, Vol. 46, pp. 1309-1314 (1981).

P. F. Hurdlik and D. Peterson in "Stereospecific Olefin-Forming Elimination Reactions of β-Hydroxysilanes," *J. Am. Chem. Soc.*, Vol. 97, No. 6, pp. 1464-1468 (1975).

Y. Ikeda, J. Ukai, N. Ikeda, H. Yamamoto, "Stereoselective synthesis of (Z)- and (E)-1,3-alkadienes from aldehydes using organotitanium and lithium reagents," *Tetrahedron*, Vol. 43, No. 4, pp. 723-730 (1987).

Kobel et al., Europ. J. Applied Microbiology and Biotechnology, Vol. 14, pp. 237-240 (1982).

M. T. Reetz in Organotitanium Reagents in *Organic Synthesis* (Springer-Verlag, Berlin, 1986), pp. VII, 148-149, and 164-165.

Rich et al., *J. Med. Chem.*, Vol. 29, p. 978 (1986).

J. McMurry, *Organic Chemistry*, $5^{th}$ Ed. (Brooks/Cole, Pacific Grove, 2000), pp. 780-783.

S. L. Schreiber, G. R. Crabtree, "The mechanism of action of cyclosporin A and FK506," *Immunol. Today*, Vol. 13, pp. 136-42 (1992).

I. Sketris, R. Yatscoff, P. Keown, D. M. Canafax, M. R. First, D. W. Holt, T. J. Schroeder, M. Wright, "Optimizing the use of cyclosporine in renal transplantation," *Clin. Biochem.*, Vol.28, pp. 195-211 (1995).

M. B. Smith and J. March, *March's Advanced Organic Chemistry* (Wiley, New York, 2001), pp. 144-147.

A. Streitwieser, C. H. Heathcock, *Introduction to Organic Chemistry*, $2^{nd}$ ed. (Macmillan, New York, 1981), pp. 845-846.

J. A. Thliveris, R. W. Yatscoff, M. P. Lukowski, K. R. Copeland, J. R. Jeffery, G. F. Murphy, "Chronic ciclosporin nephrotoxicity: A rabbit model," *Nephron*. Vol. 57, pp. 470-6 (1991).

J. A. Thliveris, R. W. Yatscoff, M. J. Mihatsch, "Chronic cyclosporine-induced nephrotoxicity: A rabbit model," *Transplantation*, Vol. 57, pp. 774-6 (1994).

S. E. Thomas in *Organic Synthesis: The Roles of Boron and Silicon* (Oxford University Press, New York, 1991), pp. 84-87.

Traber et al., *Helv. Chim. Acta*, Vol. 60, pp. 1247-1255 (1977).

Traber et al., *Helv. Chim. Acta*, Vol. 65, pp. 1655-1667 (1982).

D. S. Tsai, D. S. Matteson, "A stereocontrolled synthesis of (Z) and (E) terminal dienes from pinacol (E)-1-trimethylsilyl-1-propene-3-boronate," *Tetrahedron Letters*, Vol. 22, No. 29, p. 2751-2752 (1981).

H. A. Valantine, J. S. Schroeder, "Recent advances in cardiac transplantation" [editorial; comment], *N. Engl. J. Med.*, Vol. 333, No. 10, pp. 660-1 (1995).

von Wartburg et al., *Progress in Allergy*, Vol. 38, pp. 28-45 (1986).

Wenger, *Transpl. Proc.*, Vol. 15, Suppl. 1, p. 2230 (1983).

Wenger, *Angew. Chem. Int. Ed.*, Vol. 24, p. 77 (1985).

Wenger, Progress in the Chemistry of Organic Natural Products, Vol. 50, p. 123 (1986).

U.S. Pat. No. 4,108,985.
U.S. Pat. No. 4,160,452.
U.S. Pat. No. 4,210,581.
U.S. Pat. No. 4,220,641.
U.S. Pat. No. 4,256,108.
U.S. Pat. No. 4,265,874.

U.S. Pat. No. 4,288,431.
U.S. Pat. No. 4,384,996.
U.S. Pat. No. 4,396,542.
U.S. Pat. No. 4,554,351.
U.S. Pat. No. 4,771,122.
U.S. Pat. No. 5,284,826.
U.S. Pat. No. 5,525,590.
European Patent Publication No. 0 034 567.
European Patent Publication No. 0 056 782.
International Patent Publication No. WO 86/02080.
International Patent Publication No. WO 99/18120.

The disclosure of each of the above-referenced patents, patent applications and publications is incorporated herein by reference in its entirety.

BACKGROUND OF THE INVENTION

Cyclosporine derivatives compose a class of cyclic polypeptides, consisting of eleven amino acids, that are produced as secondary metabolites by the fungus species *Tolypocladium inflatum Gams*. They have been observed to reversibly inhibit immunocompetent lymphocytes, particularly T-lymphocytes, in the $G_0$ or $G_1$ phase of the cell cycle. Cyclosporine derivatives have also been observed to reversibly inhibit the production and release of lymphokines (Granelli-Piperno et al., 1986). Although a number of cyclosporine derivatives are known, cyclosporine A is the most widely used. The suppressive effects of cyclosporine A are related to the inhibition of T-cell mediated activation events. This suppression is accomplished by the binding of cyclosporine to the ubiquitous intracellular protein, cyclophilin. This complex, in turn, inhibits the calcium- and calmodulin-dependent serine-threonine phosphatase activity of the enzyme calcineurin. Inhibition of calcineurin prevents the activation of transcription factors such as $NFAT_{p/c}$ and NF-κB, which are necessary for the induction of the cytokine genes (IL-2, IFN-γ, IL-4, and GM-CSF) during T-cell activation. Cyclosporine also inhibits lymphokine production by T-helper cells in vitro and arrests the development of mature CD8 and CD4 cells in the thymus (Granelli-Piperno et al., 1986). Other in vitro properties of cyclosporine include the inhibition of IL-2 producing T-lymphocytes and cytotoxic T-lymphocytes, inhibition of IL-2 released by activated T-cells, inhibition of resting T-lymphocytes in response to alloantigen and exogenous lymphokine, inhibition of IL-1 production, and inhibition of mitogen activation of IL-2 producing T-lymphocytes (Granelli-Piperno et al., 1986).

Cyclosporine is a potent immunosuppressive agent that has been demonstrated to suppress humoral immunity and cell-mediated immune reactions such as allograft rejection, delayed hypersensitivity, experimental allergic encephalomyelitis, Freund's adjuvant arthritis and graft vs. host disease. It is used for the prophylaxis of organ rejection subsequent to organ transplantation; for treatment of rheumatoid arthritis; for the treatment of psoriasis; and for the treatment of other autoimmune diseases, including type I diabetes, Crohn's disease, lupus, and the like.

Since the original discovery of cyclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [c.f. Traber et al. (1977); Traber et al. (1982); Kobel et al. (1982); and von Wartburg et al. (1986)], as well as various non-natural cyclosporin derivatives and artificial or synthetic cyclosporins including the dihydro- and iso-cyclosporins; derivatized cyclosporins (e.g., in which the 3'-O-atom of the -MeBmt-residue is acylated or a further substituent is introduced at the α-carbon atom of the sarcosyl residue at the 3-position); cyclosporins in which the -MeBmt-residue is present in isomeric form (e.g., in which the configuration across positions 6' and 7' of the -MeBmt-residue is cis rather than trans); and cyclosporins wherein variant amino acids are incorporated at specific positions within the peptide sequence employing, e.g., the total synthetic method for the production of cyclosporins developed by R. Wenger—see e.g. Traber et al. (1977), Traber et al. (1982) and Kobel et al. (1982); U.S. Pat. Nos. 4,108,985, 4,210,581, 4,220,641, 4,288,431, 4,554,351 and 4,396,542; European Patent Publications Nos. 0 034 567 and 0 056 782; International Patent Publication No. WO 86/02080; Wenger (1983); Wenger (1985); and Wenger (1986). Cyclosporin A analogues containing modified amino acids in the 1-position are reported by Rich et al. (1986). Immunosuppressive, anti-inflammatory, and anti-parasitic cyclosporin A analogues are described in U.S. Pat. Nos. 4,384,996; 4,771,122; 5,284,826; and 5,525,590, all assigned to Sandoz. Additional cyclosporin analogues are disclosed in WO 99/18120, assigned to Isotechnika. The terms Ciclosporin, ciclosporin, cyclosporine, and Cyclosporine are interchangeable and refer to cyclosporin.

There are numerous adverse effects associated with cyclosporine A therapy, including nephrotoxicity, hepatotoxicity, cataractogenesis, hirsutism, parathesis, and gingival hyperplasia to name a few (Sketris et al., 1995). Of these, nephrotoxicity is one of the more serious, dose-related adverse effects resulting from cyclosporine A administration. Immediate-release cyclosporine A drug products (e.g., Neoral® and Sandimmune®) can cause nephrotoxicities and other toxic side effects due to their rapid release and the absorption of high blood concentrations of the drug. It is postulated that the peak concentrations of the drug are associated with the side effects (Bennett, 1998). The exact mechanism by which cyclosporine A causes renal injury is not known; however, it is proposed that an increase in the levels of vasoconstrictive substances in the kidney leads to the vasoconstriction of the afferent glomerular arterioles. This can result in renal ischemia, a decrease in glomerular filtration rate and, over the long term, interstitial fibrosis. When the dose is reduced or another immunosuppressive agent is substituted, renal function improves (Valantine and Schroeder, 1995).

Accordingly, there is a need for immunosuppressive agents which are effective and have reduced toxicity.

Cyclosporin analogs containing modified amino acids in the 1-position are disclosed in WO 99/18120, which is assigned to the assignee of the present application, and incorporated herein in its entirety. Also assigned to the present assignee is U.S. Provisional Patent Application No. 60/346,201, in which applicants disclosed a particularly preferred cyclosporin A analog referred to as "$ISA_{TX}247$." This analog is structurally identical to cyclosporin A except for modification at the 1-amino acid residue. Applicants discovered that certain mixtures of cis and trans isomers of $ISA_{TX}247$ exhibited a combination of enhanced potency, and/or reduced toxicity over the naturally occurring and presently known cyclosporins. Certain alkylated, arylated, and deuterated derivatives of $ISA_{TX}247$ were also disclosed.

Typically, the disclosed mixtures in U.S. Provisional Patent Application No. 60/346,201 range from about 10 to 90 percent by weight of the trans-isomer and about 90 to 10 percent by weight of the cis-isomer; in another embodiment, the mixture contains about 15 to 85 percent by weight of the trans-isomer and about 85 to 15 percent of the cis-isomer; in another embodiment, the mixture contains about 25 to 75 percent by weight of the trans-isomer and about 75 to 25 percent by weight of the cis-isomer; in another embodiment, the mixture contains about 35 to 65 percent by weight of the trans-isomer and about 65 to 35 percent by weight of the cis-isomer; in another embodiment, the mixture contains about 45 to 55 percent by weight of the trans-isomer and about 55 to 45 percent of the cis-isomer. In another embodiment, the isomeric mixture is an ISA$_{TX}$247 mixture which comprises about 45 to 50 percent by weight of the trans-isomer and about 50 to 55 percent by weight of the cis-isomer. These percentages by weight are based on the total weight of the composition. In other words, a mixture might contain 65 percent by weight of the (E)-isomer and 35 percent by weight of the (Z)-isomer, or vice versa. In an alternate nomenclature, the cis-isomer may also be described as a (Z)-isomer, and the trans-isomer could also be called an (E)-isomer.

Accordingly, there is a need in the art for methods of preparation of cyclosporin analogs, including isomers of ISA$_{TX}$247. Synthetic pathways are needed that produce enriched compositions of the individual isomers, as well as mixtures of the isomers having a desired ratio of the two isomers. Methods of preparation of derivatives of ISA$_{TX}$247 are needed as well.

SUMMARY OF THE INVENTION

Cyclosporine and its analogs are members of a class of cyclic polypeptides having potent immunosuppressant activity. Despite the advantages these drugs offer with respect to their immunosuppressive, anti-inflammatory, and anti-parasitic activities, there are numerous adverse effects associated with cyclosporine A therapy that include nephrotoxicity and hepatotoxicity. Accordingly, there is a need for new immunosuppressive agents that retain pharmacological activity as the naturally occurring compound cyclosporin A, but without one or more of the associated toxic side effects.

Embodiments of the present invention provide certain mixtures of cis and trans-isomers of cyclosporin A analogs, which are pharmaceutically useful. A preferred analog is referred to as ISA$_{TX}$247. Mixtures of ISA$_{TX}$247 isomers exhibit a combination of enhanced potency and reduced toxicity over the naturally occurring and presently known cyclosporins.

The present invention is based, in part, on the discovery that certain isomeric mixtures of analogues of cyclosporine provide superior immunosuppressive effects without one or more of the adverse effects associated with cyclosporine A. In particular, we have unexpectedly found that isomeric mixtures (i.e., mixtures of both cis- and trans-isomers) ranging from about 10:90 to about 90:10 (trans- to cis-) of cyclosporine analogues modified at the 1-amino acid residue provide superior efficacy and safety. Examples of such analogues are disclosed in WO 99/18120, and include deuterated and non-deuterated compounds. In particular, mixtures in the range of about 45:55 to about 50:50 (trans- to cis-) and in the range of about 50% to about 55% trans- and about 45% to about 50% cis- are found to be particularly efficacious. Moreover, it has been demonstrated that these isomer mixtures exhibit a combination of superior potency and reduced toxicity over naturally occurring and other presently known cyclosporines and cyclosporine derivatives.

A particularly preferred analogue (referred to herein as "ISA$_{TX}$247") is structurally similar to cyclosporine A except for a modified functional group on the periphery of the molecule, at the 1-amino acid residue. The structure of this particular isomeric analogue mixture compared to the structure of cyclosporine A is:

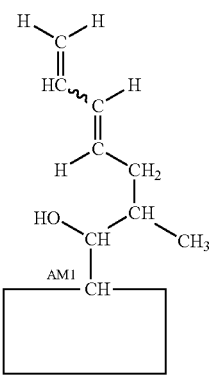

ISA$_{TX}$247

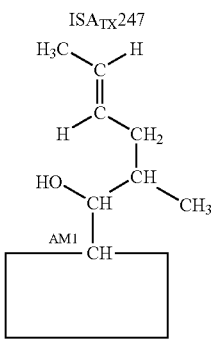

CYCLOSPORIN

The isomeric mixtures can be used, among other things, for immunosuppression, and the care of various immune disorders, diseases and conditions, including the prevention, control, alleviation and treatment thereof.

According to embodiments of the present invention, ISA$_{TX}$247 isomers (and derivatives thereof) are synthesized by stereoselective pathways that may vary in their degree of selectivity. Stereoselective pathways produce compositions that are enriched in either of the (E) and (Z)-isomers, and these compositions may be combined such that the resulting mixture has a desired ratio of the two isomers. Alternatively, the reactions conditions of a stereoselective pathway may be tailored to produce the desired ratio directly in a prepared mixture. The percentage of one isomer or another in a mixture can be verified using nuclear magnetic resonance spectroscopy (NMR) or other techniques well known in the art.

Each of the pathways typically proceeds with the application of a protecting group to a sensitive alcohol functional group. In one embodiment the alcohol is protected as an acetate; in other embodiments the protecting groups are benzoate esters or silyl ethers. Although acetate protecting groups are common in the art, it is important to emphasize that in many of the exemplary embodiments described herein certain undesirable side-reactions involving an acetate protecting group may be avoided through the use of protecting groups such as benzoate esters or silyl ethers.

The protected compound may then serve as a precursor for a variety of stereoselective synthetic pathways including some that utilize phosphorus-containing reagents as participants in a Wittig reaction, and inorganic elements as members of organometallic reagents. The latter type may proceed through six-membered ring transition states where steric hindrance dictates the configurational outcome. Many organometallic reagents are available, including those that feature inorganic elements such as boron, silicon, titanium, lithium, and sulfur. Individual isomers may be prepared from single or multiple precursors.

The ratio of the (E) to (Z)-isomers in any mixture, whether produced stereoselectively or non-stereoselectively, may take on a broad range of values. For example, the mixture may comprise from about 10 to 90 percent of the (E)-isomer to about 90 to 10 percent of the (Z)-isomer. In other embodiments, the mixture may contain from about 15 to 85 percent by weight of the (E)-isomer and about 85 to 15 percent of the (Z)-isomer; in another embodiment, the mixture contains about 25 to 75 percent by weight of the (E)-isomer and about 75 to 25 percent by weight of the (Z)-isomer; in another embodiment, the mixture contains about 35 to 65 percent by weight of the (E)-isomer and about 65 to 35 percent by weight of the (Z)-isomer; in another embodiment, the mixture contains about 45 to 55 percent by weight of the (E)-isomer and about 55 to 45 percent of the (Z)-isomer. In another embodiment, the isomeric mixture is an $ISA_{TX}247$ mixture which comprises about 45 to 50 percent by weight of the (E)-isomer and about 50 to 55 percent by weight of the (Z)-isomer. These percentages by weight are based on the total weight of the composition, and it will be understood that the sum of the weight percent of the (E)-isomer and the (Z)-isomer is 100 weight percent. In other words, a mixture might contain 65 percent by weight of the (E)-isomer and 35 percent by weight of the (Z)-isomer, or vice versa.

In one aspect, the invention is directed to a composition comprising an isomeric mixture of a cyclosporine analogue modified at the 1-amino acid residue, wherein the range of the isomeric mixture is from about 10:90 to about 90:10 (trans- to cis). A preferred composition (referred to herein as "$ISA_{TX}247$") comprises an isomeric mixture of isomers E- and Z-:

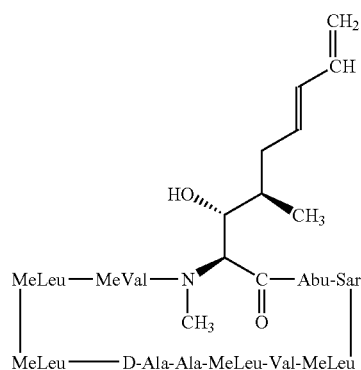

E-isomer

-continued

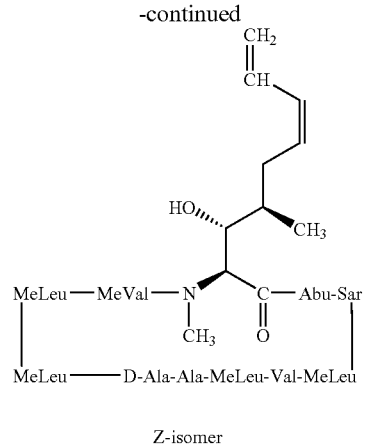

Z-isomer

Typically, the isomeric mixture comprises about 10% to about 90% of the E-isomer and about 90% to about 10% of the Z-isomer; preferably, the mixture contains about 15% to about 85% of the E-isomer and about 85% to about 15% of the Z-isomer; more preferably the mixture contains about 25% to about 75% of the E-isomer and about 75% to about 25% of the Z-isomer; even more preferably the mixture contains about 35% to about 65% of the E-isomer and about 65% to about 35% of the Z-isomer; yet even more preferably the mixture contains about 45% to about 55% of the E-isomer and about 55% to about 45% of the Z-isomer. In most preferred embodiments, the isomeric mixture may be $ISA_{TX}247$ mixtures which comprise: about 45 to about 50% of the E-isomer and about 55 to 50% of the Z-isomer; about 50% to about 55% of the E-isomer and about 45% to about 50% of the Z-isomer; about 55% to about 65% of the E-isomer and about 35% to about 45% of the Z-isomer; about 65% to about 75% of the E-isomer and about 25% to about 35% of the Z-isomer; about 75% to about 85% of the E-isomer and about 15% to about 25% of the Z-isomer; about 85% to about 90% of the E-isomer and about 10% to about 15% of the Z-isomer. Further preferred isomeric mixtures comprise those of about 75% to about 65% Z-isomer and about 25% to about 35% E-isomer, and of about 65% to about 55% Z-isomer and about 35% to about 25% E-isomer. (The percentages are on a weight basis.)

In another aspect, the invention is directed to pharmaceutical compositions comprising an isomeric cyclosporine analogue mixture as described above and a pharmaceutically acceptable excipient. The isomeric analogue mixture is preferably an $ISA_{TX}247$ mixture.

In a further aspect, the invention is directed to a method of producing immunosuppression comprising administering to an animal in need thereof, an effective amount of an isomeric cyclosporine analogue mixture as described above or a composition comprising the isomeric analogue mixture. In a preferred embodiment, the mixture is an $ISA_{TX}247$ mixture. The method may be used to treat or alleviate transplant rejection, an autoimmune disease or condition, or an inflammatory disease or condition.

In yet a further aspect, the invention is directed to a method of reducing the toxicity of an immunosuppressive cyclosporine analogue by preparing an isomeric mixture of the analogue for use as the immunosuppressive agent. In a preferred embodiment, the mixture is an $ISA_{TX}247$ mixture.

In a still further aspect, the invention is directed to a method of increasing the efficacy of an immunosuppressive cyclosporine analogue by preparing an isomeric mixture of the analogue for use as the immunosuppressive agent. In a preferred embodiment, the mixture is an $ISA_{TX}247$ mixture.

In yet a further still aspect, methods for the synthesis of isomeric analogue mixtures are provided.

DETAILED DESCRIPTION OF THE INVENTION

Synthesis

Cyclosporin and its analogs are members of a class of cyclic polypeptides having potent immunosuppressive activity. Despite the advantages these drugs offer with respect to their immunosuppressive, anti-inflammatory, and anti-parasitic activities, there are numerous adverse effects associated with cyclosporine A therapy that include nephrotoxicity and hepatotoxicity. Accordingly, there is a need for new immunosuppressive agents that are as pharmacologically active as the naturally occurring compound cyclosporin A, but without the associated toxic side effects.

Applicants have previously disclosed a cyclosporin A analog referred to as "$ISA_{TX}247$." This analog is structurally similar to cyclosporin A except for modification at the 1-amino acid residue. Applicants discovered that certain mixtures of cis and trans-isomers of $ISA_{TX}247$ exhibited a combination of enhanced potency, and reduced toxicity, over the naturally occurring and presently known cyclosporins.

According to embodiments of the present invention, $ISA_{TX}247$ isomers (and derivatives thereof) are synthesized by stereoselective pathways that may vary in their degree of stereoselectivity. Stereoselective pathways produce compositions that are enriched in either of the (E) and (Z)-isomers, and these compositions may be combined such that the resulting mixture has a desired ratio of the two isomers. Alternatively, the reaction conditions of a stereoselective pathway may be tailored to produce the desired ratio directly in a prepared mixture.

The chemical name of one immunosuppressive cyclosporin analog of the present invention, called $ISA_{TX}247$, is chemically described by the name cyclo {{E, Z)-(2S,3R,4R)-3-hydroxy-4-methyl-2-(methylamino)-6,8-nonadienoyl}-L-2-aminobutyryl-N-methyl-glycyl-N-methyl-L-Leucyl-L-valyl-N-methyl-L-leucyl-L-alanyl-D-alanyl-N-methyl-L-leucyl-N-methyl-L-leucyl-N -methyl-L-valyl}. Its empirical formula is $C_{63}H_{11}N_{11}O_{12}$, and it has a molecular weight of about 1214.85. The term "$ISA_{TX}247$" is a trade designation given to this pharmacologically active compound.

The structure of $ISA_{TX}247$ has been verified primarily through nuclear magnetic resonance (NMR) spectroscopy. Both the $^1H$ and $^{13}C$ spectra were assigned using a series of one and two dimensional NMR experiments, and by comparison to the known NMR assignments for cyclosporin A. The absolute assignment of the (E) and (Z)-isomers of $ISA_{TX}247$ was confirmed by Nuclear Overhauser Effect (NOE) experiments. Additional supporting evidence was provided by mass spectral analysis, which confirmed the molecular weight, and by the infrared spectrum, which was found to be very similar to cyclosporin A. The latter result was expected, given the similarity between the two compounds.

Figure 1A:
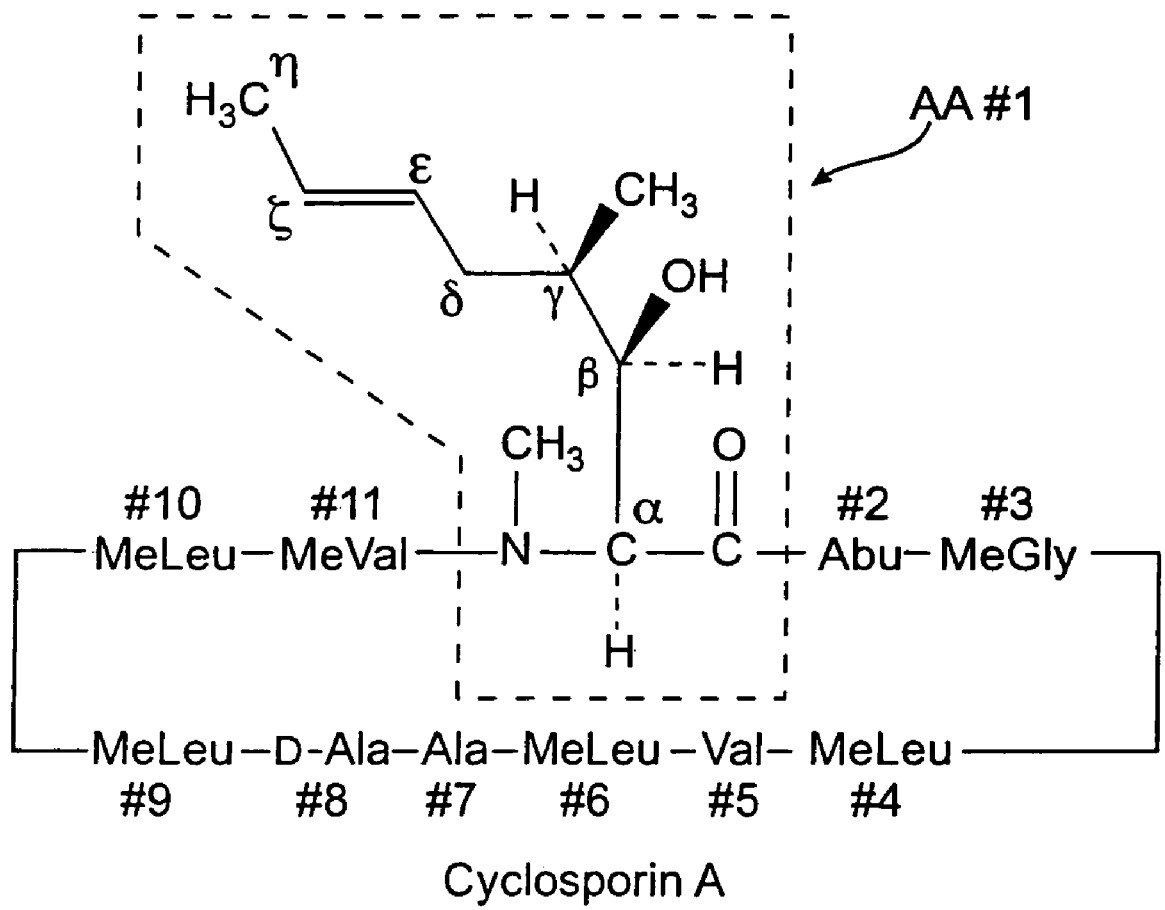
FIG. 1A shows the structure of cyclosporin A, illustrating the 11 amino acid residues that comprise the cyclic peptide ring of the molecule, as well as the structure of the side chain of the 1-amino acid residue.

The structure of cyclosporin A is illustrated in FIG. 1A. The structure includes identification of the 11 amino acid residues that comprise the cyclic peptide ring of the molecule. These 11 amino acid residues are labeled with numbers increasing in a clockwise direction, starting with the amino acid shown at the top center of the ring (and identified with reference label "1-amino acid"). The first amino acid is enclosed in a dashed box for clarity. The side chain of the 1-amino acid residue has been drawn out chemically since it is at this general location that the synthetic reactions described herein take place. Conventionally, the carbon adjacent to the carbonyl group of an amino acid is labeled as the α-carbon, with progressive letters in the Greek alphabet used to label adjacent carbons in a direction down the chain, away from the peptide ring. In the case of cyclosporin A, as shown in FIG. 1A, the β-carbon of the side chain is bonded to a hydroxyl group, and there is a trans-oriented double bond between the ε and ζ-carbons of the side chain.

Figure 1B:
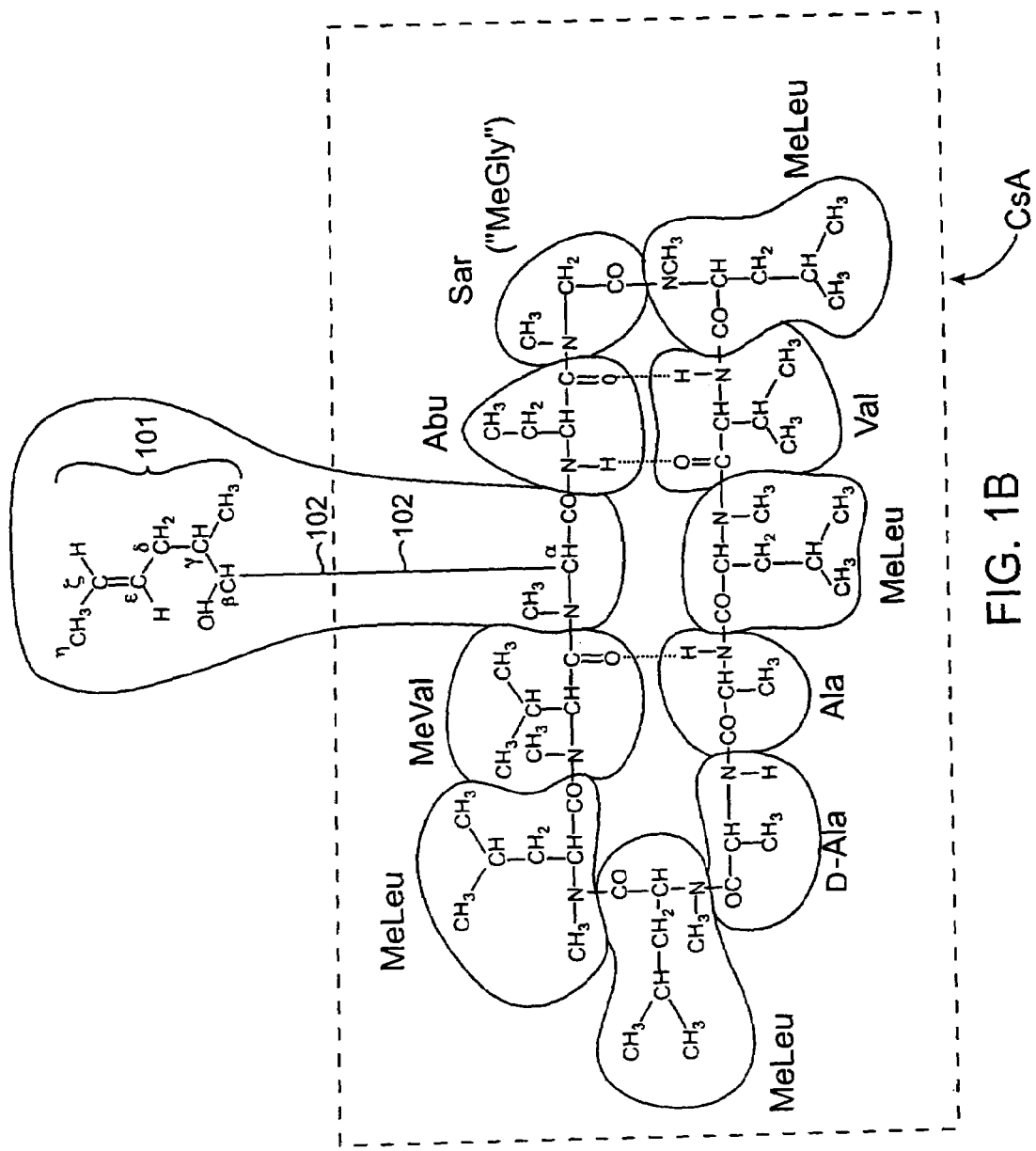
FIG. 1B is another illustration of the structure of cyclosporin A with particular emphasis on the definition of the term "CsA" as it is used in the present description.

Another schematic of the cyclosporin A structure is drawn in FIG. 1B, where a different portion of the molecule has been enclosed in a dashed box. This figure defines the nomenclature to be used in the present description, where the term "CsA" refers to the portion of the cyclosporin A enclosed in the box. The present nomenclature provides a shorthand means of displaying the region where the synthetic reactions described herein will take place (i.e., the side chain of the 1-amino acid residue, which has been drawn outside the dashed box in FIG. 1B), without having to re-draw the remainder of the molecule each time a reaction is described. It will be obvious to those skilled in the art that the bond between the α and β-carbons of the side chain is of normal length, and has been exaggerated only in this drawing to assist with the definition of the term "CsA."

Figure 2A:
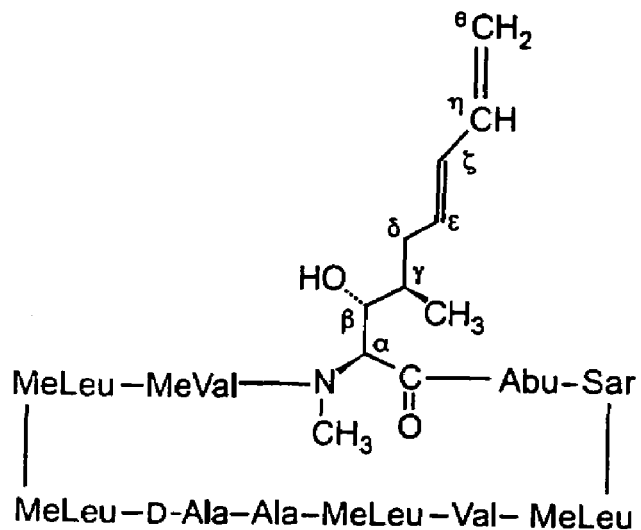
FIG. 2A shows the structure of the E-isomer (or trans-isomer) of the cyclosporin A analog called $ISA_{TX}247$.
Figure 2B:
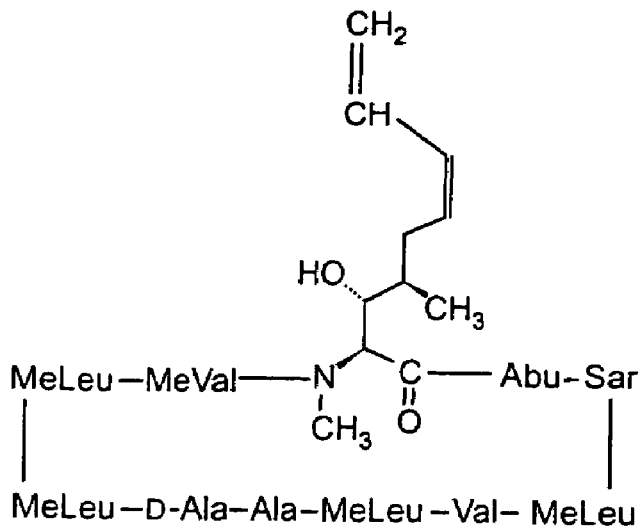
FIG. 2B shows the structure of the Z-isomer (or cis-isomer) of the cyclosporin A analog $ISA_{TX}247$.

As stated above, a particularly preferred cyclosporin A analog is called ISA$_{TX}$247, and its two stereoisomers E (or trans) and Z (or cis) are shown in FIGS. 2A and 2B, respectively. The cis or trans nature of these stereoisomers refers to the configuration of the double bond between the ε and ζ-carbons of the side chain; i.e., the double bond nearer to the peptide ring, as opposed to the double bond at the terminal end of the chain.

A word should be said about stereochemical nomenclature. In the present description the terms cis and (Z) will be used interchangeably, and the terms trans and (E) will be used interchangeably. Usage of the terms "erythro" and "threo" will be kept to a minimum due to apparent confusion in the literature with regard to their meaning. See R. W. Hoffmann and H.-J Zei in "Stereoselective synthesis of Alcohols. 8. Diastereoselective Synthesis of β-Methylhomoallyl Alcohols via Crotylboronates," *J. Org. Chem.*, Vol. 46, pp. 1309-1314 (1981); A. Streitwieser and C. H. Heathcock, *Introduction to Organic Chemistry*, 2$^{nd}$ ed. (Macmillan, New York, 1981), pp. 845-846; and M. B. Smith and J. March, *March's Advanced Organic Chemistry* (Wiley, New York, 2001), pp. 144-147. In the few cases where threo/erythro terminology is employed herein the convention of Streitwieser and Heathcock is used, where "erythro" isomers refer to (R,S) and (S,R) configurations, and "threo" isomers refer to (R,R) and (S,S) configurations.

A final comment about nomenclature concerns the terminal carbon-carbon double bond shown in FIGS. 2A and 2B. In an alternate numbering scheme, the carbons in the side chain of the 1-amino acid residue may be numbered starting with the terminal (θ) carbon, and working back toward the peptide ring. In this system the ISA$_{TX}$247 isomers may be thought of as 1,3-dienes according to conventional nomenclature in organic chemistry, where each double bond is identified by its lowest numbered carbon.

The synthetic pathways illustrated in FIGS. 3-8 will now be discussed. According to embodiments of the present invention, isomeric mixtures may be prepared directly, wherein the reaction conditions of a particular synthetic pathway are tailored to achieve the desired ratio of isomers in the mixture. Alternatively, compositions may be prepared that are enriched in one of the two geometrical isomers of a cyclosporin A analog, and the compositions combined in a predefined ratio to achieve the desired mixture.

Figure 3:
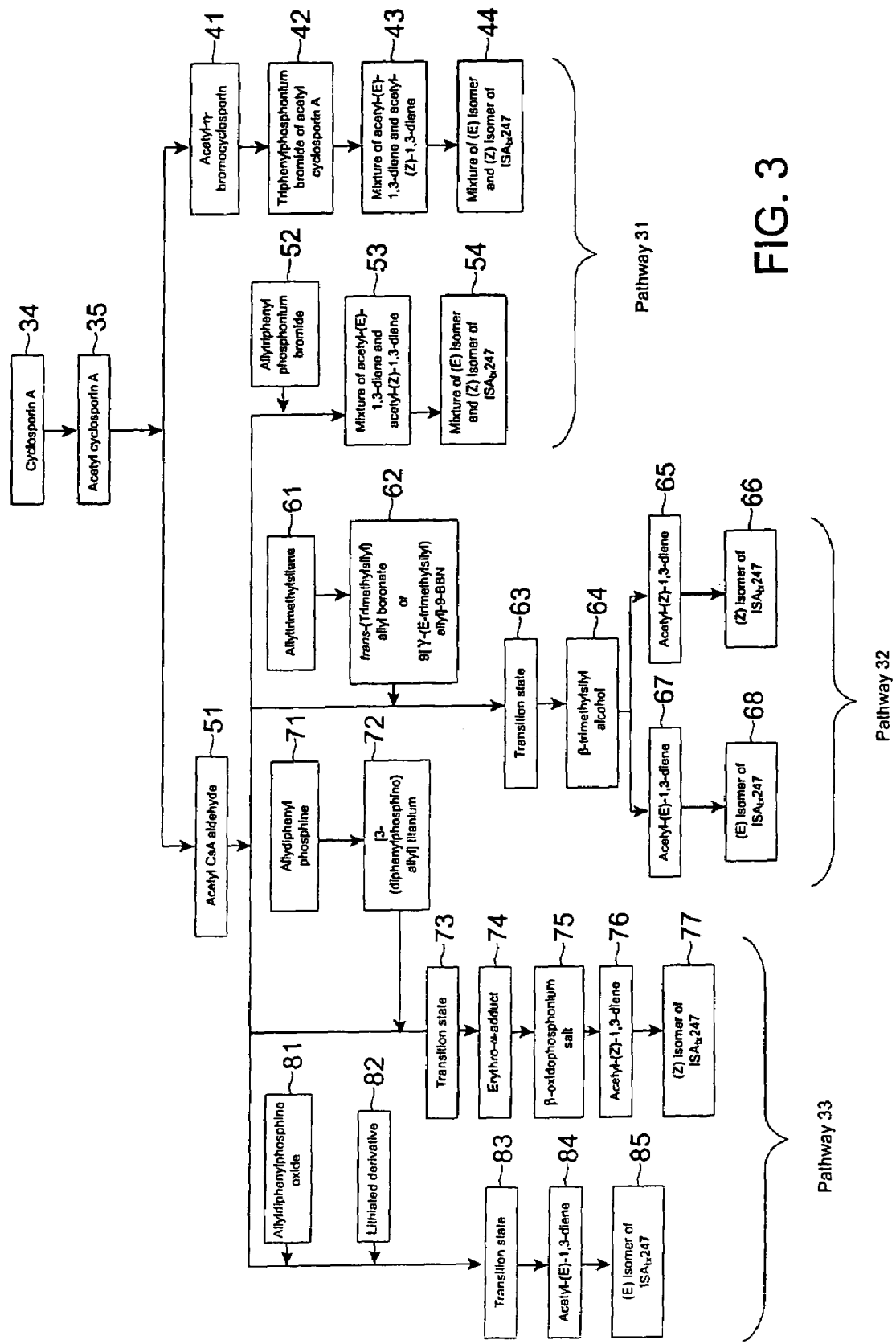
FIG. 3 shows an overview of exemplary synthetic pathways that may be used to prepare the cyclosporin analogs of the present invention, where stereoselective pathways are grouped according to reactive conditions.

An overview of the synthetic pathways according to embodiments of the present invention is given in FIG. 3, where particular emphasis is given to grouping reaction paths according to chemistry and stereoselectivity. Referring to FIG. 3, synthetic pathways that utilize Wittig reactions are shown generally on the right-hand side of the diagram as indicated by reference numeral 31, while pathways 32 and 33 that utilize organometallic reagents that are thought to form six-membered ring transition states are shown in the middle and left-hand sides of the diagram. Any of the synthetic pathways may yield a mixture of the isomers, or they may produce compositions enriched in one of the two isomers.

Embodiments of the present invention provide a variety of ways to arrive at the desired mixture of isomers. The flexibility and versatility of the synthetic strategies disclosed herein may be reflected in part by the symmetries and asymmetries of FIG. 3. A reaction that is common to each of the pathways is the protection of a functional group in cyclosporin A 34; in this exemplary embodiment that reaction is the conversion of cyclosporin A 34 to acetyl cyclosporin A 35. An asymmetry in FIG. 3 is the use of acetyl cyclosporin A aldehyde compound 51 as a precursor for all of the titanium and lithium organometallic reagent pathways, but only some of the phosphorus containing Wittig reaction pathways.

In general, synthetic pathways of FIG. 3 whose reaction conditions may be tuned to produce a mixture having the desired ratio of isomers utilize phosphorus-containing reagents as participants in a Wittig reaction. Other stereoselective pathways make use of inorganic elements as well, typically as members of organometallic reagents that proceed through six-membered ring transition states where steric hindrance dictates the configurational outcome. A plethora of organometallic reagents are useful to the present invention, including those that feature inorganic elements such as boron, silicon, titanium, lithium, and sulfur.

Compositions enriched in one or the other of a pair of isomers may be prepared from a single precursor; alternatively, the two compositions may be prepared from different precursors. In one of the stereoselective pathways of FIG. 3 (pathway 32), a single precursor leads to both of the two isomers of ISA$_{TX}$247, depending on the reaction conditions that are chosen. In another of the stereoselective pathways (pathway 33), two different precursors are needed to produce each of the enriched compositions.

The reactions of FIG. 3 will now be discussed in detail. A reaction that is common to each of the pathways is the protection of the alcohol at the β-position of the side chain of the 1-amino acid residue. Such a protection scheme addresses a problem commonly encountered in organic synthesis, where a first functional group is inadvertently modified by a reaction intended for a second (similar and/or identical) functional group located elsewhere on the molecule. To carry out the scheme the first functional group is reacted with a protecting group, the desired reaction is carried out on the second functional group, and the protecting group is then removed from the first functional group.

Protecting groups are well known in organic synthesis, and have been discussed by J. R. Hanson in Chapter 2, "The Protection of Alcohols," of the publication *Protecting Groups in Organic Synthesis* (Sheffield Academic Press, Sheffield, England, 1999), pp. 24-25. Hanson teaches how to protect hydroxyl groups by converting them to either esters or ethers. Acetate esters are perhaps the most frequently used type of chemistry for protecting hydroxyl groups. There are a wide range of conditions that may be used to introduce the acetate group. These reagents and solvents include acetic anhydride and pyridine; acetic anhydride, pyridine and dimethylaminopyridine (DMAP); acetic anhydride and sodium acetate; acetic anhydride and toluene-p-sulfonic acid, acetyl chloride, pyridine and DIAP; and ketene. DMAP is a useful acylation catalyst because of the formation of a highly reactive N-acylpyridinium salt from the anhydride.

In one embodiment of the present invention, the β-alcohol of cyclosporin A 34 is protected as an acetate by reacting 34 with acetyl chloride, ethyl acetate, or combinations thereof, forming the compound acetyl cyclosporin A 35. In another embodiment, the β-alcohol undergoes a nucleophilic addition to acetic anhydride, forming acetyl cyclosporin A 35 and acetic acid. These reactions may be carried out in the presence of dimethylaminopyridine (DMAP) where an excess of acetic anhydride acts as the solvent. In these cases the prefix "acetyl" may be used in the nomenclature throughout the synthetic pathway, or until the acetyl group is removed. For example, the last intermediate in one pathway having an acetyl group at the β-carbon is called "acetyl-(E)-1,3-diene."

Although the preparation of acetyl cyclosporin A is well established in the literature, it will be appreciated by those skilled in the art that protecting groups other than acetate esters may be used to protect the β-alcohol of the 1-amino acid residue of cyclosporin A 34. These protecting groups may include benzoate esters, substituted benzoate esters, ethers, and silyl ethers. Under certain reaction conditions, the acetate protecting group is prone to undesirable side reactions such as elimination and hydrolysis. Since benzoate esters, ethers and silyl ethers are often more resistant to such side reactions under those same reaction conditions, it is often advantageous to employ such protecting groups in place of acetate. Cyclosporin or cyclosporin derivatives which have been protected by an acetyl group or any other protecting group are referred to as "protected-cyclosporin A." Likewise, the ultimate intermediate in the exemplary pathway referred to above would be called "protected-(E)-1,3-diene" instead of "acetyl-(E)-1,3-diene." The nature of the chosen protecting group may have an influence on the desired course of further steps in the reaction sequences.

Referring to FIG. 3, acetyl cyclosporin A 35 has in this exemplary pathway a protected β-alcohol, and this compound serves as a precursor for the synthesis of $ISA_{TX}247$ isomers in several of the synthetic pathways. Wittig reaction pathways will be discussed first.

Synthesis of Mixtures of the (E) and (Z)-isomers of $ISA_{TX}247$ via the Wittig Reaction Wittig reaction pathways exemplified herein are identified by the reference numeral 31 in FIG. 3. Method 1 proceeds through the bromine intermediate acetyl-η-bromocyclosporin 41, whereas method 2 utilizes the acetyl cyclosporin A aldehyde 51 as a starting point. The exemplary methods described below utilize a Wittig reaction to introduce an alkene functionality with a mixture of stereochemical configurations.

The Wittig reactions used in the exemplary embodiments disclosed herein to synthesize mixtures of the (E) and (Z)-isomers of $ISA_{TX}247$ may optionally be carried out in the presence of a lithium halide. The presence of lithium halides in Wittig reactions is well known to have an effect on the ratio of geometrical isomers produced and, therefore, the addition of such a compound can aid in producing a desired mixture of the (E) and (Z)-isomers of $ISA_{TX}247$.

Method 1

Figure 4:
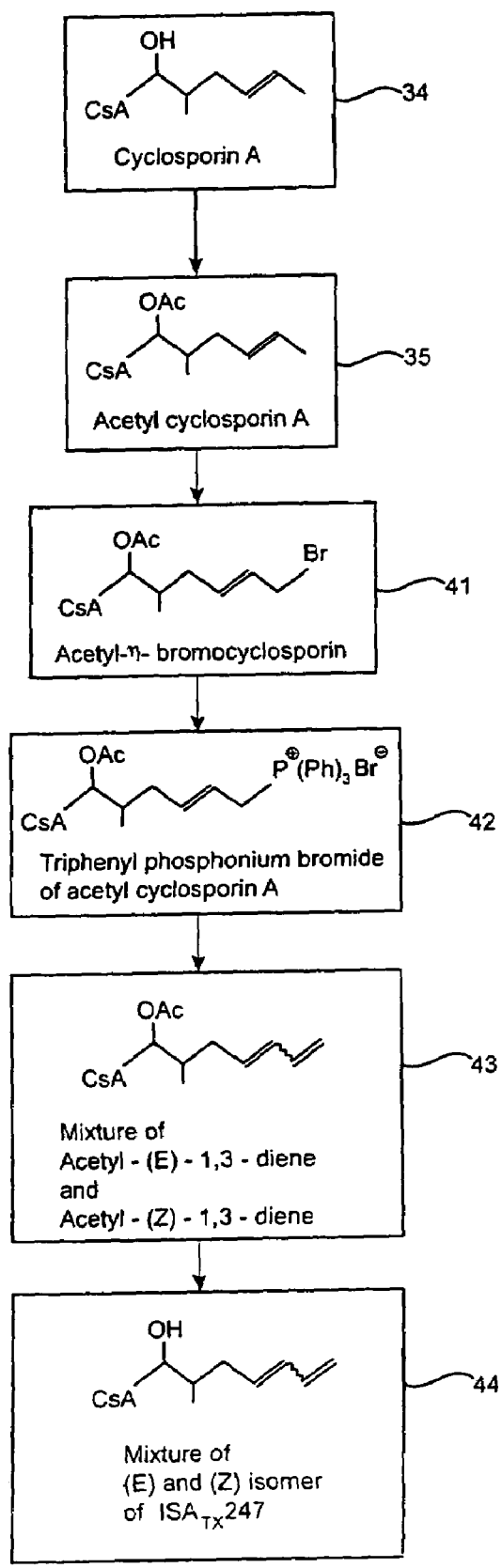
FIG. 4 illustrates a synthetic pathway that produces a mixture of (E) and (Z)-isomers of $ISA_{TX}247$ from a bromine precursor.

In one embodiment of the present invention, a mixture of (E) and (Z)-isomers of $ISA_{TX}247$ is prepared as shown in FIG. 4. The use of the wavy-lined representation in FIG. 4 (see especially compounds 43 and 44) is meant to denote that the exemplary reaction sequence produces a mixture of (E) and (Z)-isomers. In one embodiment the percentage ratio of the (E) to (Z)-isomers produced ranges from about 10 to 90 percent of the (E)-isomer to about 90 to 10 percent of the (Z)-isomer, but these ranges are only exemplary, and many other ranges are possible. For example, the mixture may contain from about 15 to 85 percent by weight of the (E)-isomer and about 85 to 15 percent of the (Z)-isomer. In other embodiments, the mixture contains about 25 to 75 percent by weight of the (E)-isomer and about 75 to 25 percent by weight of the (Z)-isomer; about 35 to 65 percent by weight of the (E)-isomer and about 65 to 35 percent by weight of the (Z)-isomer; and about 45 to 55 percent by weight of the (E)-isomer and about 55 to 45 percent of the (Z)-isomer. In still another embodiment, the isomeric mixture is an $ISA_{TX}247$ mixture which comprises about 45 to 50 percent by weight of the (E)-isomer and about 50 to 55 percent by weight of the (Z)-isomer. These percentages by weight are based on the total weight of the composition, and it will be understood that the sum of the weight percent of the (E) isomer and the (Z) isomer is 100 weight percent. In other words, a mixture might contain 65 percent by weight of the (E)-isomer and 35 percent by weight of the (Z)-isomer, or vice versa.

Referring to FIG. 4, the terminal Ti-carbon of the side chain of the 1-amino acid residue of acetyl-cyclosporin A is brominated in the next step of the reaction by refluxing acetyl cyclosporin A 35 with N-bromosuccinimide and azo-bis-isobutyronitrile in a solvent such as carbon tetrachloride, producing the intermediate acetyl-η-bromocyclosporin A 41. N-bromosuccinimide is a reagent that is often used to replace allylic hydrogens with bromine, and it is believed to do so via a free radical mechanism. The preparation of the intermediate 41 was essentially described by M. K. Eberle and F. Nuninger in "Synthesis of the Main Metabolite (OL-17) of Cyclosporin A," *J. Org. Chem.*, Vol. 57, pp. 2689-2691 (1992).

The novel intermediate triphenylphosphonium bromide of acetyl cyclosporin A 42 may be prepared from acetyl-η-bromocyclosporin A 41 by heating the latter compound with triphenylphosphine in a solvent such as toluene.

The novel intermediate 42, and others like it, are contemplated to be key intermediates in the synthesis of a plurality of cyclosporin A analogs that contain a conjugated diene system in the 1-amino acid residue. For example, in addition to triphenylphosphine, compounds such as triarylphosphines, trialkylphosphines, arylalkylphosphines, and triarylarsines may be reacted with acetyl-η-bromocyclosporin A 41 to prepare other activated compounds similar to 42.

Referring again to FIG. 4, a mixture of the (E) and (Z)-isomers of acetyl-1,3-diene 43 may be prepared by stirring the triphenylphosphonium bromide of acetyl cyclosporin A 42 with an excess of formaldehyde in toluene at room temperature. Following addition of the formaldehyde, a base such as sodium hydroxide is added dropwise, and the isomeric mixture of dienes is extracted with ethyl acetate.

Numerous organic chemistry textbooks describe the Wittig reaction. One description in particular is provided by J. McMurry, *Organic Chemistry*, 5<sup>th</sup> Ed. (Brooks/Cole, Pacific Grove, 2000), pp. 780-783. A Wittig reaction may be used to convert a ketone or an aldehyde to an alkene. In such a process, a phosphorus ylide, also called a phosphorane, may be reacted with the aldehyde or ketone to give a dipolar intermediate called a betaine. Typically the betaine intermediate is not isolated; rather, it spontaneously decomposes through a four-membered ring to yield an alkene and triphenylphosphine oxide. The net result is a replacement of the carbonyl oxygen atom by the $R_2C=$ group originally bonded to the phosphorus.

It will be appreciated by those skilled in the art that a wide variety of reagents may be substituted for the exemplary Wittig reaction reagents cited above. For example, numerous alkyl, aryl, aldehyde, and ketone compounds may be substituted for formaldehyde to prepare a vast number of cyclosporin derivatives. Applicants have carried out the above synthesis with formaldehyde, and in place of formaldehyde, compounds such as acetaldehyde, deuterated formaldehyde, deuterated acetaldehyde, 2-chlorobenzaldehyde, benzaldehyde, and butyraldehyde. Such Wittig reactions may be carried out with compounds other than triphenylphosphonium derivatives, such as triarylphosphines, trialkylphosphines, arylalkylphosphines and triarylarsines. Instead of using sodium hydroxide, various other bases such as sodium carbonate, butyllithium, hexyllithium, sodium amide, lithium hindered bases such as lithium diisopropylamide, and alkali metal alkoxides may be used. In addition to varying these reagents, the reaction may be conducted in various organic solvents or mixtures of organic solvents and water, in the presence of various salts, particularly lithium halides, and at varying temperatures. All of the factors listed above can reasonably be selected by one of ordinary skill in the art to have the desired effect on the stereochemistry of the formed double bond; i.e., the desired effect on the ratio of the cis to trans-isomers.

In a final step of this synthesis, the protecting group on the β-carbon is removed using the following procedure. The mixture of acetyl-(E)-1,3-diene and acetyl-(Z)-1,3-diene 43 is dissolved in methanol, and then water is added. A base such as potassium carbonate is added, and the reaction mixture stirred at room temperature. Bases other than potassium carbonate that may be used include sodium hydroxide, sodium carbonate, sodium alkoxide, and potassium alkoxide. Ethyl acetate is then used to extract the final product mixture of (E) and (Z)-isomers of $ISA_{TX}247$ 44.

Method 2

Figure 5:
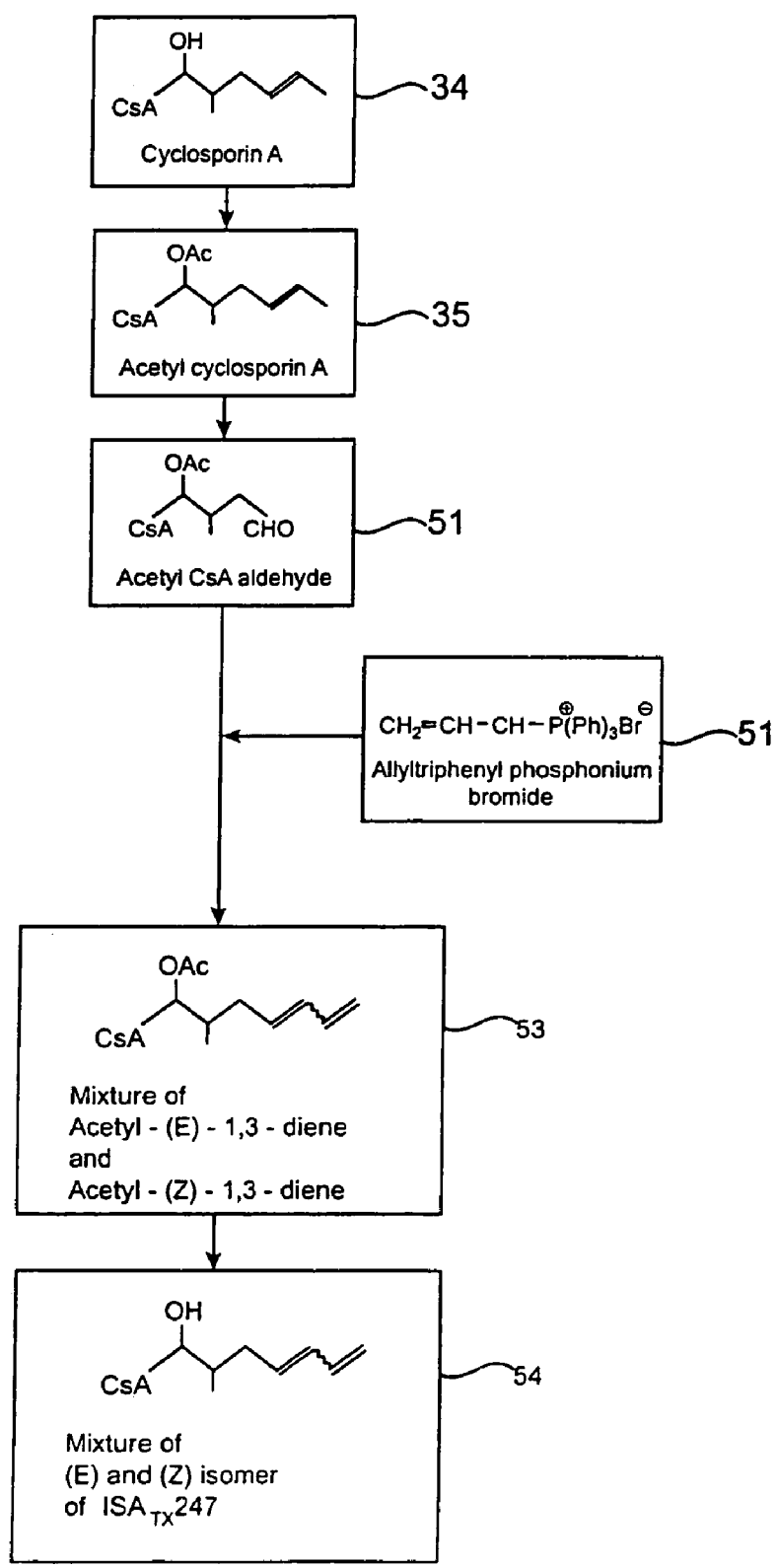
FIG. 5 illustrates another synthetic pathway that produces a mixture of (E) and (Z)-isomers of $ISA_{TX}247$ from an aldehyde precursor.

In an alternative reaction pathway for synthesizing a mixture of (E) and (Z)-isomers of $ISA_{TX}247$ via a Wittig reaction strategy, a four step synthetic pathway may be employed as follows: 1) protection of the β-alcohol, as in method 1, 2) oxidation of the acetyl-cyclosporin A produced from the first step to produce an aldehyde; 3) a Wittig reaction; and 4) de-acetylation of the Wittig reaction product, or equivalently, hydrolysis of the acetate ester to retrieve the alcohol. This reaction sequence is illustrated in FIG. 5.

This synthetic pathway begins in a manner similar to the Wittig reaction pathway of FIG. 4 in that the first step protects the β-alcohol with an acetate ester group. The two pathways differ from here on, however, in that the next step of method 2-converts acetyl-cyclosporin A 35 to an aldehyde, acetyl cyclosporin A aldehyde 51. This reaction uses an oxidizing agent sufficiently strong to cleave a C=C bond to produce two fragments. Alkene cleavage is known in the art. Ozone is perhaps the most commonly used double bond cleavage reagent, but other oxidizing reagents such as potassium permanganate ($KMnO_4$) or osmium tetroxide can cause double bond cleavage as well.

The use of ruthenium based oxidizing agents has been discussed by H. J. Carlsen et al. in "A Greatly Improved Procedure for Ruthenium Tetroxide Catalyzed Oxidations of Organic Compounds," *J. Org. Chem.*, Vol. 46, No. 19, pp 3736-3738 (1981). Carlsen et al. teach that, historically, the expense of ruthenium metal provided an incentive for the development of catalytic procedures, the most popular of which used periodate or hypochlorite as stoichiometric oxidants. These investigators found a loss of catalytic activity during the course of the reaction with the conventional use of ruthenium which they postulated to be due to the presence of carboxylic acids. The addition of nitriles to the reaction mixture, especially acetonitrile, was found to significantly enhance the rate and extent of the oxidative cleavage of alkenes in a $CCl_4/H_2O/IO_4^-$ system.

According to one embodiment of the present invention, acetyl cyclosporin A aldehyde 51 may be produced from acetyl cyclosporin A 35 by dissolving it in a mixture of acetonitrile and water, and then adding first sodium periodate and then ruthenium chloride hydrate. The aldehyde 51 may be extracted with ethyl acetate. It should be noted that the synthesis of the aldehyde 51 by this oxidative cleavage strategy is important to many of the stereoselective pathways to be discussed below, and consequently the reader is referred back to this section accordingly.

The third step of method 2 involves converting the aldehyde 51 to a mixture of (E) and (Z) dienes via a Wittig reaction, in a similar fashion to that of method 1. As in method 1, a phosphorus ylide adds to the aldehyde to yield a betaine (which is not isolated), with the net result that the carbonyl oxygen atom of the aldehyde is replaced by the $R_2C=$ group originally bonded to phosphorus. Again, such Wittig reactions may be carried out with phosphorus containing compounds other than triphenylphosphonium derivatives, such as triarylphosphines, trialkylphosphines, arylalkylphosphines and triarylarsines, at various temperatures, and using a variety of basic solutions and solvents or the addition of various inorganic salts may be used to influence the stereochemistry of the newly formed double bond.

In one embodiment, acetyl cyclosporin A aldehyde 51 is dissolved in toluene, to which is added a base such as sodium hydroxide in water. Allyl triphenylphosphonium bromide 52 is then added, and the reaction stirred for some time. Workup of the product mixture of acetyl (E) and (Z)-1,3-dienes 53 involves extraction with hexane and/or ethyl acetate, where the term "workup" is intended to mean the process of extracting and/or isolating reaction products from a mixture of reactants, products, solvent, etc.

In a final step of method 2, similar to the final step of method 1, the acetate ester group protecting the alcohol at the β-carbon position is removed with potassium carbonate, yielding a mixture of (E) and (Z) isomers of $ISA_{TX}247$ 54. Bases other than potassium carbonate that may be used to remove the protecting group include sodium hydroxide, sodium carbonate, sodium alkoxide, and potassium alkoxide.

Synthesis of Compositions Enriched in Either of the $ISA_{TX}^{247}$ (E) and (Z)-isomers via Organometallic Routes According to embodiments of the present invention, stereoselective synthetic pathways may employ the use of inorganic reagents containing elements such as silicon, boron, titanium, sulfur, phosphorus, and/or lithium. These pathways may proceed through a six-membered ring transition state where one of the members of the ring is the inorganic element from the organometallic reagent. In some embodiments, steric hindrance effects related to the transition state may influence the stereochemical outcome of the reaction.

Two exemplary stereoselective schemes will be discussed in the present disclosure. In the first stereoselective scheme (method 3, also shown as Pathway 32 in FIG. 3), a silicon-containing compound undergoes an elimination reaction to produce either the (E) or (Z)-isomer, depending on whether the elimination reaction is carried out under acidic or basic conditions. This is an example of a Peterson olefination. In the second stereoselective scheme (method 4, also shown as Pathway 33 in FIG. 3), each of the isomers is produced from a different precursor. The (Z)-isomer is produced from a titanium and phosphorus containing intermediates, whereas the (E)-isomer is produced through a lithium containing intermediate.

Method 3

This pathway proceeds via the acetyl cyclosporin A aldehyde 51.

Figure 6:
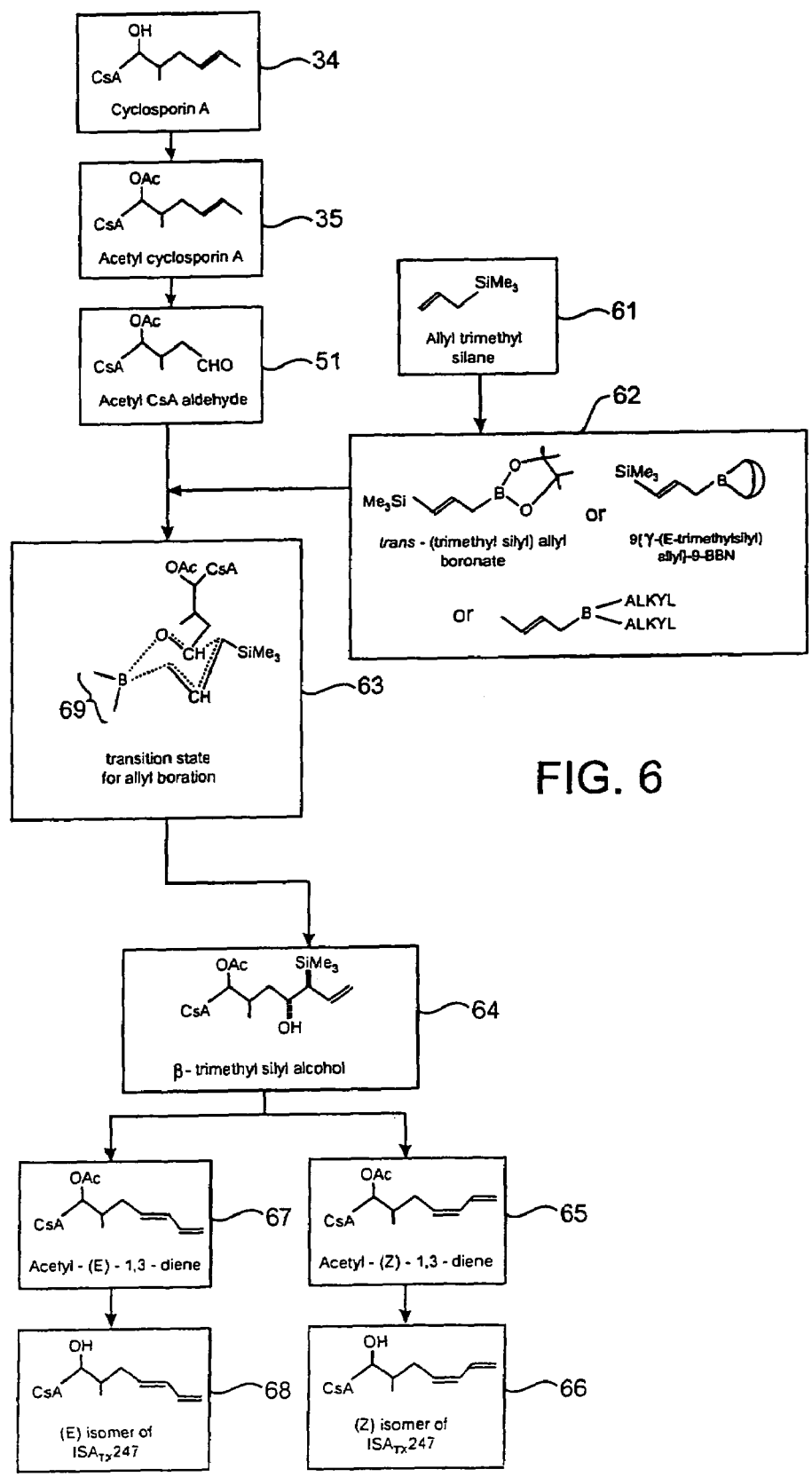
FIG. 6 illustrates an exemplary stereoselective reaction scheme that may be used to prepare compositions enriched in either the (E) or (Z)-isomers of $ISA_{TX}247$, wherein either isomer may be prepared from the same precursor alcohol.

A similar reaction scheme has been discussed in general by D. J. S. Tsai and D. S. Matteson in "A Stereocontrolled Synthesis of (Z) and (E) Terminal Dienes from Pinacol (E)-1-Trimethylsilyl-1-Propene-3-Boronate," *Tetrahedron Letters*, Vol. 22, No. 29, pp. 2751-2752 (1981). The method is illustrated in FIG. 6. In general, the synthesis involves preparing a trimethylsilylallylboronate ester reagent 62, and then treating acetyl cyclosporin A aldehyde 51 with 62 to form a β-trimethylsilyl alcohol 64. This alcohol is believed to form via a boron-containing transition state 63. As the boronate esters are slow-reacting in allylboration reactions, it will be appreciated by those skilled in the art that the use of a faster-reacting borane reagent such as E-γ-trimethylsilyl diethylborane or 9-(E-γ-trimethylsilylallyl)-9-BBN has advantages. The β-trimethylsilyl alcohol 64 may then undergo a Peterson olefination to prepare an alkene, in this case either the diene 65 or the diene 67.

Figure 10:
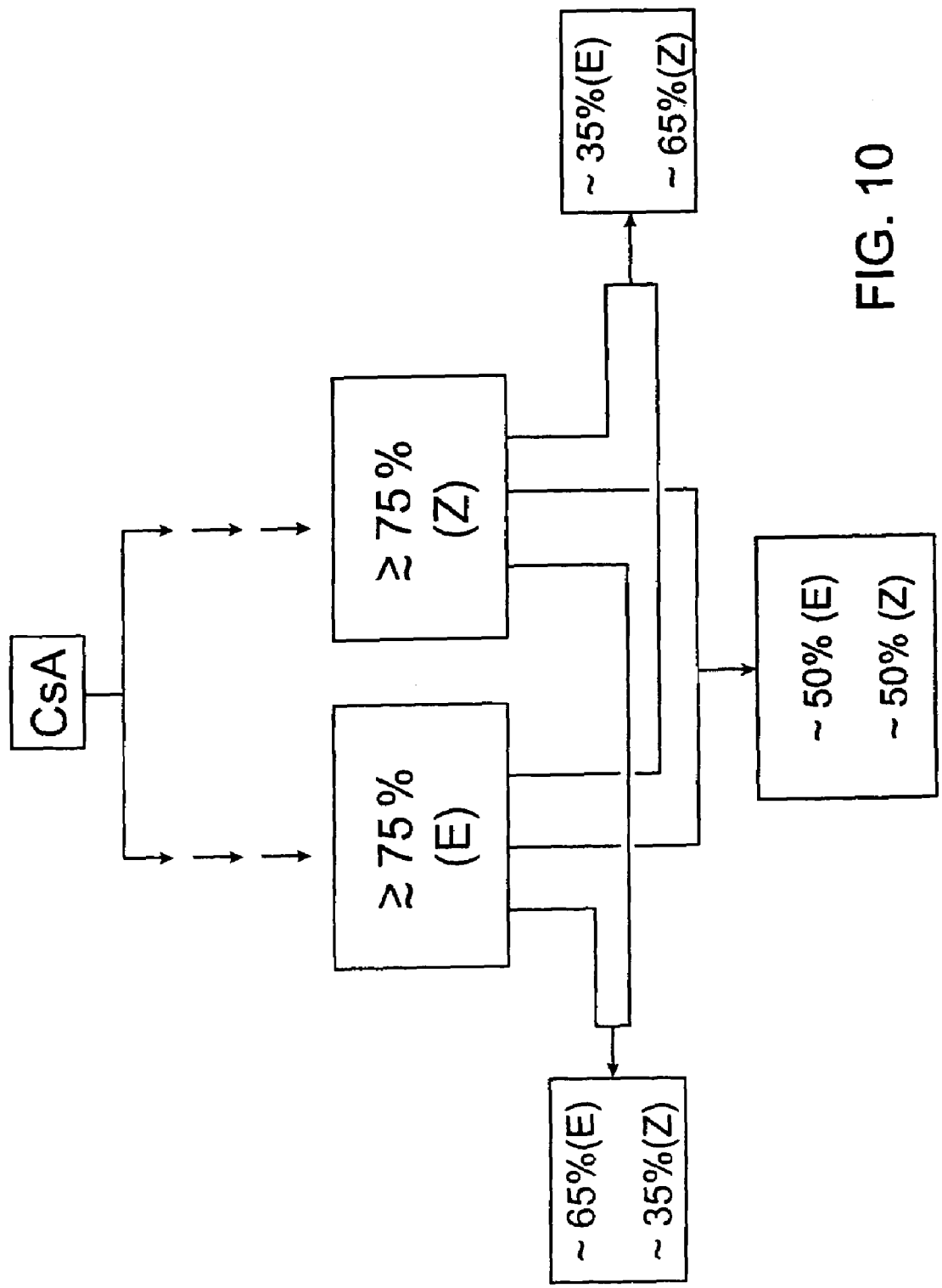
FIG. 10 illustrates exemplary stereoselective pathways for producing a mixture of the (E) and (Z)-isomers of $ISA_{TX}247$, where compositions enriched in one of the two isomers are first prepared, and then mixed accordingly in predetermined proportions to achieve the desired ratio.

Formation of the alkene follows one of two distinct paths, depending on whether the elimination reaction (the olefination) is carried out under acidic or basic conditions. Under acidic conditions an anti-elimination occurs forming the (E)-isomer, whereas under basic conditions a cis-elimination occurs to form the (Z)-isomer. It will be appreciated by those skilled in the art that by using this synthetic pathway, either isomer may be prepared from the same precursor. The product of each elimination reaction comprises a composition enriched in one of the two isomers. In one embodiment, enriched means that the composition contains greater than or equal to about 75 percent by weight of an isomer. In other embodiments, the enriched composition my comprise 80, 85, and 90 percent by weight of one of the isomers. The compositions enriched in an isomer may then be combined in a predetermined ratio to arrive at the desired mixture as illustrated in FIG. 10.

The reactions in FIG. 6 will now be discussed in detail, beginning with the preparation of the boron-containing reagent 62. A general investigation of the use of silicon reagents in the synthesis of carbon-carbon bond forming reactions has been discussed by E. Ehlinger and P. Magnus in "Silicon in Synthesis. 10. The (Trimethylsilyl)allyl Anion: A β-Acyl Anion Equivalent for the Conversion of Aldehydes and Ketones into γ-Lactones," *J. Am. Chem. Soc.*, Vol. 102, No. 15, pp. 5004-5011 (1980). In particular, these investigators teach the reaction between the (trimethylsilyl)allyl anion and an aldehyde. The anion may be prepared by deprotonating allyltrimethylsilane with sec-butyllithium in tetrahydrofuran at −76° C. containing 1 equivalent of tetramethylethylenediamine (TMEDA).

The deprotonation of allyltrimethylsilane (this step is not shown in FIG. 6) has been discussed by J.-F. Biellmann and J.-B. Ducep in "Allylic and Benzylic Carbanions Substituted by Heteroatoms," *Organic Reactions*, Vol. 27 (Wiley, New York, 1982), p. 9. A proton alpha to the heteroatom in substituted allylic systems may be removed with a more basic agent. A large variety of such agents are available, with perhaps n-butyllithium being the most common. n-Butyllithium is used in a stoichiometric amount with the compound to be metalated in solution with tetrahydrofuran (THF). The temperature is usually maintained below 0° C. (often below −76° C) where the n-butyllithium has a low reactivity due to its polymeric nature. Addition of a chelating agent such as N,N,N',N'-tetramethylethylenediamine (TMEDA) causes the polymer to dissociate. However, the reaction can also be done at room temperature, even in the absence of TMEDA.

Allylsilanes are easily deprotonated because the anion that is generated is stabilized not only through conjugation with the adjacent double bond, but also by the neighboring silyl group. The anion may react with electrophiles through either its α-carbon or its γ-carbon. The regiochemical and stereochemical outcome of these reactions depends on several factors, one of the most important of which is the identity of the counterion. See the discussion of allylsilanes by S. E. Thomas in *Organic Synthesis: The Roles of Boron and Silicon* (Oxford University Press, New York, 1991), pp. 84-87.

In this reaction scheme, the deprotonated allylsilane then undergoes an electrophilic capture by trimethylborate to produce an intermediate, which, when reacted with pinacol, yields the trans-(trimethylsilyl) boronate compound 62. The boronate 62 may also be called an "allylborane" (allylboronate ester). Alternatively, if 9-methoxy-9-dialkylborane is used in the electrophilic capture it would lead to a boronate complex which can be demethoxylated using a boron trifluoride reagent (such as BF3Et$_2$O) to generate the corresponding 9-(γ-trans-trimethylsilylallyl)-9-dialkylborane.

The addition of an aldehyde to an allylborane has been discussed by S. E. Thomas in the above reference at pages 34-35. The addition of an aldehyde to an allylborane, wherein the latter is unsymmetrically substituted at the distal end of the carbon-carbon double bond ("distal" meaning furthest away from the boron atom) produces a homoallylic alcohol containing two adjacent chiral centers. (E)-allylboranes give rise to the threo-diastereoisomer, while (Z)-allylboranes give rise to the erythro-diastereoisomer. An exemplary reaction of an (E)-allylborane 62 with cyclosporin A aldehyde 51 is shown in FIG. 6, where the boron intermediate 63 is formed after stirring the reactants in a THF solution for a period of several days.

The reference numeral 69 in the boron intermediate 63 FIG. 6) is meant to indicate that any number of structures are possible at the boron position. For example, if the boronate reagent 62 is a trialkylsilylallyl boronate ester, then the structure at 69 would comprise a 5-membered ring that includes two oxygen atoms. Substitutions on the boronate or borane reagents employed in 62 will be present in the structure in 63.

It has been postulated that the stereoselectivity that is achieved in reactions involving allylboranes with aldehydes may be due to the six-membered ring chair-like transition state exemplified by the boron intermediate 63, and depicted in FIG. 6. Only the two carbonyl atoms of the aldehyde (the carbon and the oxygen which are double bonded) become members of the six-membered ring transition; the remainder of the aldehyde extends off the ring. The CsA portion of the aldehyde that extends away from the six-membered ring is postulated to exist in an equatorial rather than axial position relative to the ring because the latter configuration would give rise to unfavorable steric hindrance between that substituent and an oxygen atom of the allylborane 62. It will also be appreciated by those skilled in the art that the position of the SiMe$_3$ group from the (trimethylsilyl)allyl anion is shown occupying an equatorial position in FIG. 6 because this example started with the (E)-diastereomer of the allylborane. Alternatively, the SiMe$_3$ group could have been drawn in an axial position if the starting allylborane had been the (Z)-diastereomer.

Alternatively, it is contemplated to prepare the erythrosilyl alcohol, for which acid elimination would give the cis-isomer and base elimination would give the trans-isomer, in an opposite manner to the elimination reactions discussed above. It will be obvious to those skilled in the art that the same products would be obtained at the end of the synthesis.

Treatment of the transition state product 63 with triethanolamine yields the β-trimethylsilyl alcohol 64. On the other hand, allylboration product of (trimethylsilylallyl)dialkyl borane yields silyl alcohol 64 upon-oxidation using NaOH/H$_2$O$_2$ or aqueous workup. The alcohol 64 depicted in FIG. 6 is the threo-diastereoisomer, since the transition state allylborane 63 was in the (E)-configuration, although it will be appreciated by those skilled in the art that the other diastereoisomere could have been prepared as well if starting from the Z-allylborane reagent. The diastereoselectivity in the newly created chiral centers is not determined at this stage due to removal of these chiral centers at a later stage of the synthesis. The structure of the β-trimethylsilyl alcohol 64 shown in FIG. 6 has been confirmed by the applicants using spectral techniques.

In a method of alkene synthesis known as a Peterson olefination, elimination of the trialkylsilyl group and the hydroxy group from the β-trimethylsilyl alcohol 64 leads to an alkene; in this case a diene, due to the double bond that is already present between the two terminal carbons of the chain. A discussion of the conversion of β-hydroxysilanes to alkenes has been presented in the S. E. Thomas reference at pages 68-69. A further discussion of this reaction is presented by P. F. Hurdlik and D. Peterson in "Stereospecific Olefin-Forming Elimination Reactions of β-Hydroxysilanes," *J. Am. Chem. Soc.*, Vol. 97, No. 6, pp. 1464-1468 (1975).

Referring to FIG. 6, the elimination reaction converting the alcohol 64 to a diene may follow one of two distinct mechanistic pathways depending on whether the reaction is carried out under acidic or basic conditions. One pathway leads to the diene 65, while the other pathway leads to the diene 67. Under acidic conditions anti-elimination occurs, while under basic conditions syn-elimination occurs. In other words, the elimination reactions of β-hydroxysilanes are stereospecific, and the acid- and base-promoted reactions take the opposite stereochemical course. Typical acids for the acid-promoted reaction may include acetic acid, sulfuric acid and various Lewis acids; typical bases include sodium hydride and potassium hydride or potassium tertibutoxide. It may be the case that elimination reactions using sodium hydride in THF are slow at room temperature, while elimination reactions that use potassium hydride take place more readily.

The stereospecificity occurs at this stage of the reaction pathway because elimination under acidic conditions requires the trimethylsilyl and hydroxy groups to be in an antiperiplanar relationship. In contrast, elimination under basic conditions requires that the trimethylsilyl and hydroxy groups adopt a synperiplanar relationship. The latter condition facilitates the formation of a strong silicon-oxygen bond and an intermediate four-membered ring, which breaks down in a manner analogous to the final step of a Wittig reaction. It will be appreciated by those skilled in the art that a strong silicon-oxygen bond replaces a weaker silicon-carbon bond, which overrides the replacement of a strong carbon-oxygen bond with a weaker carbon-carbon π bond.

Thus the products of the stereospecific elimination of a β-hydroxy alkylsilane are the acetyl-(E)-1,3-diene compound 67 and the acetyl-(Z)-1,3-diene compound 65. As in the previous methods, the protecting group may now be removed from each of these dienes by treatment with K$_2$CO$_3$ in methanol and water. This removes the acetate group bonded to the β-carbon of the 1-amino acid residue, returning the functional group on that carbon to an alcohol. Bases other than potassium carbonate that may be used to remove the protecting group include sodium hydroxide, sodium carbonate, sodium alkoxide, and potassium alkoxide.

At this stage of the preparation the synthesis is substantially complete. The compositions enriched in one or the other of the isomers may be mixed to achieve the desired ratio of isomers in the mixture. By "enriched" is meant a product that comprises at least about 75 percent by weight of that isomer; in other words, the product may contain up to 25 percent by weight of the "undesired" isomer. The mixture is designed to achieve the desired pharmacological result.

Method 4

This pathway also proceeds via the acetyl cyclosporin A aldehyde 51.

Figure 7:
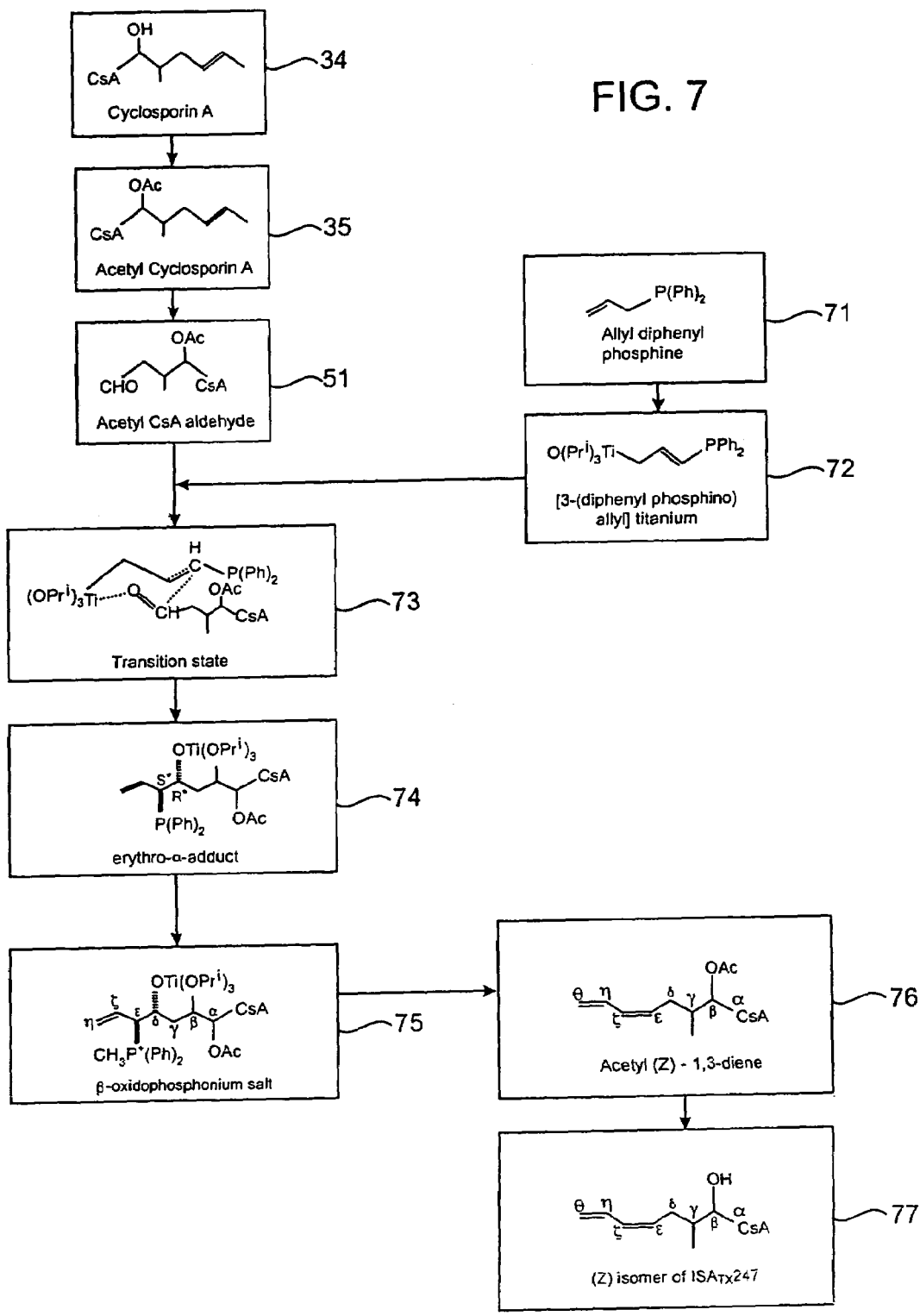
FIG. 7 illustrates an alternative reaction scheme for the stereoselective synthesis of a composition enriched in the (Z)-isomer of $ISA_{TX}247$.
Figure 8:
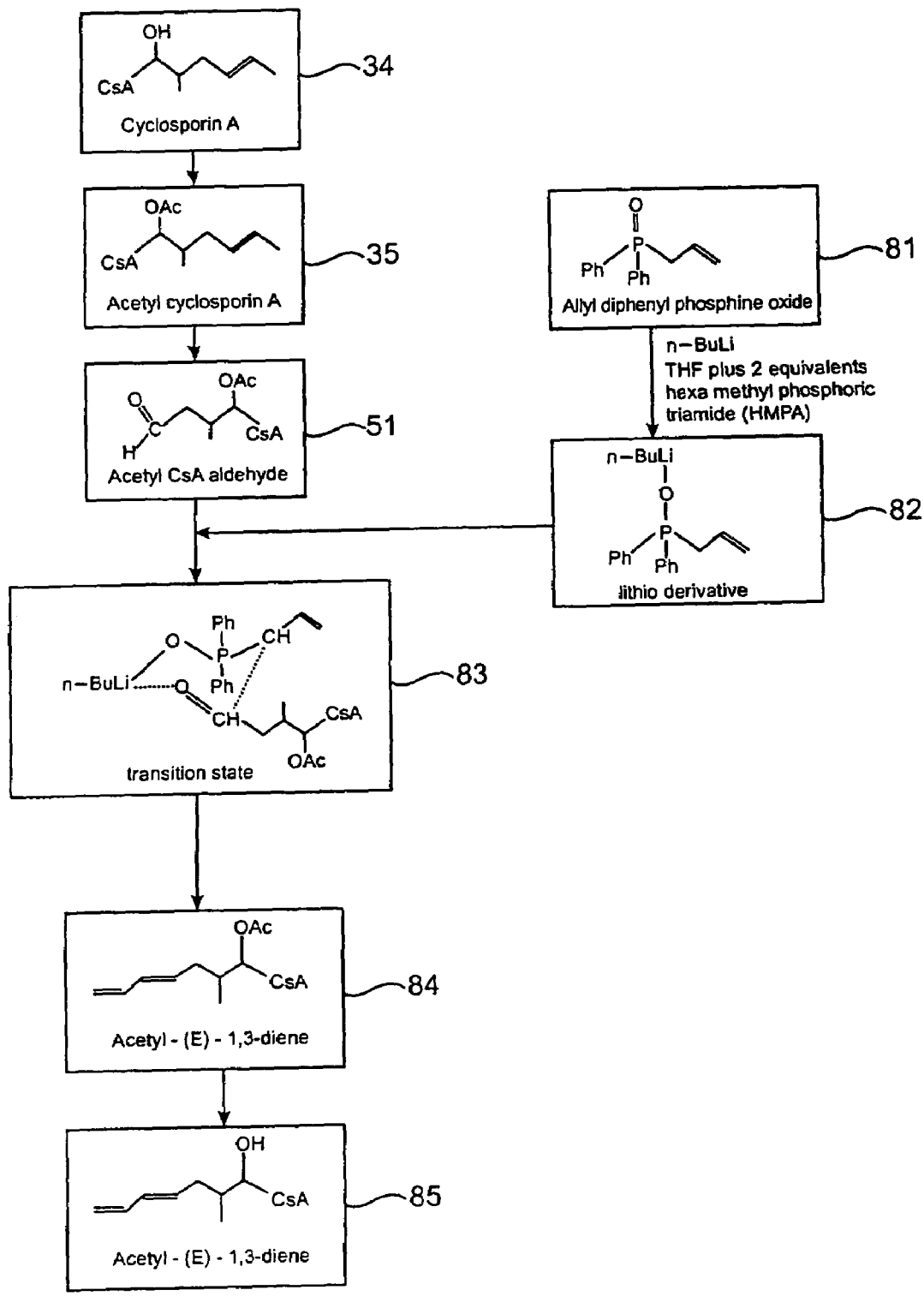
FIG. 8 illustrates an alternative reaction scheme for the stereoselective synthesis of a composition enriched in the (E)-isomer of $ISA_{TX}247$.

An alternate scheme for producing stereoselective isomers is illustrated in FIGS. 7-8. This synthetic pathway differs from those previously discussed, in that 1) the synthetic pathway for producing the (E)-isomer of ISA$_{TX}$247 proceeds through different intermediates than that for the (Z)-isomer, and 2) these synthetic pathways make use of titanium and lithium-containing reagents and/or intermediates.

Titanium reagents are known to be particularly useful in organic synthesis because they are regio- and stereoselective in their reactions with aldehydes and ketones. The general nature of titanium in stereoselective chemistry has been discussed by M. T. Reetz in *Organotitanium Reagents in Organic Synthesis* (Springer-Verlag, Berlin, 1986), pp. VII, 148-149, and 164-165. Here it is stated that the nature of the titanium ligand may be varied such that the electronic and steric identity of the reagent can be manipulated, and the stereochemical outcome of many C—C bond forming reactions may be predicted. According to this chemistry, the union of two prochiral centers of achiral molecules creates two centers of chirality. A general rule governing the stereoselective outcome is that Z-configured enolates or crotyl metal compounds preferentially form syn-adducts, while E-configured reagents favor the anti-diastereomers. The trends may again be explained by assuming a six-membered cyclic transition state having a chair geometry.

A specific example of this type of stereoselective synthesis has been discussed by Y. Ikeda et al. in "Stereoselective Synthesis of (Z)- and (E)-1,3-Alkadienes from Aldehydes Using Organotitanium and Lithium Reagents," *Tetrahedron*, Vol. 43, No. 4, pp. 723-730 (1987). This reference discloses that allyldiphenylphosphine may be used to produce a [3-(Diphenylphosphino)allyl]titanium reagent, which in turn may be condensed with an aldehyde followed by phosphonium salt formation to give a (Z)-1,3-alkadiene in a highly regio- and stereoselective manner. In contrast, alithiated allyldiphenylphosphine oxide can condense with an aldehyde to give an (E)-1,3-alkadiene directly, again with the desired stereoselectivity.

Referring to FIG. 7, synthesis of the (Z)-isomer of $ISA_{TX}247$ proceeds (as in the previous schemes) by generating acetyl cyclosporin A aldehyde 51 from cyclosporin A 34. The [3-(diphenylphosphino)allyl]titanium reagent 72 is prepared by deprotonating allyldiphenylphosphine 71 with a strong base such as t-BuLi, and then reacting the product with titanium tetraisopropoxide. A transition state 73 is theoretically proposed leading to the erythro-α-adduct 74, which then may be converted to the β-oxidophosphonium salt 75 by treatment of 74 with iodomethane (MeI). It is postulated that the existence of the transition state 73 is at least in part responsible for the stereoselectivity of this synthetic pathway.

In accordance with the exemplary methods outlined in the present disclosure, the metal site of the organometallic reagent may be the entity that controls regioselectivity (Ikeda, p. 725). This means that the aldehyde 51 in FIG. 7 reacts with the diphenylphosphino compound 72 at its α-position to give the corresponding α-adduct 74, since the γ-carbon of the diphenylphosphino group is coordinated to the metal, which in this case is titanium. The observed Z selectivity of the diene product is explained by considering the six-membered transition state 73. Since both the bulky cyclosporin A side chain of the aldehyde 35 and the diphenylphosphino group are postulated to occupy equatorial positions in the transition state, the erythro α-adduct 74 is selectively formed, giving rise to the (Z)-1,3-diene 76.

In contrast to the reaction pathway depicted in FIG. 7, in which the (Z)-isomer of $ISA_{TX}247$ is produced via a titanium transition state, the (E)-isomer is not as easily produced by this method. In fact, attempts to synthesize the (E)-isomer by this method are generally reported to result in low yields. Instead, as shown in FIG. 8, the lithio derivative 82 may be reacted with the aldehyde 51 to produce the lithium containing transition state 83, which forms the 1,3-diene in E/Z ratios in a range greater than approximately 75:25. As in FIG. 7, the high stereoselectivity of the reaction product is possibly due to the transition state 83, in which the vinyl group of the lithium reagent 82 and the cyclosporin A side chain of the aldehyde 51 are postulated to occupy equatorial positions, thereby producing the (E)-1,3-diene 84 in a stereoselective manner. As discussed previously, certain undesirable side-reactions involving the acetate protecting group may be avoided in all stereoselective syntheses through the use of protecting groups such as benzoate esters or silyl ethers.

Preparation of Mixtures

As stated previously, certain mixtures of cis and trans-isomers of $ISA_{TX}247$ were found to exhibit a combination of enhanced potency and/or reduced toxicity over the naturally occurring and presently known cyclosporins.

According to embodiments of the present invention, $ISA_{TX}247$ isomers (and derivatives thereof) are synthesized by stereoselective pathways that may vary in their degree of stereoselectivity. Stereoselective pathways may produce a first material or composition enriched in the (E)-isomer, and a second material or composition enriched in the (Z)-isomer, and these materials may then be combined such that the resulting mixture has a desired ratio of the two isomers. Alternatively, it is contemplated that the first material may be prepared by separating a reaction product to isolate and enrich the (E)-isomer, and the second material may be prepared by separating a reaction product to isolate and enrich the (Z)-isomer. In yet another embodiment, the reactions conditions of a stereoselective pathway may be tailored to produce the desired ratio directly in a prepared mixture.

Figure 9C:
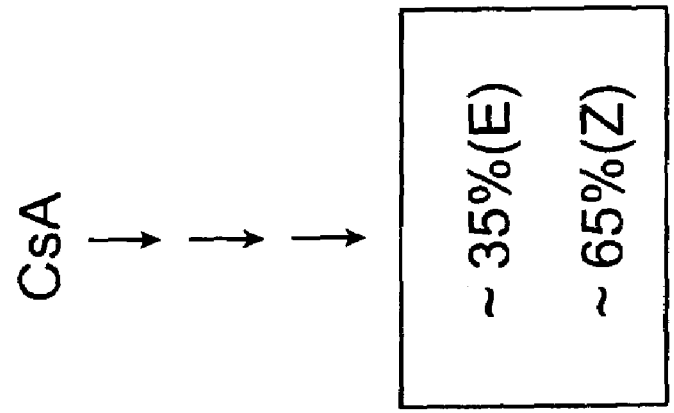
FIGS. 9A-C illustrate exemplary synthetic pathways for producing a mixture of the (E) and (Z)-isomers of $ISA_{TX}247$, the conditions of each reaction having been tailored to produce a particular exemplary ratio of the two isomers.
Figure 9B:
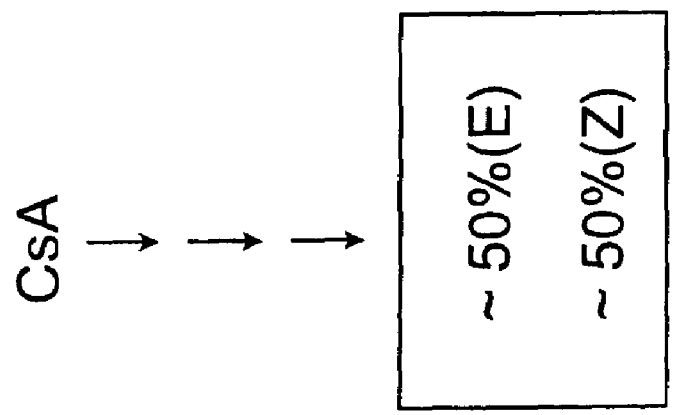
Figure 9A:
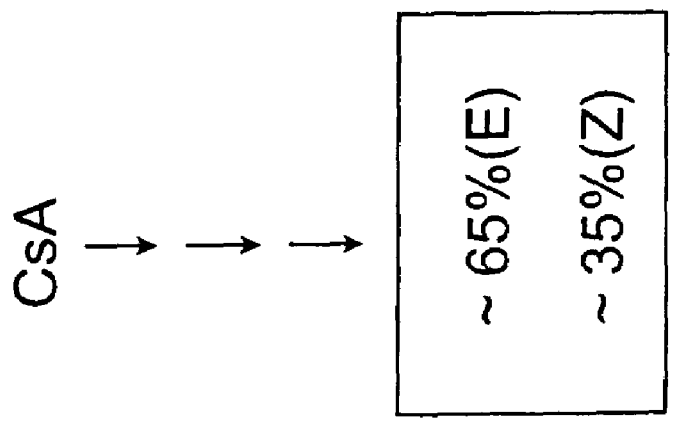

These principles are illustrated in FIGS. 9A-C and 10. In FIGS. 9A-C, three hypothetical synthetic reactions are shown that produce ratios of the (E) to the (Z)-isomer of approximately 65 to 35 percent by weight, 50 to 50 percent by weight, and 35 to 65 percent by weight, respectively. Of course, these ratios are exemplary and for illustrative purposes only, and any hypothetical set of numbers could have been chosen. It will be obvious to those skilled in the art that the reaction conditions used to produce the ratio in FIG. 9A may be different from those of FIGS. 9B and 9C in order to achieve a different ratio of isomers in the product mixture. The conditions of each reaction have been tailored to produce a particular ratio of the two isomers for that case.

In contrast to some synthetic pathways, where a mixture of isomers is produced, the isomers may first be prepared individually, and then mixed in predetermined proportions to achieve the desired ratio. This concept is illustrated in FIG. 10, where the product of one stereoselective pathway is enriched in one of the isomers such that the product comprises greater than about 75 percent by weight of the (E) isomer, and the product of the other stereoselective pathway is enriched in the other isomer such that this product comprises greater than about 75 percent by weight of the (Z) isomer. These numbers are exemplary too, and the purity of the desired isomer resulting from a stereoselective pathway may be greater than or equal to about 75 percent by weight in one embodiment. In other embodiments the desired isomer may comprise greater than or equal to about 80, 85, 90, and 95 percent by weight, respectively.

After synthesizing the isomers individually, they may be mixed to achieve the desired ratio, as illustrated in FIG. 10. For illustrative purposes, the same hypothetical ratios are chosen in FIG. 10 as those used in FIGS. 9A-C. Referring to FIG. 10, the (E) and (Z)-isomers are mixed to yield three different mixtures that comprise ratios of the (E) to the (Z)-isomer of approximately 65 to 35 percent by weight, 50 to 50 percent by weight, and 35 to 65 percent by weight, respectively.

In an alternative embodiment, a mixture of the (E) and (Z)-isomers of $ISA_{TX}247$ isomers may be separated such that the mixture is enriched in one isomer over the other. For example, a Diels-Alder reaction may be used to convert the cis-isomer to a closed ring compound by reacting it with an alkene. If the alkene is bound to a substrate that is capable of isolation (e.g., filterable), the cis isomer may be substantially removed from the mixture, leaving a composition enriched in the trans isomer. The cis isomer may be reconstituted from the closed ring compound with the application of heat, producing a composition enriched in the cis isomer. Thus, in this manner, the cis and trans isomers may be separated.

In practice, the ratio of the (E) to (Z)-isomers in any mixture, regardless of the degree of stereoselectivity of the method by which it was produced, may take on a broad range of values. For example, the mixture may comprise from about 10 to 90 percent of the (E)-isomer to about 90 to 10 percent of the (Z)-isomer. In other embodiments, the mixture may contain from about 15 to 85 percent by weight of the (E)-isomer and about 85 to 15 percent of the (Z)-isomer; or about 25 to 75 percent by weight of the (E)-isomer and about 75 to 25 percent by weight of the (Z)-isomer; or about 35 to 65 percent by weight of the (E)-isomer and about 65 to 35 percent by weight of the (Z)-isomer; or about 45 to 55 percent by weight of the (E)-isomer and about 55 to 45 percent of the (Z)-isomer. In still another embodiment, the isomeric mixture is an $ISA_{TX}247$ mixture which comprises about 45 to 50 percent by weight of the (E)-isomer and about 50 to 55 percent by weight of the (Z)-isomer. These percentages by weight are based on the total weight of the composition, and it will be understood that the sum of the weight percent of the (E) isomer and the (Z) isomer is 100 weight percent. In other words, a mixture might contain 65 percent by weight of the (E)-isomer and 35 percent by weight of the (Z)-isomer, or vice versa.

The percentage of one isomer or another in a mixture can be verified using nuclear magnetic resonance (NMR), or other techniques well known in the art.

Pharmaceutical Compositions

This invention also relates to a method of treatment for patients in need of immunosuppression involving the administration of pharmaceutical compositions comprising the inventive mixture as the active constituents. The indications for which this combination is of interest include in particular autoimmune and inflammatory conditions and conditions associated with or causal to transplant rejection, e.g., treatment (including amelioration, reduction, elimination or cure of etiology or symptoms) or prevention (including substantial or complete restriction, prophylaxis or avoidance) of the following:

a) Acute organ or tissue transplant rejection, e.g., treatment of recipients of, e.g., heart, lung, combined heart-lung, liver, kidney, pancreatic, skin, bowel, or corneal transplants, especially prevention and/or treatment of T-cell mediated rejection, as well as graft-versus-host disease, such as following bone marrow transplantation.

b) Chronic rejection of a transplanted organ, in particular, prevention of graft vessel disease, e.g., characterized by stenosis of the arteries of the graft as a result of intima thickening due to smooth muscle cell proliferation and associated effects.

c) Xenograft rejection, including the acute, hyperacute or chronic rejection of an organ occurring when the organ donor is of a different species from the recipient, most especially rejection mediated by B-cells or antibody-mediated rejection.

d) Autoimmune disease and inflammatory conditions, in particular inflammatory conditions with an etiology including an immunological or autoimmune component such as arthritis (for example rheumatoid arthritis, arthritis chronica progrediente and arthritis deformans) and other rheumatic diseases. Specific autoimmune diseases for which the synergistic combination of the invention may be employed include, autoimmune hematological disorders (including e.g. hemolytic anemia, aplastic anemia, pure red cell anemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, (autoimmune) inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis. Autoimmune and inflammatory conditions of the skin are also considered to be amenable to treatment and prevention using the synergistic combination of the invention, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin, as are inflammatory conditions of the lungs and airways including asthma, allergies, and pneumoconiosis.

The isomeric analogue mixtures of this invention may be administered neat or with a pharmaceutical carrier to a warm-blooded animal in need thereof. The pharmaceutical carrier may be solid or liquid. The inventive mixture may be administered orally, topically, parenterally, by inhalation spray or rectally in dosage unit formulations containing conventional non-toxic pharmaceutically acceptable carriers, adjuvants and vehicles. The term parenteral, as used herein, includes subcutaneous injections, intravenous, intramuscular, intrastemal injection or infusion techniques.

The pharmaceutical compositions containing the inventive mixture may preferably be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to methods known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. No. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may include: (1) suspending agents such as sodium carboxymethylcellulose, methylcellulose, hydroxypropylmethylcellulose, sodium alginate, polyvinylpyrrolidone, gum tragacanth and gum acacia; or (2) dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitol monooleate, or a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose, aspartame or saccharin.

Oily suspension may be formulated by suspending the active ingredient in a vegetable oil, for example arachis oil, olive oil, sesame oil or coconut oil, a fish oil which contains omega 3 fatty acid, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in a mixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions containing the inventive mixture may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial ester 30 derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol, aspartame or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

The inventive mixture may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the disclosed cyclosporines are employed.

In a particularly preferred embodiment, a liquid solution containing a surfactant, ethanol, a lipophilic and/or an ampiphilic solvent as non-active ingredients is used. Specifically, an oral multiple emulsion formula containing the isomeric analogue mixture and the following non-medicinal ingredients: d-alpha Tocopheryl polyethylene glycol 1000 succinate (vitamin E TPGS), medium chain triglyceride (MCT) oil, Tween 40, and ethanol is used. A soft gelatin capsule (comprising gelatin, glycerin, water, and sorbitol) containing the isomeric analogue mixture and the same non-medicinal ingredients as the oral solution may also preferably be used.

Dosage levels of the order from about 0.05 mg to about 50 mg per kilogram of body weight per day are useful in the treatment of the above-indicated conditions. The dose level and schedule of administration may vary depending on the particular isomeric mixture used, the condition to be treated, and such additional factors as the age and condition of the subject. Preferred doses are from about 0.5 to about 10 mg/kg/day and from about 0.1 to about 10 mg/kg/day. In a preferred embodiment, from about 2 to about 6 mg/kg/day is administered orally b.i.d. In a particularly preferred embodiment, about 0.5 to about 3 mg/kg/day is administered orally b.i.d.

The amount of active ingredient that may be combined with the carrier materials to produce a single dosage form will vary depending upon the host treated and the particular mode of administration. For example, a formulation intended for the oral administration to humans may contain from 2.5 mg to 2.5 g of active agent compounded with an appropriate and convenient amount of carrier material which may vary from about 5 to about 95 percent of the total composition. Unit dosage forms will generally contain between from about 5 mg to about 500 mg of active ingredient. In a preferred embodiment, individual capsules containing about 50 mg isomeric mixture are employed for oral administration. In another preferred embodiment, oral solutions containing about 50 mg/mL isomeric mixture are used for oral administration.

It will be understood, however, that the specific dose level for any particular patient will depend upon a variety of factors including the activity of the specific compound employed, the age, body weight, general health, sex, diet, time of administration, route of administration, rate of excretion, drug combination and the nature and severity of the particular disease or condition undergoing therapy.

Methodology

The use of cyclosporine derivatives, a class of cyclic polypeptides produced by the fungus *Tolypocladium inflatum Gams*, is increasing in immunosuppressive therapy due to their preferential effects on T-cell mediated reactions. Cyclosporine derivatives have been observed to reversibly inhibit immunocompetent lymphocytes, particularly T-lymphocytes, as well as inhibit lymphokine production and release. This action is primarily mediated through cyclosporine A-induced inhibition of calcineurin, a phosphatase enzyme found in the cytoplasm of cells (Schreiber and Crabtree, 1992). An indicator of the efficacy of cyclosporine A or a cyclosporine A derivative is its ability to inhibit the phosphatase activity of calcineurin. The calcineurin inhibition assay measures the activity of the drug at its site of action, and, as such, is the most accurate and direct in vitro assessment of the potency of cyclosporine A analogues (Fruman et al., 1992).

$ISA_{TX}247$ is a cyclosporine A analogue that is similar to cyclosporine A, except for a novel modification of a functional group on the amino acid 1 residue of the molecule. We have now found that $ISA_{TX}247$ exhibits up to 3-fold greater potency than cyclosporine A in the in vitro calcineurin inhibition assay.

Pharmacodynamic studies (in vivo and in vitro) have shown that $ISA_{TX}247$ has more potency than other existing cyclosporine compounds. The efficacy of isomeric mixtures of cyclosporine analogues ranging from about 10:90 to about 90:10 (trans- to cis-), in particular $ISA_{TX}247$ having 50-55% Z-isomer and 45-50% E-isomer, as an immunosuppressive agent (versus cyclosporine A) has been demonstrated in an in vitro calcineurin activity assay, a rat heart transplant model, an islet cell allotransplantation mouse model, a collagen-induced arthritis model in the mouse, and/or an antigen-induced arthritis model in the rabbit. The data show that these isomeric mixtures are equivalent to or more potent than cyclosporine A, and therefore useful for the treatment of immunoregulatory disorders.

There are numerous adverse effects associated with cyclosporine A therapy, including nephrotoxicity, hepatotoxicity, cataractogenesis, hirsutism, parathesis, and gingival hyperplasia to name a few (Sketris et al., 1995). Of these, nephrotoxicity is one of the more serious dose-related adverse effects resulting from cyclosporine A administration. The exact mechanism by which cyclosporine A causes renal injury is not known. However, it is proposed that an increase in the levels of vasoconstrictive substances in the kidney leads to the local vasoconstriction of the afferent glomerular arterioles. This can result in ischemia, a decrease in glomerular filtration rate, and over the long term, interstitial fibrosis.

The nonclinical safety of $ISA_{TX}247$ has been evaluated in a number of animal species. Repeated-dose oral toxicity studies in rats, dogs, and primates showed that $ISA_{TX}247$ was well-tolerated and produced effects that were consistent with immunosuppression. The only toxicological effect noted in all species was diarrhea/loose feces.

$ISA_{TX}247$ does not exhibit mutagenic activity as demonstrated in in vitro bacterial reverse mutation and chromosome aberration assays, and in an in vivo rat micronucleus assay. No carcinogenicity studies have been completed to date. Reproductive toxicity studies with $ISA_{TX}247$ have been completed in pregnant rats and rabbits. There were no treatment-related malformations or alterations. At doses that resulted in material toxicity, corresponding embryotoxicity was observed.

EXAMPLES

Example 1

Acetylation of Cyclosporine A

Acetic anhydride (140 milliliters) was added to Cyclosporin A (50.0 grams, 41.6 millimoles) and the mixture stirred at room temperature under a $N_2$ atmosphere until all of the Cyclosporin A has dissolved. Dimethylaminopyridine (7.62 g, 62.4 mmol) was added and the reaction stirred at room temperature under a $N_2$ atmosphere for 3 hours or until the reaction was complete. The reaction mixture was cooled to 5° C. and then filtered. The collected solids were washed with hexane to drive off additional acetic anhydride. The resulting pasty solid was slowly transferred to a vigorously stirred 5% aqueous sodium bicarbonate solution (1.5 liters). The resulting suspension was stirred until a fine slurry was obtained and the evolution of $CO_2$ had ceased. The solids were collected by filtration and washed with water until the filtrate had neutral pH. The solid product was dried in a vacuum oven overnight (55° C.) to give 44.0 g (85%) of the product as a colorless solid.

Example 2

Oxidation of Product from Example 1

Acetonitrile (320 mL) and water (80 mL) were added to acetyl Cyclosporin A (42.97 g, 34.54 mmol) and the mixture stirred until all of the material was dissolved. Sodium periodate (14.77 g, 69.08 mmol) was added, followed by the addition of ruthenium chloride hydrate (0.358 g, 1.73 mmol) and then the reaction stirred at room temperature for 3 hours under a $N_2$ atmosphere. Water (300 mL) was added and the mixture transferred to a separatory funnel. The mixture was extracted twice with ethyl acetate (300 mL and then 250 mL). The dark black ethyl acetate extracts were combined and washed with 250 mL water followed by 250 mL brine. The organic solution was then dried over $MgSO_4$ and the solvent evaporated to give a greenish-black solid. The crude product was chromatographed over silica gel using 40% acetone/60% hexane as eluent to give the product (29.1 g, 68%) as a colorless solid.

Example 3

Preparation of Acetyl $ISA_{TX}^{247}$ i) In Situ Generation of Ylide:

Acetyl Cyclosporin A aldehyde (31.84 g, 25.84 mmol) was added to 340 mL toluene and the mixture stirred until the material was completely dissolved. To the resulting solution was added 340 mL of 1 normal aqueous sodium hydroxide. The resulting mixture was stirred vigorously and then allyl triphenylphosphonium bromide (58.22 g, 151.90 mmol) added. The reaction was stirred for 24 hours at room temperature and then additional allyl triphenylphosphonium bromide (16.64 g, 43.42 mmol) added and stirring continued for a further 24 hours. The mixture was transferred to a separatory funnel and the toluene phase separated. The aqueous phase was extracted with an additional 200 mL of toluene. The two toluene extracts were combined and washed sequentially with 200 mL deionized water and 200 mL saturated aqueous sodium chloride solution. The solution was dried over $MgSO_4$, filtered, and the toluene evaporated to give a very viscous gel. This material was treated with 142 mL of ethyl acetate and stirred until a fine slurry formed. Hexane (570 mL) was slowly added with rapid stirring. The stirring was continued for 30 minutes and then-the resulting suspension was filtered and the collected solids washed with 160 mL of 5:1 hexane/ethyl acetate. The combined filtrate was concentrated on a rotary evaporator to a viscous semi-solid. This material was treated with 75 mL ethyl acetate and stirred until a fine slurry was obtained. Hexane (225 mL) was slowly added with rapid stirring. Stirring was continued for 30 minutes and then the resulting suspension was filtered and the collected solids washed with 100 mL of 5:1 hexane/ethyl acetate. The filtrate was concentrated on a rotary evaporator to give a pale yellow solid. The crude product was chromatographed over silica gel using 40% acetone/60% hexane as eluent to give the product (14.09 g) as a colorless solid.

ii) Pre-Formed Ylide Generation and Reaction in Presence of LiBr:

To a stirred suspension of allyltriphenyl phosphonium bromide (7.67 g, 20 mmol) in THF (20 mL) being cooled to 0° C., was added a solution of KOBu$^t$ in tetrahydrofuran (20 mL, 20 mmol, 1 M solution.). Stirring was continued at this temperature for 30 minutes and a solution of LiBr in THF (10 mL, 10 mmol, 1 M solution) was added. The reaction mixture was then stirred for 30 minutes and a solution of acetyl CsA-aldehyde (4.93 g, 4 mmol) in THF (10 mL) was added through a cannula. After stirring for 15 minutes at room temperature, the reaction mixture was quenched with saturated NH$_4$Cl solution (25 mL). Workup and chromatography as above furnished acetylated ISA$_{TX}$247 as a colorless solid (3.5 g).

Example 4

Preparation of ISA$_{TX}$247

Acetyl ISA$_{TX}$247 (14.6 g, 11.62 mmol) was dissolved in 340 mL of methanol and then 135 mL deionized water added. Potassium carbonate (13.36 g, 96.66 mmol) was added and the mixture stirred at room temperature for 24 to 48 hours until the reaction was complete. Most of the methanol was evaporated and then 250 mL ethyl acetate was added with stirring. A 10% aqueous citric acid solution (120 mL) was slowly added and then the ethyl acetate phase separated. The aqueous phase was extracted with an additional 200 mL portion of ethyl acetate. The combined ethyl acetate extracts were washed sequentially with 150 mL deionized water, 100 mL 10% aqueous citric acid solution and 150 mL saturated aqueous sodium chloride and then dried over MgSO$_4$. The ethyl acetate was evaporated to give a pale yellow solid. The crude product was chromatographed over silica gel using 40% acetone/60% hexane as eluent to give ISA$_{TX}$247 (10.51 g, 75%) as a colorless solid. ISA$_{TX}$247 contains 45-50% E-isomer and 50-55% Z-isomer.

The products in Examples 1-4 were characterized by mass spectrometry and/or nuclear magnetic resonance spectroscopy.

Example 5

Preparation of Acetyl-n-bromocyclosporin A

Acetyl Cyclosporin A (41.48 g, 33.3 mmol) prepared as in Example 1, N-bromosuccinimide (10.39 g, 58.4 mmol) and azo-bis-isobutyronitrile (1.09 g, 6.67 mmol) were dissolved in 250 mL of carbon tetrachloride and the resulting mixture heated to reflux for 2.5 hours. The mixture was cooled and the solvent evaporated. The residue was treated with 350 mL diethyl ether and filtered to remove the insoluble material. The filtrate was washed sequentially with 150 mL water and 150 mL brine, then dried over magnesium sulfate and the solvent evaporated. The crude material was chromatographed on silica gel with acetone/hexane (2:3) to give 28.57 g (65%) of acetyl-γ-bromocylosporin A as a yellow solid.

Example 6

Preparation of Triphenylphosphonium Bromide of Acetyl Cyclosporin A

Acetyl-γ-bromocylosporin A (28.55 g, 21.6 mmol) and triphenylphosphine (7.55 g, 28.8 mmol) were dissolved in 210 mL of toluene and the resulting solution heated to 100° C. for 21 hours. The solution was cooled and the toluene evaporated. The resulting oily, semi-solid was treated with 250 mL of hexane/ether (1:4), mixed thoroughly and the solvent decanted off. This process was repeated 3 more times with 150 mL ether. The residue was then dissolved in 50 mL ethyl acetate and precipitated with 220 mL hexane. The resulting solid was then collected by filtration to give 22.5 g (66%) of triphenylphosphonium bromide of acetyl cyclosporin A as a tan-colored solid.

Example 7

Wittig Reaction

The triphenylphosphonium bromide of acetyl cyclosporin (100 mg, 0.06 mmol), an excess of 37% formaldehyde (0.25 mL) and toluene (2 mL) were stirred rapidly at room temperature. Aqueous sodium hydroxide as a 1N solution (2 mL) was added dropwise and stirring continued for 3.5 hours. The reaction mixture was diluted with ethyl acetate (20 mL) and water (10 mL). The ethyl acetate phase was separated, washed sequentially with water (10 mL) and brine (10 mL), dried over magnesium sulfate and the solvent evaporated. The crude material was chromatographed on silica gel with acetone/hexane (2:3) to give 70 mg (88%) of a mixture of (E) and (Z)-isomers of acetyl ISA$_{TX}$247 as a colorless solid.

Example 8

De-acetylation of the Wittig Reaction Product

The mixture of isomers from Example 7 (70 mg., 0.056 mmol) was dissolved in methanol (5 mL) and then water (1 mL) added. Potassium carbonate (75 mg) was added and the reaction stirred at room temperature for 19 hours. Most of the methanol was evaporated and 15 mL ethyl acetate added to the residue followed by 10 mL of 10% aqueous citric acid. The ethyl acetate phase was separated and the aqueous phase extracted with an additional 10 mL of ethyl acetate. The combined ethyl acetate extracts were washed sequentially with 10 mL water, 10 mL 10% aqueous citric acid and I OmL brine before drying over magnesium sulfate and evaporating the solvent. The crude material was chromatographed on silica gel with acetone/hexane (2:3) to give 37 mg (54%) of ISA$_{TX}$247 as a colorless solid containing about 85% E-isomer and about 15% Z-isomer.

The products in Examples 5-8 were characterized by mass spectrometry and/or nuclear magnetic resonance spectrometry.

Example 9

Preparation of the Geometrical Isomers of ISA$_{TX}$247

The cis- and trans-isomers of ISA$_{TX}$247 may be independently synthesized using the following reaction scheme. The sequence involves known metalation of allyltrimethylsilane, the electrophilic capture by a trimethylborate, followed by the hydrolysis and then transesterification to generate the intermediate trans-(trimethylsilyl)allylboronate ester. Allylboration of cyclosporine aldehyde furnished a boron intermediate, which is converted to the desired β-trimethylsilyl alcohol, by sequestration. The diastereoselectivity in the creation of new chiral centers is not determined at this stage due to removal of these centers at a later stage. It should be noted that the relative stereochemistry of the two centers in the β-trimethylsilyl alcohol is anti in agreement with expectations and is due to the trans double bond in the trans-(trimethylsilyl) boronate precursor.

Base-promoted elimination (Hudrlick et al., 1975) of β-trimethylsilyl alcohol furnished a composition enriched in acetyl-(Z)-1,3-diene while acid-promoted elimination gave a composition enriched in acetyl-(E)-1,3-diene. Deprotection leads to the respective diene alcohols, the (Z) and (E)-isomers of ISA$_{TX}$247, respectively.

An alternate approach to dienes utilizes the allylphosphoranes. Metalation of allyldiphenylphosphine and then transmetalation with Ti(OPr$^i$)$_4$ gives the titanium intermediate. Allyltitanation followed by stereospecific elimination would generate a composition enriched in the (Z)-diene.

On the other hand, when allyldiphenylphosphine oxide is subjected to a similar sequence (FIG. 8), the E-isomer is predominantly (75%) generated.

i) Allylboration of Acetyl CsA-CHO:

The (E)-1-trimethylsilyl-1-propene-3-boronate was prepared in accordance with previously reported methods (Ikeda et al., 1987). To a stirred solution of (E)-1-trimethylsilyl-1-propene-3-boronate (0.2 g, 0.832 mmol) in THF (3 mL) under nitrogen was added acetyl Cyclosporin A aldehyde (1.026 g, 0.832 mmol). The reaction mixture was monitored by high performance liquid chromatography (C-8 column, reverse phase) and stirred for a total period of 7 days. Then triethanolamine (0.196 g, 1.3 mmol) was added and stirring continued for a further period of 4 days. The β-trimethylsilyl alcohol was obtained by purification over a silica gel column. MS(ES) m/z 1368.9 (M+Na$^+$).

To a suspension of KH (3.5 mg, 26.4 μmol, 30% mineral oil dispersion washed with anhydrous hexanes) in anhydrous THF (1 mL) was added β-triethylsilyl alcohol (10 mg, 7.4 micromole) and stirred at room temperature for 10 min. The reaction mixture was diluted with diethyl ether (10 mL) and then washed with saturated NaHCO$_3$ solution (2×5 mL). Drying (Na$_2$SO$_4$) and solvent removal furnished the enriched (Z)-acetyl-1,3-diene. MS (ES) m/z 1294.8 (M+K$^+$).

ii) Allyltitanation of Acetyl CsA-CHO:

To a stirred and cooled (−78° C.) solution of allyldiphenylphosphine (0.54 g, 2.4 mmol) in anhydrous ThF (8 mL) was added t-BuLi (1.42 mL, 2.4 mmol, 1.7 M solution in pentane). The brick-red colored solution was stirred for 15 min at this temperature and then at 0° C. for 30 min. It was then cooled again to −78° C. and added Ti(OPr$^i$)$_4$ (0.71 mL, 2.4 mmol). The brown colored solution was stirred at this temperature for 15 minutes and then a solution of acetyl CsA-CHO (2.5 g, 2 mmol) in THF (10 mL) was added through a cannula. The pale-yellow colored solution was stirred for a further period of 30 minutes and then warmed to room temperature overnight. To the reaction mixture was added MeI (0.15 mL, 2.4 mmol) at 0° C. Stirring was continued for 1 h at this temperature and then at room temperature for 2 h. The reaction mixture was poured into ice-cold 1% HC (100 mL). The aqueous layer was extracted with EtOAc (3×50 mL). The combined organic extract was washed with water (2×25 mL) and brine (25 mL). Removal of solvent gave a yellow solid which was chromatographed over a column of silica gel. Elution with 1:3 acetone-hexanes mixture furnished the (Z)-enriched isomer of acetyl ISA$_{TX}$247. Deprotection as in Example 4 gave (Z)-enriched isomer of ISA$_{TX}$247 (Z/E ratio, 75:25).

Example 10

Preparation of an (E)-enriched Mixture of ISA$_{TX}$247 Isomers

To a solution of allyldiphenylphosphine oxide (1 mmol) and hexamethylphosphoramide (2 mmol) in tetrahydrofuran (5 mL) at −78° C. was added n-butyllithium (1 mmol, in hexanes). The mixture was stirred at −78° C. for 30 minutes. A solution of acetyl cyclosporin A aldehyde (0.8 mmol) in tetrahydrofuran (7 mL) was added and the reaction mixture allowed to gradually warm to room temperature and then stirred for 18 hours. The mixture was poured into ice-cold 1N hydrochloric acid (50 mL) and then extracted into ethyl acetate. The organic extract was washed with water, dried over magnesium sulfate and the solvent evaporated. The residue was chromatographed over silica gel using 25% acetone/75% hexanes as eluent to give.a mixture of the (E) and (Z)-isomers of acetyl ISA$_{TX}$247. Removal of the acetate protecting group as described in Example 4 gave an (E)-enriched mixture of the ISA$_{TX}$247 isomers. Proton nmr spectroscopy indicated that the mixture was comprised of 75% of the (E) and 25% of the (Z)-isomer of ISA$_{TX}$247. This reaction was also carried out according to Schlosser's modification (R. Liu, M. Schlosser, *Synlett*, 1996, 1195). To a stirred and cooled (−78° C.) solution of allyldiphenylphosphine oxide (1.21 g, 5 mmol) in THF (20 mL) was added n-BuLi (2 mL, 5 mmol, 2.5 M solution in hexanes). The red-colored solution was stirred for 40 minutes at −78° C. A solution of acetyl CsA-CHO (1.25 g, 1.02 mmol) in THF (12 mL) was then added through a cannula during 15 minutes. The reaction mixture was stirred at room temperature for 2 hours. Workup and chromatography as above gave acetyl ISA$_{TX}$247 (Z:E ratio, 40:60 by $^1$H NMR analysis).

Example 11

Preparation of Benzoyl-Protected Cyclosporin A

Cyclosporin A (6.01 g, 5 mmol) and 4-dimethylaminopyridine (305 mg, 2.5 mmol) were dissolved in pyridine (5 mL). Benzoic anhydride (3.4 g, 15 mmol) was added and the mixture stirred for 19 hours at 50° C. Additional benzoic anhydride (1.7 g, 7.5 mmol) and DMAP (305 mg, 2.5 mmol)-were added and stirring at 50° C. continued for another 24 hours. Benzoic anhydride (0.85 g, 3.8 mmol) was added and the reaction stirred for an additional 23 hours. The reaction mixture was then poured slowly into water with stirring. Precipitated Cyclosporin A benzoate was filtered off and washed with water. The collected cake was dissolved in a minimum volume of methanol and added to a 10% citric acid solution and stirred for I hour. The precipitated product was collected by filtration and washed with water until the pH of the filtrate reached that of the water. The solid Cyclosporin A benzoate was dried at 50° C. under vacuum to give a colorless solid.

Example 12

Preparation of Triethylsilyl ether-Protected Cyclosporin A

Cyclosporin A (3.606 g, 3 mmol) was dissolved in dry pyridine (8 mL) and then DMAP (122 mg, 1 mmol) was added. The reaction mixture was cooled to 0° C. and then triethylsilyl trifluoromethanesulfonate (3.6 mmol) added dropwise. The mixture was allowed to warm to room temperature and stirred overnight. The reaction mixture was then poured slowly into water with stirring. The precipitated triethylsilyl ether was filtered off and washed with water. The collected cake was dissolved in a minimum volume of methanol and added to a 5% citric acid solution and stirred for 30 minutes. The precipitated product was collected by filtration and washed with water until the pH of the filtrate reached that of the water. The solid triethylsilyl ether was dried at 50° C. under vacuum to give a colorless solid. Triisopropylsilyl and tert-butyldimethylsilyl protecting groups were also introduced by following an analogous procedure.

Example 13

Immunosuppressive Activity Using the Calcineurin Inhibition Assay

An indicator of the efficacy of cyclosporine A or a cyclosporine A derivative is its ability to inhibit the phosphatase activity of calcineurin. The calcineurin inhibition assay measures the activity of the drug at its site of action and as such is the direct in vitro assessment of the potency of cyclosporine A analogues (Fruman et al., 1992).

Figure 11:
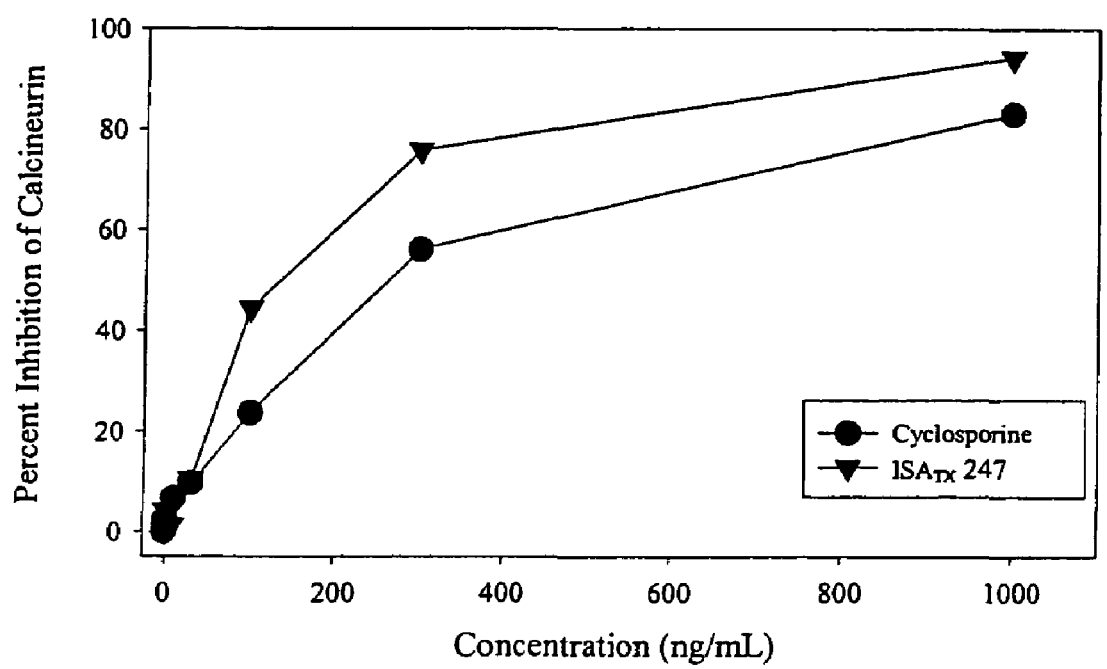
FIG. 11 provides the results of an assay which shows that the inhibition of calcineurin phosphatase activity by $ISA_{TX}247$ (45-50% of E-isomer and 50-55% of Z-isomer) was up to a 3-fold more potent (as determined by $IC_{50}$) as compared to cyclosporine A.

The immunosuppressive activity of $ISA_{TX}247$ (45-50% of E-isomer and 50-55% of Z-isomer) versus cyclosporine A has been assessed using the calcineurin (CN) inhibition assay. The results of this assay show that the inhibition of calcineurin phosphatase activity by $ISA_{TX}247$ (45-50% of Z-isomer and 50-55% of E-isomer) was up to a 3-fold more potent (as determined by $IC_{50}$) as compared to cyclosporine A (FIG. 11).

Figure 12:
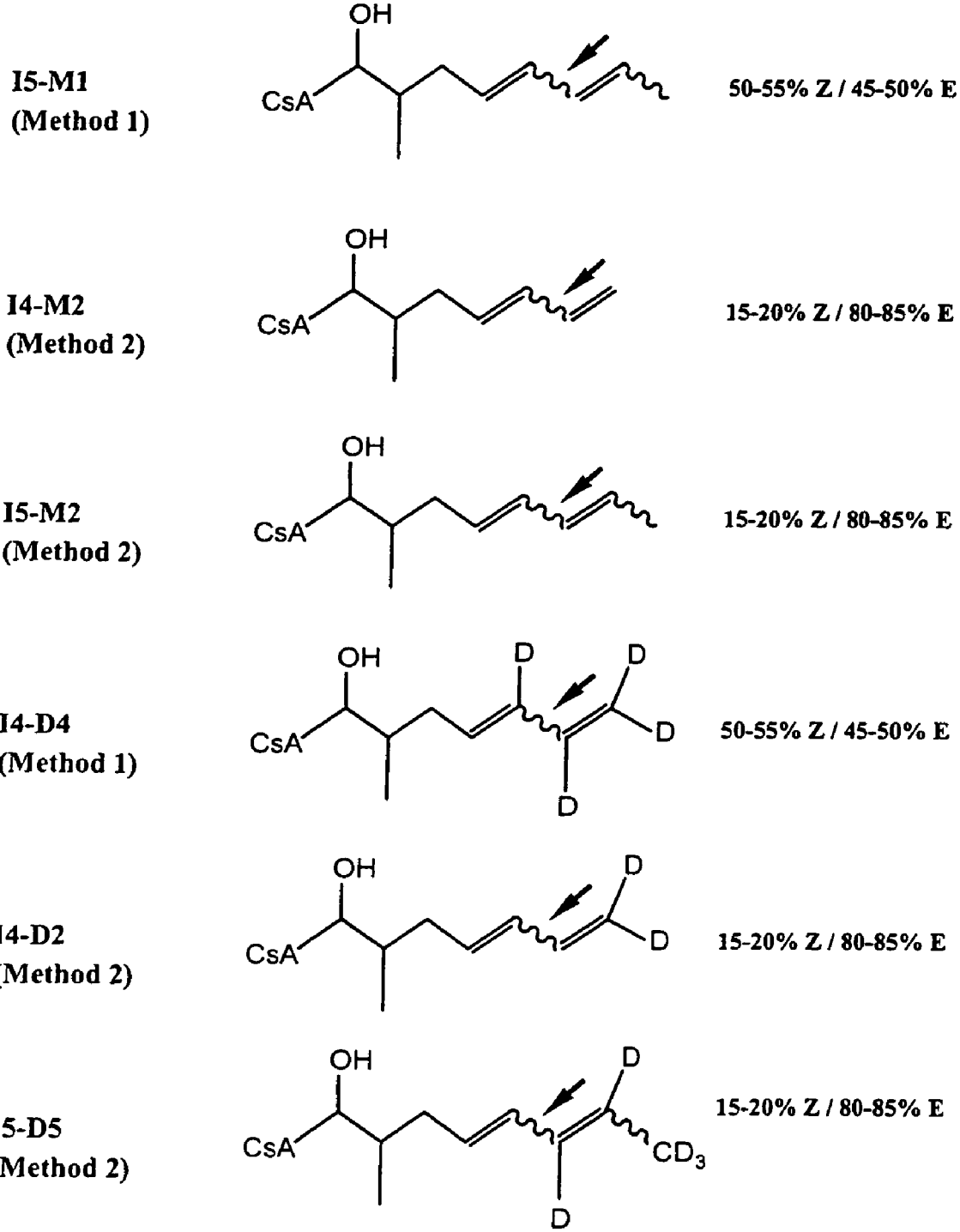
FIG. 12 sets forth the structure and isomeric composition of some deuterated and non-deuterated analogue isomeric mixtures.

The immunosuppressive activity of various deuterated and non-deuterated isomeric analogue mixtures versus cyclosporine A has been assessed using the calcineurin (CN) inhibition assay. The structure and isomeric composition of these analogues is set forth in FIG. 12. In FIG. 12, the designation "14" corresponds to the structure of $ISA_{TX}247$. 14-M2 denotes $ISA_{TX}247$ produced by the method described in Examples 5-8 (designated Method 2 in this figure). 14-D4 denotes deuterated $ISA_{TX}247$ produced by the method described in Examples 1-4. I4-D2 denotes deuterated $ISA_{TX}247$ produced by the method described in Examples 5-8. Other isomeric mixtures are as shown in the figure.

Figure 13:
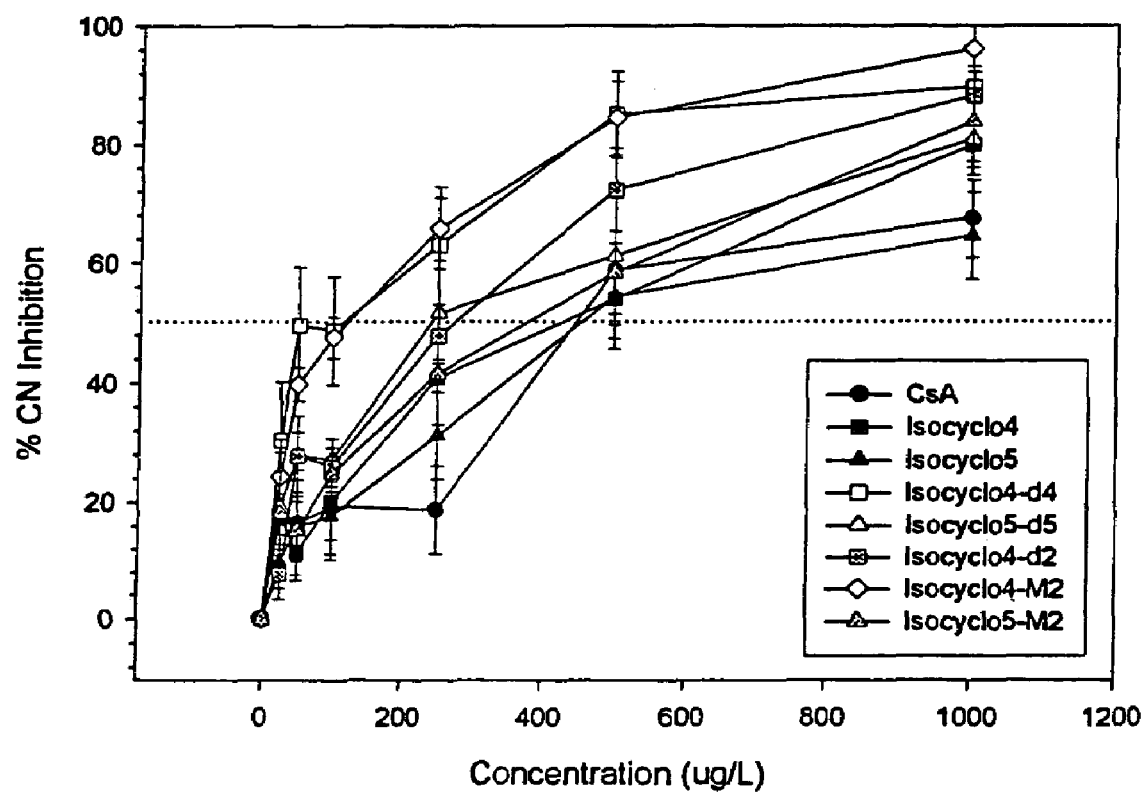
FIG. 13 provides the results of an assay which shows that the inhibition of calcineurin phosphatase activity by various deuterated and non-deuterated analogue isomeric mixtures was at least as potent (as determined by $IC_{50}$) as compared to cyclosporine A.

The results of this assay show that the inhibition of calcineurin phosphatase activity by these isomeric analogue mixtures was at least as potent (as determined by $IC_{50}$) as compared to cyclosporine A (FIG. 13). CsA denotes Cyclosporine A; Isocyclo4 denotes $ISA_{TX}247$ produced by the method-described in Examples 1-4. Isocyclo5 corresponds to 15-M1 of FIG. 12. Isocyclo4-d4 corresponds to 14-D4 of FIG. 12. Isocyclo5-d5 corresponds to 15-D5 of FIG. 12. Isocyclo4-d2 corresponds to 14-D2 of FIG. 12. Isocyclo4-M2 corresponds to 14-M2 of FIG. 12. Isocyclo5-m2 corresponds to 15-M5 of FIG. 12.

Example 14

Immunosuppressive Activity Using the Rat Heart Transplant Model

The efficacy of $ISA_{TX}247$ (45-50% of E-isomer and 50-55% of Z-isomer) in preventing the rejection of hearts transplanted between different strains of rats was assessed and compared to that of cyclosporine A. The rat heart transplant model has been the most frequently used model to assess the in vivo potency of new immunosuppressive drugs, as prolonged graft survival is difficult to achieve in this model due to immune rejection.

The procedure involved the heterotopic transplantation (to the abdominal aorta and inferior vena cava) of the heart from Wistar Furth rats to Lewis rats. Intraperitoneal injections of either cyclosporine A or an isomeric analogue mixture were given to the transplant recipient starting 3 days prior to transplantation and continuing for 30 days post-transplantation. If graft dysfunction was noted during the 30-day post-transplantation period, the animal was sacrificed. If the animal survived longer than 30 days post-transplantation, the test and control articles were discontinued and the animal was allowed to continue until graft dysfunction or up to 100 days post-transplantation.

The average survival rates for each group of recipient animals are summarized in Table 1. These results show that $ISA_{TX}247$ (45-50% of E-isomer and 50-55% of Z-isomer) at an optimal dose of 1.75 mg/kg/day increased survival time approximately 3-fold over Cyclosporine A. A number of animals receiving $ISA_{TX}247$ still had functioning grafts at 100 days post-transplant (70 days post discontinuation of dosing). These data demonstrate the immunosuppressive activity of this isomeric analogue mixture in preventing graft rejection.

TABLE 1

Effect of $ISA_{TX}247$ and Cyclosporine A Given by Intraperitoneal Administration on the Average Survival Times of Transplanted Rat Hearts [averaged from two separate studies, n 13]

| Dose (mg/kilogram/day) | Average Survival Time (days post-operative) Mean ± SEM (scanning electron microscope) | | |
|---|---|---|---|
| | Vehicle Control | Cyclosporine A | $ISA_{TX}247$ |
| 0 | 9 ± 1 | | |
| 0.5 | | 13[a] ± 4 | 11[a] ± 2 |
| 1.75 | | 18[b] ± 7 | 57[b] ± 32 |
| 3 | | 50[c] ± 8 | 55[c] ± 12 |

[a,c]Not significantly different
[b]Significantly different (p < 0.01)

The efficacy of various deuterated and non-deuterated isomeric analogue mixtures (structures given in FIG. 12) in preventing the rejection of hearts transplanted between different strains of rats was also assessed and compared to that of cyclosporine A. Doses were at 1.75 mg/kg/day for 30 days. Results are summarized in Table 2. These results show that the isomeric mixtures at 1.75 mg/kg/day increased survival time at least as much as Cyclosporine A and demonstrate the immunosuppressive activity of these isomeric analogue mixtures in preventing graft rejection.

TABLE 2

Effect of Various Isomeric Analogue Mixtures and Cyclosporine A Given by Intraperitoneal Administration at 1.75 mg/kg/day on the Average Survival Times of Transplanted Rat Hearts

| Test Compound | Average Survival Time (days post-operative) |
|---|---|
| Vehicle Control | 9 |
| Cyclosporine A | 20 |
| I5-M1 | 20 |
| I4-M2 | 20+ |
| I4-D2 | 30 |

Example 15

Immunosuppressive Activity in Islet Cell Allotransplantation

The ability of $ISA_{TX}247$ (45-50% of E-isomer and 50-55% of Z-isomer) versus cyclosporine A to prolong the survival of transplanted islet cells in a mouse model was investigated in a study involving the transplant of 500 islets from a CBA/J mouse into the renal capsule of diabetic Balb/c mouse recipients.

Following transplantation, $ISA_{TX}247$ or cyclosporine A was administered by intraperitoneal (i.p.) injection at a dose level of 0 (vehicle), 1.75, 10, 20, or 25 mg/kg/day for a total of 30 days. Blood glucose was monitored daily until the time of graft failure, as defined by a glucose level greater than 17 mmol/L on two consecutive days.

The results indicate that $ISA_{TX}247$ increased the length of graft survival by 40% at a dose of 20 mg/kg/day (Table 3). It was also noted that $ISA_{TX}247$ was less toxic than cyclosporine A as the dose level increased. This was especially apparent at the 25 mg/kg/day dose level.

TABLE 3

The Survival of Mouse Islet Allografts in Diabetic Mice Receiving Either $ISA_{TX}247$ or Cyclosporine A by Intraperitoneal Injection at a Dose Level of 1.75, 10, 20, or 25 mg/kg/day

| Dose (mg/kg/day) | Treatment | N | Median Survival | Mean Survival |
|---|---|---|---|---|
| 0 | Vehicle | 7 | 17 | 16.8 |
| 1.75 | CsA | 9 | 17 | 17.4 |
| 1.75 | ISA | 9 | 18 | 18.7 |
| 10 | CsA | 6 | 21 | 25.3 |
| 10 | ISA | 5 | 18 | 19.2 |
| 0 | Vehicle | 12 | 16 | 15.9 |
| 20 | CsA | 9 | 19 | 20.2 |
| 20 | ISA | 9 | >28 | >28 |
| 0 | Vehicle | 5 | 21 | 21.1 |
| 25 | CsA | 10 | ND* | ND* |
| 25 | ISA | 8 | 50 | 46.4 |

*7 out of the 10 animals in this group died of CsA toxicity. Therefore, only 3 animals completed in this group and no statistics were done.

Example 16

Immunosuppressive Activity in Arthritis

Over the course of the past three decades, three animal models of human rheumatoid arthritis have been extensively examined and widely employed in the preclinical screening and development for novel anti-rheumatic agents. These include the adjuvant-induced, collagen-induced, and antigen-induced arthritis models. The following studies were designed to evulate anti-inflammatory efficacy of $ISA_{TX}247$ (45-50% of E-isomer and 50-55% of Z-isomer) in both the collagen-induced arthritis model in the mouse and the antigen-induced arthritis model in the rabbit. The histopathology and immunopathology observed in these two models resemble the findings in the human disease. In both models, the efficacy of $ISA_{TX}247$ to prevent the onset of arthritis (prevention protocol) and to treat arthritis (treatment protocol) was examined. These studies support the immunosuppressive action of the claimed isomeric analogue mixtures.

A. Collagen-Induced Arthritis

Male DBA/I Lac J mice, kept under virus antibody free conditions, were immunized substaneously at 8 to 10 weeks of age with 100 microgram of chick type II collagen, emulsified in Freund's complete adjuvant. $ISA_{TX}247$, cyclosporine A, or vehicle (Chremophor EL/ethanol 72:28, volume/volume) were administered daily by intraperitoneal (i.p.) injection of 1- to 50-fold dilutions of stock drug (0.25, 0.5, or 1 mg/mL) into saline to yield concentrations of 0 (vehicle); 125, 250, or 500 µg/mouse for $ISA_{TX}247$; and 250, or 500 µg/mouse for cyclosporine A. Animals assigned to the prevention protocol (12/group) were dosed starting on the day of immunization with collagen (Day 0) until sacrifice on Day 40. Animals assigned to the treatment protocol (12/group) were dosed starting on the day of disease onset (~Day 28) until sacrifice on Day 38.

Evaluated parameters included mortality, serum creatinine, histology, and outcome assessments, such as clinical scoring (visual), hind paw swelling, histological scoring, erosion scoring, and immunohistochemistry.

Erosion scoring was done in a blinded manner by examining sagittal sections of the proximal interphalangeal (PIP) joint of the middle digit for the presence or absence of erosions (defined as demarcated defects in cartilage or bone filled with inflammatory tissue). This approach allowed for comparisons of the same joint. Previous studies have demonstrated erosions in >90% of untreated arthritic animals in this joint.

The results indicate that the negative erosion scores in the $ISA_{TX}247$ high-dose treatment group (500 µg/mouse) were significantly higher than the negative erosion scores in the vehicle treatment group (p<0.05). Both the mid-dose $ISA_{TX}247$ (250 µg/mouse) and high-dose cyclosporine A (500 µg/mouse) treatment groups had higher negative erosion scores as compared to the vehicle treatment group (p<<0.1). Furthermore, the low-dose $ISA_{TX}247$ (125 µg/mouse) and mid-dose cyclosporine A control (250 µg/mouse) treatment groups have higher, although not statistically significant, negative erosion scores when compared to the vehicle control group.

The only treatment to significantly prevent the development of joint erosions was $ISA_{TX}247$ at 500 µg/mouse. This significant reduction in the proportion of the PIP joints showing erosive changes in the $ISA_{TX}247$-treated mice relative to the vehicle control group mice demonstrates that $ISA_{TX}247$ has disease-modifying properties.

B. Antigen-Induced Arthritis

New Zealand White rabbits, maintained under specific pathogen free conditions, were immunized with 10 mg of ovalbumin in saline emulsified with Freund's complete adjuvant that was given intramuscularly and subcutaneously into several sites in the nape of the neck. Fourteen days later, all animals started receiving 2 daily intra-articular injections of 5 mg ovalbumin and 65 ng of human recombinant transforming growth factor 2 in saline.

ISA$_{TX}$247, cyclosporine A, or vehicle (Chremophor EL/ethanol 72:28, V/V) were administered daily by subcutaneous injection of 1- to 4-fold dilutions of stock drug (in vehicle) into saline to yield concentrations of O (vehicle); 2.5, 5.0, or 10 mg/kg/day for ISA$_{TX}$247; and 5.0, 10, or 15 mg/kg/day for cyclosporine A. Animals assigned to the prevention protocol (8/group) were dosed starting on the day of immunization with ovalbumin (Day 0) until sacrifice on Day 42. Animals assigned to the treatment protocol (8/group) were dosed starting on the day of disease onset (~Day 28) until sacrifice on Day 42.

Evaluated parameters included mortality, body weight, serum creatinine, histology, and outcome assessments such as knee joint swelling, synovial fluid counts, gross postmortem analysis, and histology.

A significant decrease in synovial histopathological scores was observed in ISA$_{TX}$247 (P 0.05) and cyclosporine A (P 0.05) animals after 28 days of therapy (prevention protocol) compared to vehicle control animals. This was accompanied by significant reductions in synovial fluid counts (ISA$_{TX}$247, P 0.05; cyclosporine A, P 0.05). Significant amelioration in synovial histopathological scores of animals with established arthritis was also evident following 14 days of treatment with ISA$_{TX}$247 (P 0.05) and cyclosporine A (P 0.05) compared to vehicle controls (treatment protocol). A significant reduction in macroscopic arthritis score was evident in ISA$_{TX}$247 (P=0.01), but not in cyclosporine A treated animals. Treatment was well tolerated with no significant toxicity upon analysis of serum creatinine or post-mortem histology.

The data show that ISA$_{TX}$247 is equivalent or potentially more potent than cyclosporine A in the treatment and prevention of rheumatoid arthritis in an antigen-induced arthritis model in the rabbit.

Example 17

Pharmacokinetic and Toxicokinetic Properties

The pharmacokinetic and toxicokinetic parameters of ISA$_{TX}$247 (45-50% of E-isomer and 50-55% of Z-isomer) and cyclosporine A were tested in a rabbit model. The rabbit has also been used as a model to study cyclosporine A nephrotoxicity, but far less frequently than the rat. Studies have found that cyclosporine A administered to the rabbit causes structural and functional changes at a dose not only lower than has been previously reported in other animal models, but also within at least the upper level of the therapeutic range in humans (Thliveris et al., 1991, 1994). Also, the finding of interstitial fibrosis and arteriolopathy, in addition to the cytological changes in the tubules, suggests that the rabbit is a more appropriate model to study nephrotoxicity, since these structural entities are hallmarks of nephrotoxicity observed in humans. ISA$_{TX}$247 was administered intravenously (i.v.) for the first 7 days and subcutaneously (s.c.) for an additional 23 days according to the following schedule.

TABLE 4

The Dose Administration Schedule for the Investigation of the Pharmacokinetic and Toxicokinetic Properties of ISA$_{TX}$247 in the Rabbit Model

| Treatment Group | Days 1-7: i.v. Dose (mg/kg) | Days 8-30: s.c. Dose (mg/kg) | Number of Animals Males | Number of Animals Females |
|---|---|---|---|---|
| 1. Vehicle Control | 0 | 0 | 4 | 4 |
| 2. Cyclosporine A control | 10 | 10 | 6 | 6 |
| 3. Low-Dose | 5 | 5 | 0 | 2 |
| 4. Medium-Dose | 10 | 10 | 4 | 4 |
| 5. High-Dose | 15 | 15 | 4 | 4 |

Pathogen free rabbits (SPF) were used to ensure any renal changes observed were due to the effect of ISA$_{TX}$247 and not due to pathogens. On Days 1 and 7, blood samples were collected prior to drug administration and at 0.5, 1, 2, 4, 8, 12, 18, and 24 hours post-dose to generate a pharmacokinetic profile. Other evaluated parameters included clinical observations, body weight, food consumption, hematology, clinical chemistry, gross pathology, and histopathological examination of selected tissues/organs.

Blood samples were analyzed via high performance liquid chromatography coupled with mass spectrometry (LCMS). Table 5 below summarizes the average pharmacokinetic parameters in rabbits that received 10 mg/kg of cyclosporine A or ISA$_{TX}$247.

TABLE 5

Pharmacokinetic Parameters of Intravenously Administered Cyclosporine A and ISA$_{TX}$247 in Male Rabbits Receiving 10 mg/kg/day. Results expressed as mean ± SD

| Measured Parameter | Cyclosporine A Day 1 | Cyclosporine A Day 7 | ISA$_{TX}$247 Day 1 | ISA$_{TX}$247 Day 7 |
|---|---|---|---|---|
| $t_{max}$ (hours) | 0.5 | 0.5 | 0.5 | 0.5 |
| $C_{max}$ (μg/L) | 1954 ± 320 | 2171 ± 612 | 1915 ± 149 | 1959 ± 470 |
| t½ (hours) | 7.4 ± 2.8 | 9.0 ± 4.0 | 7.4 ± 1.7 | 9.2 ± 1.1 |
| Area under the curve (μg · hr/L) | 6697 ± 1717 | 6685 ± 1247 | 5659 ± 1309 | 5697 ± 1373 |

There were no statistically significantly differences between the pharmacokinetic parameters of cyclosporine A and ISA$_{TX}$247 in male rabbits receiving 10 mg/kg/day. The pharmacokinetic parameters of ISA$_{TX}$247 in female rabbits receiving the same dose were not significantly different from that observed in the male rabbits, with the exception of maximum concentration on Day 7.

No significant changes were noted in the hematological parameters of rabbits receiving a vehicle control, cyclosporine A, or ISA$_{TX}$247. A difference was noted in the creatinine levels in the various groups over the course of the study, as is shown in Table 6 below. These differences indicated that cyclosporine A had a significantly greater negative effect on the kidneys than either the vehicle control or ISA$_{TX}$247. It should be noted that even at a 50% higher dose, 15 mg/kg/day, as compared to 10 mg/kg/day cyclosporine A, ISA$_{TX}$247 did not result in any significant increase in serum creatinine levels.

TABLE 6

Percent Change in Serum Creatinine Levels Over Baseline in Male Rabbits Receiving Vehicle, Cyclosporine A, or ISA$_{TX}$247 for 30 Days

| Treatment Group | Day 15 | Day 30 |
| --- | --- | --- |
| Vehicle | +6% | −3% |
| Cyclosporine A (10 mg/kg) | +22% | +33% |
| ISA$_{TX}$247 (10 mg/kg) | +1% | +10% |
| ISA$_{TX}$247 (15 mg/kg) | −19% | −11% |

Examination of organs in all rabbits receiving the vehicle control, 10 mg/kg cyclosporine A, 5 mg/kg ISA$_{TX}$247, or 10 mg/kg ISA$_{TX}$247 revealed no significant abnormalities. This was especially true for the kidneys, in which no evidence of interstitial fibrosis, normally seen in cyclosporine A-treated animals (Thliveris et al., 1991, 1994) was noted. In male rabbits that received 15 mg/kg ISA$_{TX}$247, a decrease in spermatogenesis was noted. No changes were noted in the 3 female rabbits that completed the study at this dose of 15 mg/kg ISA$_{TX}$247.

Example 18

Immunosuppressive Effects of ISA$_{TX}$247

Whole blood from cynomolgous monkeys (n=4) was incubated with ISA$_{TX}$247 or cyclosporine and stimulated with different mitogens in culture medium. Lymphocyte proliferation was assessed by tritium-labeled thymidine incorporation and by flow-cytometric analysis of expression of proliferating cell nuclear antigen (PCNA) on cells in SG$_2$M phase. Flow cytometry was also used to assess production of intracellular cytokines by T cells and expression of T lymphocyte activation antigens. The EC$_{50}$ (concentration of drug necessary to attain 50% of the maximum effect) was subsequently calculated using the WinNonlin™ software. Results showed that lymphocyte proliferation, cytokine production, and expression of T cell surface antigens were inhibited more potently by ISA$_{TX}$247 than by cyclosporine, as shown by the EC$_{50}$ (expressed in ng/mL) set forth in Table 7 below.

TABLE 7

| Parameter | ISA$_{TX}$247 | Cyclosporine |
| --- | --- | --- |
| $^3$H-thymidine uptake | 160.54 | 565.52 |
| PCNA expression | 197.72 | 453.88 |
| IL-2 production | 103.35 | 504.80 |
| IFN- production | 102.67 | 465.65 |
| TNF- production | 90.58 | 508.29 |
| CD 71 expression | 149.84 | 486.82 |

TABLE 7-continued

| Parameter | ISA$_{TX}$247 | Cyclosporine |
| --- | --- | --- |
| CD 25 expression | 121.00 | 431.53 |
| CD 11 a expression | 204.40 | 598.90 |
| CD 95 expression | 129.98 | 392.97 |
| CD 154 expression | 160.87 | 975.10 |

Thus, using an ex vivo whole blood assay we have found that ISA$_{TX}$247 suppresses diverse immune functions 2.3-6 times more potently than cyclosporine.

Example 19

Wittig Reaction Using Tributyl Allyl Phosphonium Bromide

Potassium tert butoxide (0.31 g, 2.8 mmol) was dissolved in 20 mL of tetrahydrofuran. At about −40° C. tributyl allyl phosphonium bromide (0.99 g, 3.1 mmol) dissolved in 3 mL of tetrahydrofuran was slowly added. The resulting yellow mixture was stirred for about 10 minutes at about −40° C. before a solution of acetyl cyclosporin A aldehyde (1.5 g, 1.2 mmol) in 6 mL of tetrahydrofuran was slowly added. After stirring the yellow-orange reaction mixture for 1.5 hours the reaction was complete. For quenching the reaction mixture was transferred onto aqueous phosphoric acid (1.2 g, 1.0 mmol). The resulting aqueous solution was extracted with 100 mL of toluene followed by 50 mL of toluene. The combined organic layers were washed with water and concentrated under reduced pressure to dryness. The product, acetylated ISA$_{TX}$247, was obtained as a slightly yellow solid in approximately 90% yield. The isomer ratio was about 87% E-isomer and about 13% Z-isomer (as determined by $^1$H-NMR spectroscopy).

Example 20

Wittig Reaction Using Tributyl Allyl Phosphonium Bromide and a Lithium Base

Tributyl allyl phosphonium bromide (1.38 g, 4.3 mmol) was dissolved in a mixture of 20 mL of toluene and 3 mL of-tetrahydrofuran. At about −78° C. butyllithium (1.6 M in hexane, 2.43 mL, 3.9 mmol) was slowly added. The resulting yellow mixture was stirred for about 10 minutes at about −78° C. before a solution of acetyl cyclosporin A aldehyde (1.5 g, 1.2 mmol) in 6 mL of toluene was slowly added. After stirring the yellow-orange reaction mixture for 3.5 hours the reaction was quenched by transferring the reaction mixture onto a mixture of 50 mL toluene and aqueous phosphoric acid (0.25 g, 2.2 mmol). The resulting biphasic mixture was allowed to warm to ambient temperature before the two layers were separated. The toluene layer was washed with 20 mL water and concentrated under reduced pressure to dryness. The product, acetylated ISA$_{TX}$247, was obtained as a slightly yellow solid in approximately 80% yield. The isomer ratio was about 70% E-isomer and about 30% Z-isomer (as determined by $^1$H-NMR spectroscopy).

Example 21

Wittig Reaction Using Tributyl Allyl Phosphonium Bromide and a Lithium Base

Running SAP018 as described above but only at about −40° C. The experimental conditions of Example 20 were repeated, this time using a reaction temperature of about −40° C. Under these conditions the isomeric ratio of the isolated product, acetylated ISA$_{TX}$247, was about 74% by weight of the E-isomer, and to about 26% by weight of the Z-isomer, as determined by $^1$H-NMR-spectroscopy.

Example 22

Wittig Reaction Using Tributyl Allyl phosphonium Bromide

A solution of acetyl cyclosporin A aldehyde (1.5 g, 1.2 mmol) and tributyl allyl phosphonium bromide (0.99 g, 3.1 mmol) in 15 mL of tetrahydrofuran was cooled to about −80° C. Potassium tert-butoxide (0.19 g, 1.7 mmol) dissolved in 9 mL of tetrahydrofuran was slowly added. The resulting yellow mixture was stirred for one hour at about −80° C. to complete the reaction before a solution of 6 mL of tetrahydrofuran was slowly added. After stirring the yellow-orange reaction mixture for 1.5 hours the reaction was complete. For quenching the reaction mixture aqueous phosphoric acid (0.15 g, 1.3 mmol) was added. The resulting mixture was concentrated and the residue was dissolved in 5 mL of methanol. Then the mixture was slowing added to 5 mL of water. The resulting precipitate was filtered, washed with 4 mL of methanol/water (1/1), and dried in vacuo. The product, acetylated ISA$_{TX}$247, was obtained as a colorless solid in approximately 90% yield. The isomer ratio was about 91% by weight E-isomer and 9% by weight Z-isomer (determined by $^1$H-NMR-spectroscopy).

Example 23

Ozonolysis of Acetyl CsA

A solution of acetyl cyclosporin A (15 g, 12.1 mmol) in 200 mL of methanol was ozonised at −78° C. using a Sander ozone generator at about 1.1 bar with a current flow of 300 L O$_2$/hour until the reaction was complete (about 5 minutes). The solution was gassed with argon and quenched with dimethylsulfide dissolved in methanol. For completing the reduction the mixture was stirred overnight at room temperature. After concentration to about 50 mL the solution was slowly added to 500 mL of water. The resulting precipitate was filtered, washed with 60 mL of water and dried in vacuo. The product, acetylated CsA aldehyde, was obtained as a colorless solid in approximately 95% yield and a purity of about 98% (determined by HPLC).

Example 24

Preparation of Trimethylsilyl-Protected Cyclosporine A

Cyclosporine A (40 g, 1 equivalent) was dissolved in dichloromethane (100 ml) at 30° C. N,N-bis-(trimethylsilyl) urea (1.1 equivalent) was added. After 5 minutes stirring at 30° C., p-toluenesulfonic acid (0.02 equivalents) was added. The reaction mixture was heated at reflux until completion of the reaction, as measured by thin layer chromatography (TLC), high pressure or high performance liquid chromatography (HPLC) or mass spectroctrometry (MS) and then cooled to room temperature. Half saturated aqueous sodium bicarbonate solution (100 ml) was added. The aqueous phase was separated and re-extracted with dichloromethane. The combined organic phases were dried over anhydrous Na$_2$SO$_4$ and filtered. The solvent was removed under reduced pressure providing the crude trimethylsilyl-protected Cyclosporine A.

Example 25

Preparation of Trimethylsilyl-Protected Cyclosporine A Aldehyde

Trimethysilyl-protected Cyclosporine A (5 g, 1 equivalent) was dissolved in dichloromethane (50 ml). The solution was then cooled to a temperature of about −78° C., after which ozone was bubbled through the solution until the appearance of a blue color. Next, argon was bubbled through the solution until a colorless solution was obtained in order to remove excess ozone it became colorless; this step was carried out to remove excess ozone. Triethylamine (5 equivalents) was added and the reaction mixture was stirred at room temperature for 17 hours. The trimethylsilyl-protected Cyclosporine A aldehyde was obtained after aqueous work-up.

Example 26

Preparation of a 3:1 Mixture of Z to E Double Bond Isomers of Trimethylsilyl-Protected Cyclosporine A Diene Via Wittig Reactions To a mixture of potassium tert-butoxide (3 equivalents) and allyltriphenylphosphonium bromide (2 equivalents) in toluene (10 ml) previously stirred for 60 minutes, was added the trimethylsilyl-protected Cyclosporine A aldehyde (1 g, 1 equivalent). Work-up of the reaction mixture after 1. hour reaction at room temperature provided a 3:1 mixture (by NMR) of Z and E double bond isomers of the trimethylsilyl-protected Cyclosporine A diene.

Example 27

Preparation of a 1:1 Mixture of Z to E Double Bond Isomers of Trimethylsilyl-Protected Cyclosporine A Diene Via Wittig Reactions The trimethylsilyl-protected Cyclosporine A aldehyde (2.5 g) was dissolved in 25 ml of toluene and treated with 1N aqueous sodium hydroxide solution (10 equivalents). The reaction mixture was vigorously stirred and allyltriphenylphosphonium bromide (7.5 equivalents, portionwise) was added. Work-up of the reaction mixture after several hours reaction at room temperature provided a ca 1:1 mixture (by NMR) of Z and E double bond isomers of the trimethylsilyl-protected Cyclosporine A diene.

Example 28

Preparation of a 1:2 Mixture of Z to E Double Bond Isomers of Trimethylsilyl-Protected Cyclosporine A Diene Via Wittig Reactions The trimethylsilyl-protected Cyclosporine A aldehyde (1 g) was dissolved in 5 ml of toluene together with potassium carbonate (1.5 equivalent) and allyltriphenylphosphonium bromide (1.5 equivalent). Work-up of the reaction mixture after 4 hours reaction at reflux under vigorous stirring provided a ca 1:2 mixture (by NMR) of Z and E double bond isomers of the trimethylsilyl-protected Cyclosporine A diene.

Example 29

Preparation of a 1:3 Mixture of Z to E Double Bond Isomers of Trimethylsilyl-Protected Cyclosporine A Diene Via Wittig Reactions Allyltributylphosphonium bromide (3 equivalents, prepared from allylbromide and tributylphosphine) was dissolved in THF (3.5 ml). Toluene (7.5 ml) was added followed by potassium tert-butoxide (4 equivalents). After 1 hour stirring at room temperature, the solution was cooled to ca −30° C. A solution of the trimethylsilyl-protected Cyclosporine A aldehyde (1 g, 1 equivalent) in toluene (5 mL) was added dropwise. After 45 minutes at about −30° C., the reaction mixture was worked up, providing an approximately 1:3 mixture (by NMR) of Z and E double bond isomers of the trimethylsilyl-protected Cyclosporine A diene.

The following two examples, Examples 30 and 31, are directed to allylmetallations.

Example 30

Preparation of Acetyl-Protected Cyclosporine A β-trimethylsilylalcohol

To a solution of allyltrimethylsilane (10.1 equivalents) in THF (15 ml) was added butyl lithium (1.6 M in hexanes, 10 equivalents) at room temperature. After 30 minutes reaction, the solution was cooled to −75° C., and treated with diethyl-B-methoxyborane (10.1 equivalents). After 1 hour, borontrifluoride diethylether complex (10.1 equivalents) was added to generate the B-(γ-trimethylsilyl-allyl)-diethylborane reagent. After 1 hour, a solution of acetyl-protected Cyclosporine A aldehyde (5 g, 1 equivalent) in THF (15 ml) was added dropwise. After 20 minutes, the reaction mixture was warmed to −10° C. and a saturated aqueous NH$_4$Cl solution was added. After stirring one hour at room temperature, water (45 ml) was added and the reaction mixture was extracted 3 times with 25 ml ethyl acetate. The organic phases were washed sequentially with water (25 ml) and a saturated aqueous NH4Cl solution (25 ml). The combined organic phases were dried over Na$_2$SO$_4$, filtered, and concentrated under reduced pressure. The crude product was chromatographed (Silicagel, dichloromethane/methanol or ethyl acetate/heptane) to yield the acetyl-protected Cyclosporine A β-trimethylsilylalcohol.

Example 31

Preparation of Trimethylsilyl-Protected Cyclosporine A β-trimethylsilylalcohol

To a solution of allyltrimethylsilane (10.1 equivalent) in THF (15 ml), was added butyl lithium (1.6 M in hexanes, 10 equivalents) at room temperature. After allowing the reaction to proceed for about 30 minutes, the solution was cooled to −65° C., and treated with diethyl-B-methoxyborane (10.1 equivalents). After 1 hour, borontrifluoride diethylether complex (10.1 equivalents) was added to generate the B-(-γ-trimethylsilyl-allyl)-diethylborane reagent. After 1 hour, a solution of trimethylsilyl-protected Cyclosporine A aldehyde (5 g, 1 equivalent) in THF (15 ml) was added dropwise. After 15 minutes, the reaction mixture was warmed to 10° C. and a saturated aqueous NH$_4$Cl solution was added. After [1 hour] stirring for one hour at room temperature, water (12.5 ml) and saturated NaHCO$_3$ (25 ml) were added. The reaction mixture was extracted twice with 25 ml methyl-t-butyl ether. The organic phases were washed twice sequentially with water (2×25 ml) and a saturated aqueous NaCl solution (25 ml). The combined organic phases were dried over Na$_2$SO$_4$, filtered, and concentrated under reduced pressure. The crude product was chromatographed (Silicagel, heptane/ethyl acetate) to yield the trimethylsilyl-protected Cyclosporine A β-trimethylsilylalcohol.

The following three examples, Examples 32, 33, and 34, are directed to Peterson elimination reactions.

Example 32

Preparation of E-acetyl-protected Cyclosporine A Diene

The acetyl-protected Cyclosporine A β-trimethylsilylalcohol (100 mg, 1 equivalent) was dissolved in THF (1 ml). Concentrated H$_2$SO$_4$ (10 µL) was added and the reaction mixture was stirred overnight at room temperature. Water (10 ml) was added and the reaction mixture was extracted with dichloromethane (10 ml). The aqueous phase was re-extracted with dichloromethane (10 ml). The combined organic phases were dried over Na$_2$SO$_4$, filtered and concentrated under reduced pressure to give the acetyl-protected Cyclosporine A diene (acetyl-protected ISA$_{TX}$247). The crude product was crystallized from methyl-t-butyl ether/THF and then recrystallized from methyl-t-butyl ether/DCM to give acetyl-protected Cyclosporine A diene (acetyl-protected ISA$_{TX}$247) as a 99-97%:1-3% mixture of E and Z double bond isomers (by 400 MHz NMR, 2% error of measurement).

Hydrolysis of E-acetyl-protected Cyclosporine A diene was conducted as following: Acetyl Cyclosporine A diene (4 g, 1 equivalent) was dissolved in methanol (80 ml) and water (32 ml). Potassium carbonate (3.65 g, 8.3 equivalent) was added. After stirring for 15 hours at room temperature, the reaction mixture was heated up to 40° C. for 4 hours. The reaction mixture was concentrated under reduced pressure and the residue was taken up in ethyl acetate (70 ml). Aqueous citric acid solution 15% (30 ml) was slowly added followed by water (10 ml). The aqueous layer was separated and re-extracted with ethyl acetate (56 ml). The organic phases were washed with water (30 ml), 15% citric acid solution (40 ml) and saturated NaCl solution (30 ml). The organic layers were combined, dried over Na$_2$SP$_4$ and concentrated under reduced pressure to give Cyclosporine A diene (ISA$_{TX}$247).

Example 33

Preparation of Z-trimethyisilyl-Protected Cyclosporine A Diene and Its Conversion to Z-Cyclosporine A Diene (ISA$_{TX}$247

The trimethylsilyl-protected Cyclosporine A β-trimethylsilylalcohol (2 g, 1 equivalent) was dissolved in THF (20 ml). The solution was cooled to 0-2° C. and potassium t-butoxide (4 equivalents) was added. After 1.5 hours reaction, ethyl acetate (20 ml) and water (40 ml) were added. The aqueous layer was separated and re-extracted with ethyl acetate (20 ml). The organic phases were washed with a saturated aqueous NaCl solution (20 ml). The combined organic phases were dried over Na$_2$SO$_4$, filtered, and concentrated under reduced pressure to give a mixture of Z-trimethylsilyl-protected Cyclosporine A diene (trimethylsilyl-protected ISA$_{TX}$247), and Z-Cyclosporine A diene (the Z-isomer of ISA$_{TX}$247). The desilylation was completed by dissolving the crude product mixture in methanol (10% by weight in the solution) and adding a 1 M aqueous hydrochloric acid solution (1 equivalent). After 15 minutes at room temperature, water and ethyl acetate were added. The aqueous layer was separated and re-extracted with ethyl acetate. The organic phases were washed with a saturated aqueous NaCl solution. The combined organic phases were dried over Na$_2$SO$_4$, filtered, and concentrated under reduced pressure, providing Cyclosporine A diene (ISA$_{TX}$247) as a 94:6 mixture of Z and E double bond isomers (by NMR).

Example 34

Preparation of E-Cyclosporine A Diene (ISA$_{TX}$47)

The trimethylsilyl-protected Cyclosporine A β-trimethylsilylalcohol (500 mg, 1 equivalent) was dissolved in dichloromethane. This solution was cooled within a range of about 0-2° C., and treated with borontrifluoride diethylether complex (5 equivalents). After 1 hour, water (20 ml) and dichloromethane (20 ml) were added. The organic layer was separated and washed with water (20 ml), dried over Na$_2$SO$_4$, filtered, and concentrated under reduced pressure to provide directly Cyclosporine A diene (ISA$_{TX}$247) as a 91:9 mixture by weight of the E and Z double bond isomers (by NMR).

Example 35

Deprotection of Trimethylsilyl-Protected Cyclosporine A Diene

Trimethylsilyl-protected Cyclosporine A diene was dissolved in methanol (10% by weight in the solution). This solution was treated with 1 M aqueous hydrochloric acid solution (1 equivalent). After 15 minutes at room temperature, water and ethyl acetate were added. The aqueous layer was separated and re-extracted with ethyl acetate. The organic phases were washed with a saturated aqueous NaCl solution. The combined organic phases were dried over Na$_2$SO$_4$, filtered and concentrated under reduced pressure, providing Cyclosporine A diene (ISA$_{TX}$247).

Example 36

Epoxidation of Acetyl Cyclosporin A

Acetyl cyclosporine A (2.0 g, 1.61 mmol) was dissolved in acetonitrile (30 mL). 1,3-Diacetoxy-acetone (0.14 g, 0.8 mmol) was added, followed by 0.0004 M aqueous ethylenediaminetetra-acetic acid disodium salt (20 mL) and sodium bicarbonate (0.405 g, 4.82 mmol). To the stirred mixture, oxone (43.8% KHSO$_5$) (2.23 g, 6.43 mmol) was added portionwise over 2 hours. The pH was maintained at 8.2 by constant addition of 1 N NaOH (total amount 6.4 mL) using a pH stat. The temperature was kept at 22-25° C. by occasional cooling using a cold water bath. After 2.5 hours the reaction mixture was quenched by a few drops of a sodium bisulfite solution. Water (100 mL) was added and the mixture was extracted twice with tert-butyl methyl ether (100 mL, then 75 mL). The organic extracts were washed with dilute aqueous sodium chloride (100 mL), combined, dried over Na$_2$SO$_4$, and concentrated to afford crude acetyl cyclosporin A epoxide (1.92 g, 95%; HPLC: 99.4% area) as a white solid foam.

Example 37

Preparation of Acetyl Cyclosporin A Aldehyde

Crude acetyl cyclosporin A epoxide (1.92 g, 1.52 mmol) was dissolved in acetonitrile (25 mL). Water (20 mL) was added, followed by sodium periodate (489 mg, 2.28 mmol) and 0.5 M sulfuric acid (3.05 mL, 1.52 mmol). The reaction mixture was stirred at 40° C. for 18 hours, then the excess sodium periodate was quenched by addition of aqueous sodium bisulfite. Dilute aqueous sodium chloride (100 mL) was added and the mixture was extracted twice with tert-butyl methyl ether (100 mL each). The organic extracts were washed with dilute aqueous sodium chloride (100 mL), combined, dried over Na$_2$SO$_4$, and concentrated to afford crude acetyl cyclosporin A aldehyde (1.74 g, 92%; HPLC: 95.7% area) as a white foam. The crude product was chromatographed over silica gel using 40% acetone/60% hexane as eluent to give the product (1.41 g, 71% based on acetyl cyclosporin A; HPLC: 100% area) as a white solid foam.

Example 38

Preparation of Acetyl Cyclosporin A Aldehyde Using a One-Pot Procedure

Acetyl cyclosporin A (2.0 g, 1.61 mmol) was dissolved in acetonitrile (30 mL). 1,3-Diacetoxy-acetone (0.084 g, 0.48 mmol) was added, followed by 0.0004 M aqueous ethylenediaminetetra-acetic acid disodium salt (20 mL) and sodium bicarbonate (0.405 g, 4.82 mmol). To the stirred mixture, oxone (43.8% KHSO$_5$) (1.67 g, 4.82 mmol) was added portionwise over 2 hours. The pH was maintained at 8.2 by constant addition of 1 N NaOH (total amount 3.4 mL) using a pH stat. The temperature was kept at 20-25° C. After 3.5 hours, 0.5 M sulfuric acid (5 mL, 2.5 mmol) was added to the reaction mixture, followed by a few drops of concentrated sulfuric acid, until pH 1.3 was reached. Then, sodium periodate (516 mg, 2.41 mmol) was added, and the reaction mixture was stirred at room temperature for 2 hours and at 40° C. for 22 hours. Water (100 mL) was added and the mixture was extracted twice with tert-butyl methyl ether (100 mL, then 75 mL). The organic extracts were washed with dilute aqueous sodium chloride (100 mL), combined, dried over Na$_2$SO$_4$, and concentrated to afford crude acetyl cyclosporin A aldehyde (1.9 g, 96%; HPLC: 83.4% area) as a white foam. The crude product was chromatographed over silica gel using 40% acetone/60% hexane as eluent to give the product (1.35 g, 68% based on acetyl cyclosporin A; HPLC: 100% area) as a white solid foam.

Example 39

(ISO): Wittig Reaction of Acetyl Cyclosporin A Aldehyde with 3-Dimethylaminopropyltriphenylphoslphorylidene The acetylated Cyclosporine A aldehyde 1 was reacted with the salt-free ylide 2 which was generated from the reaction of 3-dimethylaminopropyltriphenylphosphonium bromide with potassium hexamethyldisilazide (Corey, E. J. and Desai, M. C. *Tetrahedron Letters*, 1985, 26, 5747). Selective N-oxidation of the cis compound 3 was achieved using m-chloroperbenzoic acid at 0° C. Cope elimination of the N-oxide at elevated temperature in vacuo furnished the acetylated Z-isomer. Deprotection as described earlier furnished the Z-isomer of $ISA_{TX}$247. $^1H$ NMR (500 MHz) spectrum of this compound confirmed the Z-geometry by exhibiting a doublet of triplet at 3 6.58 with J values 16.99 and 10.5 Hz, characteristic of Z-isomer in a $ISA_{TX}$247 Z/E mixture. The isomeric purity is 99% since the doublet of a triplet characteristic of E-isomer in the mixture at δ 6.28 (J=17.5, 10.0 Hz) was not detectable.

To a stirred suspension of 3-dimethylaminopropyltriphosphonium bromide (2.5 g, 5.83 mmol) in anhydrous toluene (20 mL) was added potassium hexamethyldisilazide (11.6 mL, 5.8 mmol, 0.5M solution in toluene) through a syringe. After stirring for 1 h at room temperature, the red-colored solution was centrifuged and the supernatant transferred to a reaction flask through a cannula. To the solid was added anhydrous toluene (10 mL), stirred and centrifuged. The supernatant was transferred to the reaction flask and to the combined red-colored ylide was added OAc-CsA-CHO (1.44 g, 1.17 mmol). Stirring was continued for a further period of 2 h at room temperature when the color turned light-yellow. The reaction mixture was diluted with EtOAc (50 mL) and washed subsequently with saturated $NaHCO_3$ solution (50 mL) and brine (50 mL). Drying and solvent removal furnished a pale-yellow solid. Chromatography over a silica gel column and elution with acetone-hexanes mixture (gradient: 10 to 75% acetone and 90 to 25% hexanes) removed all phosphorous-related impurities. Further elution with acetone furnished desired product as a colorless solid (1.28 g, 84% yield). $^1H$ NMR (300 MHz, $CDCl_3$): 2.23 (s, 6H), 2.03 (s, 3H). $^{13}C$ NMR (300 MHz, $CDCl_3$): 129.33, 126.95; MS m/z: 1301 ($M^+$), 1324 ($M+Na^+$).

Conversion to N-Oxide

To a stirred and cooled (0° C.) solution of the dimethylamino compound obtained in the Wittig reaction (0.44 g, 0.34 mmol) in $CHCl_3$ (3 mL) was added a solution of m-CPBA (0.07 g, 0.405 mmol) in $CHCl_3$ (2 mL). After stirring for 30 min, dimethyl sulfide (0.5 mL) was added followed by $CH_2Cl_2$ (50 mL). Work-up by washing with $NaHCO_3$ solution (25 mL) and water (25 mL), drying and solvent removal furnished a solid (0.43 g). $^1H$ NMR (300 MHz, $CDCl_3$): 3.19 (s, 3H), 3.18 (s, 3H), 2.03 (s, 3H). $^{13}C$ NMR (300 MHz, $CDCl_3$): 131.89, 124.13; MS m/z: 1340 ($M+Na^+$).

Cope Elimination of N-Oxide. Preparation of (Z)-Isomer of Acetyl $ISA_{TX}$247

The N-oxide (350 mg) was stirred neat and heated at 100° C. in vacuo for 2 h. This was then passed through a column of silica gel. Elution with acetone-hexanes mixture (gradient, 5 to 25% acetone and 95 to 75% hexanes) furnished a colorless solid (314 mg). $^1H$ NMR (500 MHz, $CDCl_3$): 6.49 (dt, J=16.99, 10.5 Hz, 1H); $^{13}C$ NMR (400 MHz, $CDCl_3$): 132.20, 131.09, 129.70, 116.85; MS mz/z: 1279 ($M+Na^+$).

(Z)-Isomer of $ISA_{TX}$247

To a solution of (Z)-acetyl $ISA_{TX}$247 (50 mg) in MeOH (4 mL) was added water (1.5 mL) and $K_2CO_3$ (60 mg) and stirred for 48 h at room temperature. The reaction mixture was stripped off solvents and extracted with EtOAc (20 mL). The organic layer was washed with water (10 mL) and brine (10 mL). Drying and solvent removal furnished a colorless solid. $^1H$ NMR (500 MHz, $CDCl_3$): 6.58 (dt, J=16.99, 10.5 Hz, 1H); MS m/z: 1236.8 ($M+Na^+$). The resulting compound was Z-isomer of $ISA_{TX}$247. No measurable E-isomer was observed by NMR.

Although only preferred embodiments of the invention are specifically disclosed and described above, it will be appreciated that many modifications and variations of the present invention are possible in light of the above teachings and within the purview of the appended claims without departing from the spirit and intended scope of the invention.

We claim:

1. A composition comprising an isomeric mixture of a cyclosporine analogue modified at the 1-amino acid residue with a 1,3-diene substituent, wherein the isomeric mixture comprises about 90% to about 95% of the E-isomer and about 10% to about 5% of the Z-isomer, wherein the isomers are the isomers E- and Z- as specified below:

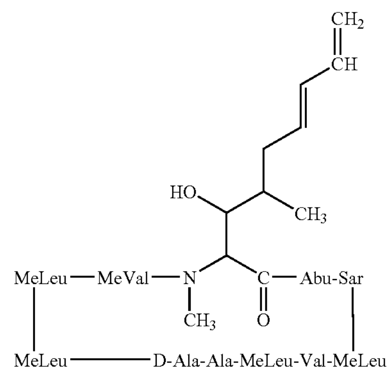

E-isomer

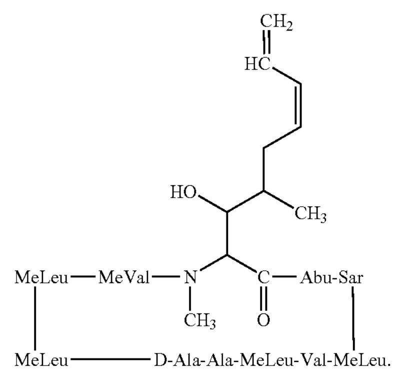

Z-isomer

2. A composition comprising an isomeric mixture of a cyclosporine analogue modified at the 1-amino acid residue with a 1,3-diene substituent, wherein the isomeric mixture comprises greater than or equal to about 95% of the E-isomer and less than or equal to about 5% of the Z-isomer, wherein the isomers are the isomers E- and Z- as specified below:

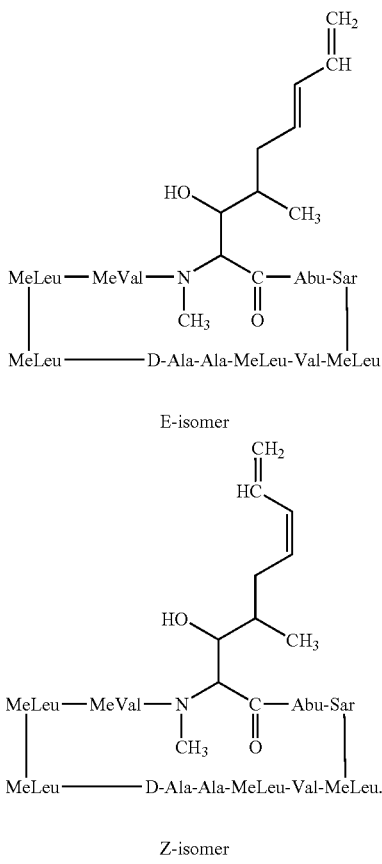

E-isomer

Z-isomer

3. A pharmaceutical composition comprising an isomeric cyclosporine analogue mixture according to claim 1 or 2 and a pharmaceutically acceptable excipient.

4. The pharmaceutical composition of claim 3, which comprises a gelatin capsule containing the isomeric analogue mixture, a liquid solution containing a surfactant, ethanol, a lipophilic and/or ampiphilic solvent.

5. The pharmaceutical composition of claim 4, which contains about 50 mg isomeric mixture.

6. The pharmaceutical composition of claim 3, which comprises a liquid solution containing a surfactant, ethanol, a lipophilic and/or an ampiphilic solvent.

7. The pharmaceutical composition of claim 6, which comprises d-alpha Tocopheryl polyethylene glycol 1000 succinate (vitamin E TPGS), medium chain triglyceride (MCT) oil, Tween 40, and ethanol.

8. The pharmaceutical composition of claim 7, which is in unit dosage form.

9. The pharmaceutical composition of claim 8, which contains from about 5 mg to about 500 mg of the isomeric mixture.

10. The pharmaceutical composition of claim 6, wherein the solution contains 50 mg/mL isomeric mixture.

11. The pharmaceutical composition of claim 3, which is formulated for oral administration.

12. The pharmaceutical composition of claim 3, wherein the pharmaceutical composition is formulated to provide an amount of isomeric cyclosporine analogue that is about 0.05 mg to about 50 mg per kilogram of body weight per day.

13. The pharmaceutical composition of claim 12, wherein the amount of isomeric cyclosporine analogue mixture is about 0.1 mg to about 10 mg per kilogram of body weight per day.

14. The pharmaceutical composition of claim 13, wherein the amount of isomeric cyclosporine analogue mixture is about 0.5 to about 10 mg/kg/day.

15. The pharmaceutical composition of claim 14, wherein the amount of an isomeric cyclosporine analogue mixture is about 2 to about 6 mg/kg/day and wherein the pharmaceutical composition is formulated to be administered orally twice daily.

16. The pharmaceutical composition of claim 15, wherein the amount of isomeric cyclosporine analogue mixture is about 0.5 to about 3 mg/kg/day and wherein the pharmaceutical composition is formulated to be administered orally, twice daily.

17. A method for producing immunosuppression comprising administering a therapeutically effective amount of the isomeric cyclosporine analogue mixture according to claim 1 or 2 to an animal.

18. The method of claim 17, wherein said animal is a human.

19. The method of claim 17, wherein the amount of the isomeric cyclosporine analogue mixture to be administered is about 0.05 mg to about 50 mg per kilogram of body weight per day.

20. The method of claim 19 wherein the amount of the isomeric cyclosporine analogue mixture to be administered is about 0.1 mg to about 10 mg per kilogram of body weight per day.

21. The method of claim 20, wherein the amount of the isomeric cyclosporine analogue mixture to be administered is about 0.5 to about 10 mg/kg/day.

22. The method of claim 21, wherein the amount of an isomeric cyclosporine analogue mixture to be administered is about 2 to about 6 mg/kg/day and wherein the pharmaceutical composition is formulated to be administered orally, twice daily.

23. The method of claim 21, wherein the amount of an isomeric cyclosporine analogue mixture to be administered is about 0.5 to about 3 mg/kg/day and wherein the pharmaceutical composition is formulated to be administered orally, twice daily.

24. The method of claim 17, wherein said immunosuppression is to treat or alleviate acute organ or tissue transplant rejection.

25. The method of claim 24, wherein said transplant rejection is selected from the group consisting of heart, lung, combined heart-lung, liver, kidney, pancreatic, skin, bowel, and corneal transplant rejection.

26. The method of claim 17, wherein said immunosuppression is to treat or alleviate T-cell mediated rejection.

27. The method of claim 17, wherein said immunosuppression is to treat or alleviate graft-versus-host disease.

28. The method of claim 27 wherein said disease follows bone marrow transplantation.

29. The method of claim 17, wherein said immunosuppression to treat or alleviate chronic rejection of a transplanted organ.

30. The method of claim 29, wherein said chronic rejection is graft vessel disease.

31. The method of claim 17, wherein said immunosuppression is to treat or alleviate xenograft rejection.

32. The method of claim 31, wherein said xenograft rejection is selected from the group consisting of acute, hyperacute and chronic rejection of an organ occurring when the organ donor is of a different species from the recipient.

33. The method of claim 32, wherein said xenograft rejection is rejection mediated by B-cells or antibody-mediated rejection.

34. The method of claim 17, wherein said immunosuppression is to treat or alleviate an autoimmune disease or condition or an inflammatory disease or condition.

35. The method of claim 34, wherein said disease or condition is selected from the group consisting of arthritis, rheumatoid arthritis, arthritis chronica progrediente, arthritis deformans and other rheumatic diseases.

36. The method of claim 34, wherein said disease or condition is selected from the group consisting of hematological disorders, hemolytic anemia, aplastic anemia, pure red cell anemia, idiopathic thrombocytopenia, systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, (autoimmune) inflammatory bowel disease, ulcerative colitis, Crohn's disease, endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca, vernal keratoconjunctivitis, interstitial lung fibrosis, psoriatic arthritis, glomerulonephritis, idiopathic nephrotic syndrome, minimal change nephropathy and juvenile dermatomyositis.

37. The method of claim 34, wherein said disease or condition is selected from the group consisting of psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullous acquisita, other inflammatory or allergic conditions of the skin, inflammatory conditions of the lungs and airways, asthma, allergies and pneumoconiosis.

38. The method of claim 17, wherein the immunosuppression is to prevent allograft or xenograft rejection.

39. The method of claim 38, wherein the rejection is rejection of kidney, heart, or liver.

40. A method of reducing the toxicity of an immunosuppressive cyclosporine analogue by preparing an isomeric mixture of claim 1 or 2 for use as an immunosuppressive agent, the mixture having reduced toxicity relative to Cyclosporine A.

41. The method of claim 40, wherein the immunosuppressive agent comprises the isomeric cyclosporine analogue mixture in an amount selected from the group consisting of about 0.05 mg to about 50 mg per kilogram of body weight per day; about 0.1 mg to about 10 mg per kilogram of body weight per day; about 0.5 to about 10 mg/kg/day; about 2 to about 6 mg/kg/day, administered orally twice a day; and about 0.5 to about 3 mg/kg/day, administered orally twice a day.

42. A method of increasing the efficacy of an immunosuppressive cyclosporine analogue by preparing an isomeric mixture of claim 1 or 2 for use as an immunosuppressive agent, the mixture having increased efficacy relative to Cyclosporine A.

43. The method of claim 42, wherein the immunosuppressive agent comprises the isomeric cyclosporine analogue mixture in an amount selected from the group consisting of about 0.05 mg to about 50 mg per kilogram of body weight per day; about 0.1 mg to about 10 mg per kilogram of body weight per day; about 0.5 to about 10 mg/kg/day; about 2 to about 6 mg/kg/day, administered orally twice a day; and about 0.5 to about 3 mg/kg/day, administered orally twice a day.

* * * * *